United States Patent
Richelson et al.

(10) Patent No.: US 6,723,560 B2
(45) Date of Patent: *Apr. 20, 2004

(54) USING POLYAMIDE NUCLEIC ACID OLIGOMERS TO ENGENDER A BIOLOGICAL RESPONSE

(75) Inventors: Elliott Richelson, Ponte Vedra Beach, FL (US); Beth Marie Tyler, Neptune Beach, FL (US); Bernadette Marie Cusack, Jacksonville, FL (US); Christopher Lee Douglas, Jacksonville, FL (US); Karen Jansen, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/168,791

(22) Filed: Oct. 8, 1998

(65) Prior Publication Data

US 2003/0100519 A1 May 29, 2003

(51) Int. Cl.[7] .......................... C07H 21/04; C12N 5/00; A61K 31/70
(52) U.S. Cl. .......................... 435/375; 435/6; 435/325; 435/377; 514/44; 536/18.7; 536/24.1; 536/24.5
(58) Field of Search .................. 514/44; 435/91.1, 435/375, 325, 440, 377, 6; 536/18.7, 24.3, 23.1, 24.1, 24.5

(56) References Cited

U.S. PATENT DOCUMENTS

| | | |
|---|---|---|
| 5,142,047 A | 8/1992 | Summerton et al. |
| 5,217,866 A | 6/1993 | Summerton et al. |
| 5,470,974 A | 11/1995 | Summerton et al. |
| 5,539,082 A | 7/1996 | Nielsen et al. |
| 5,641,625 A | 6/1997 | Ecker et al. |
| 5,773,571 A | 6/1998 | Nielsen et al. |
| 5,783,682 A | 7/1998 | Cook et al. |
| 5,786,461 A | 7/1998 | Buchardt et al. |
| 6,156,501 A * | 12/2000 | McGall et al. ................. 435/6 |

FOREIGN PATENT DOCUMENTS

| | | |
|---|---|---|
| WO | WO 92/20702 | 11/1992 |
| WO | WO 92/20703 | 11/1992 |
| WO | WO 95/01370 | 1/1995 |
| WO | WO 95/04748 | 2/1995 |
| WO | WO 95/04749 | 2/1995 |
| WO | WO 95/14789 | 6/1995 |
| WO | WO 96/35705 | 11/1996 |
| WO | WO 97/38013 | 10/1997 |
| WO | WO 97/41150 | 11/1997 |
| WO | WO 98/53801 | 12/1998 |
| WO | WO 99/05302 | 2/1999 |
| WO | WO 99/13719 | 3/1999 |
| WO | WO 99/13893 | 3/1999 |
| WO | WO 99/20643 | 4/1999 |

OTHER PUBLICATIONS

Soomets et al., Frontiers in Biosciences vol. 4:782–786, Nov. 1, 1999.
Rezaei et al., Neurochemistry, vol. 12(2):317–320, Feb. 2001.
McMahon et al. "Altering behavioral responses and dopamine transporter protein with antisense peptide nucleic acids" (submitted for publication).
McMahon et al. Extracranial injection of antisense peptide nucleic acids targeted to the mu receptor decreases response to morphine and receptor protein levels in rat brain (submitted for publication).
McMahon et al. "Peptide Nucleic Acids Specifically Cause Antigene Effects in vivo by Systemic Injection" (submitted for publication).
Basu S. and Wickstrom E., "Synthesis and Characterization of a Peptide Nucleic Acid Conjugated to a D–Peptide Analog of Insulin–like Growth Factor 1 for Increased Cellular Uptake," *Bioconjugate Chem.* 8:481–488 (1997).
Bonham et al., "An Assessment of the Antisense Properties of RNase H–Competent and Steric–Blocking Oligomers," *Nucleic Acids Res.* 23:1197–1203 (1995).
Branch, A.D., "A Good Antisense Molecule is Hard to Find," *TIBS* 23:45–50 (1998).
Corey D.R., "Peptide Nucleic Acids: Expanding the Scope of Nucleic Acid Recognition," *Trends in Biotech.* 15:224–229 (1997).
Crooke S.T., "Antisense Research and Applications," Chapter 1, Basic Principles of Antisense Therapeutics, Springer–Verlag Press, Berlin, Heidelberg, New York, Chapter 1, p. 2–50 (1998).

(List continued on next page.)

*Primary Examiner*—Sean McGarry
*Assistant Examiner*—Janet L. Epps-Ford
(74) *Attorney, Agent, or Firm*—Fish & Richardson P.C., P.A.

(57) ABSTRACT

The invention involves methods and materials for extracellularly administering PNA oligomers to living cells. Specifically, the invention provides methods and materials of treating living cells with PNA oligomers such that the oligomers cross biological barriers and engender a biological response in a sequence specific manner. In addition, the invention provides methods and materials for orally administering PNA oligomers to animals such that the oligomers cross biological barriers and engender a biological response in a sequence specific manner. The invention also provides sense and antisense PNA oligomers that modulate transcription and translation, respectively. The invention also provides mismatch PNA oligomers that modulate the degree of an engendered biological response. In addition, the invention provides methods and materials for detecting PNA oligomers within a biological sample collected from an animal. Further, the invention provides methods and materials for screening potential PNA oligomers for the ability to engender a sequence specific biological response. Further, the invention provides methods of identifying the function of polypeptides and of determining the relative turnover rate of functional polypeptides.

43 Claims, 22 Drawing Sheets

OTHER PUBLICATIONS

Crooke S.T. et al., "Pharmacokinetic Properties of Several Novel Oligonucleotide Analogs in Mice," *J. Pharm. Exp. Ther.* 277:923–937 (1996).

Crooke S., "Antisense '97: A Roundtable on the state of the industry," *Nature Biotechnology* 15:519–524 (1997).

Demidov V.V. et al., "Stability of Peptide Nucleic Acids in Human Serum and Cellular Extracts," *Biochem. Pharmacol.* 48:1310–1313 (1994).

Ecker, D.J. and Freier, S.M., "PNA, Antisense, and Antimicrobials," *Nature Biotechnology* 16:332 (1998).

Egholm et al., PNA Hybridizes to Complementary Oligonucleotides Obeying the Watson–Crick Hydrogen–Bonding Rules, *Nature* 365:566–568 (1993).

Faruqi et al., Peptide Nucleic Acid–Targeted Mutagenesis of a Chromosomal Gene in Mouse Cells, *Proc. Natl. Acad. Sci. USA* 95:1398–1403 (1998).

Fraser G.L. et al., "In Vivo Modulation of Gene Expression by a Peptide Nucleic Acid Oligomer Antisense to the δ–Opioid Receptor," Abstracts—*Society of Neuroscience* 23:267.4 (1997).

Gambacorti–Passerini C. et al., "In Vitro Transcription and Translation Inhibition by Anti–Promyelocytic Leukemia (PML)/Retinoic Acid Receptor α and Anti–PML Peptide Nucleic Acid," *Blood* 88:1411–1417 (1996).

Good, L. and Nielsen, P.E., "Antisense Inhibition of Gene Expression in Bacteria by PNA Targeted to mRNA," *Nature Biotechnology* 16:355–358 (1998).

Good L. and Nielsen P.E., "Progress in Developing PNA as a Gene–Targeted Drug," *Antisense Nucleic Acid Drug Dev.* 7:431–437 (1997).

Gray G.D. et al., "Transformed and Immortalized Cellular Uptake of Oligodeoxynucleoside Phosphorothioates, 3'-Alkylamino Oligodeoxynucleotides, 2'-O-methyl Oligoribonucleotides. Oligodeoxynucleoside Methylphosphonates, and Peptide Nucleic Acids," *Biochem. Pharmacol.* 53:1465–1476 (1997).

Gura, T., "Antisense Has Growing Pains," *Science* 270:575–577 (1995).

Hanvey J.C. et al., "Antisense and Antigene Properties of Peptide Nucleic Acids," *Science* 258:1481–1485 (1992).

Hyrup B. and Nielsen P.E., "Peptide Nucleic Acids (PNA): Synthesis, Properties and Potential Applications," *Bioorg. Med. Chem.* 4:5–23 (1996).

Knudsen H. and Nielsen P., "Application of Peptide Nucleic Acid in Cancer Therapy," *Anti–Cancer Drugs* 8:113–118 (1997).

Koppelhus U. et al., "Efficient In Vitro Inhibition of HIV–1 Gag Reverse Transcription by Peptide Nucleic Acid (PNA) at Minimal Ratios of PNA/RNA," *Nucleic Acids Res.* 25:2167–2173 (1997).

Langel I. et al., "Cell Penetrating PNA Constructs," *J. Neurochem.* 69:B (1997).

Mardirossian K. et al., "In Vivo Hybridization of Technetium–99m–Labeled Peptide Nucleic Acid (PNA)," *J. Nuc. Med.* 38:907–913 (1997).

Monia BP et al., "Antitumour Activity of a Phosphorothioate Antisense Oligodeoxynucleotide Targeted Against C–Raf Kinase," *Nat. Med.* 2(6):668–675 (1996).

Monia BP et al., "Nuclease Resistance and Antisense Activity of Modified Oligonucleotides Targeted to Ha–ras," *J. Biol. Chem.* 271(24):14533–14540 (1996).

Monia BP, "Anti–Tumor Activity of C–Raf Antisense—Correction," *Nat. Med.* 5(2):127 (1999).

Nielsen P.E. et al., "Peptide Nucleic Acid (PNA). A DNA Mimic With a Peptide Backbone," *Bioconjugate Chem.* 5:3–7 (1994).

Norton et al., "Inhibition of Human Telomerase Activity By Peptide Nucleic Acids," *Nat. Biotech.,* 14:615–618 (1996).

Pardridge W.M. et al., "Vector–Mediated Delivery of a Polyamide ("Peptide") Nucleic Acid Analogue Through the Blood–Brain Barrier In Vivo," *Proc. Nat. Acad. Sci. USA* 92:5592–5596 (1995).

Pardridge W.M., "Vector–Mediated Drug Delivery of Antisense Therapeutics Through the Blood–Brain Barrier," *J. Neurochem.* 69A (1997).

Peffer N.J. et al., "Strand–Invasion of Duplex DNA by Peptide Nucleic Acid Oligomers," *Proc. Natl. Acad. Sci. USA* 90:10648–10652 (1993).

Pooga et al., "Cell Penetrating PNA Constructs Regulate Galanin Receptor Levels and Modify Pain Transmission In Vivo," *Nature Biotech.* 16:857–861 (1998).

Praseuth D. et al., "Peptide Nucleic Acids Directed to the Promoter of the α–Chain of the Interleukin–2 Receptor," *Biochim. Biophys. Acta.* 1309:226–238 (1996).

Rossi G. et al., "Blockade of Morphine Analgesia by an Antisense Oligodeoxynucleotide Against the Mu Receptor," *Life Sciences* 54:PL375–PL379 (1994).

Scarfi S. et al., "Synthesis, Uptake, and Intracellular Metabolism of a Hydrophobic Tetrapeptide–Peptide Nucleic Acid (PNA)–Biotin Molecule," *Biochem. Biophys. Res. Commun.* 236:323–326 (1997).

Senior, K., "Going FISHing With Peptide—Nucleic Acid," *Molecular Medicine Today,* p. 231 (1998).

Tanaka K. et al., "Structure and Functional Expression of the Cloned Rat Neurotensin Receptor," *Neuron* 4:847–854 (1990).

Taylor R.W. et al., "Selective Inhibition of Mutant Human Mitochondrial DNA Replication In Vitro by Peptide Nucleic Acids," *Nat. Genet.* 15(2):212–215 (1997).

Tyler B.M. et al., Specific Gene Blockade Shows That Peptide Nucleic Acids Readily Enter Neuronal Cells In Vivo, *FEBS Letters* 421:280–284 (1998).

Vita N. et al., "Cloning and Expression of a Complementary DNA Encoding a High Affinity Human Neurotensin Receptor," *FEBS Letters* 317:139–142 (1993).

Wittung P. et al., "Phospholipid Membrane Permeability of Peptide Nucleic Acid," *FEBS Letters* 365:27–29 (1995).

Yazaki T. et al., "Treatment of Glioblastoma U–87 by Systemic Administration of an Antisense Protein Kinase C–α Phosphorothioate Oligodeoxynucleotide," *Mol. Pharm.* 50:236–242 (1996).

\* cited by examiner

Figure 12
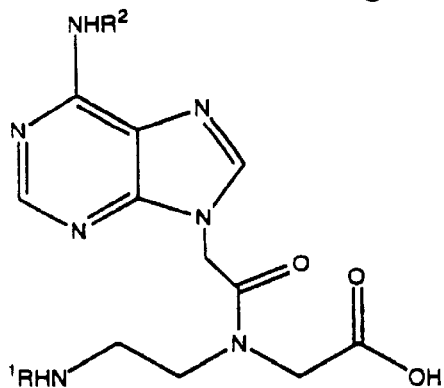
a. Structure of Fmoc-A(Bhoc)-OH.
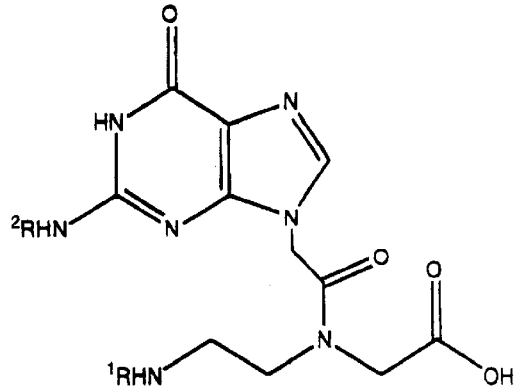
b. Structure of Fmoc-G(Bhoc)-OH.
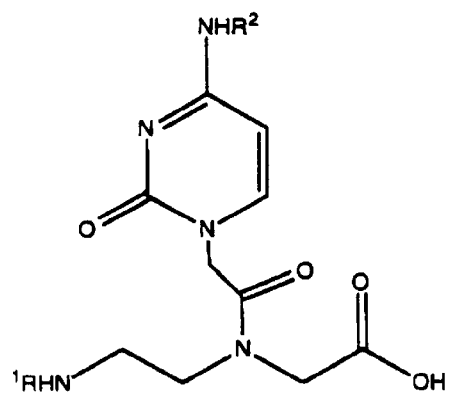
c. Structure of Fmoc-C(Bhoc)-OH.
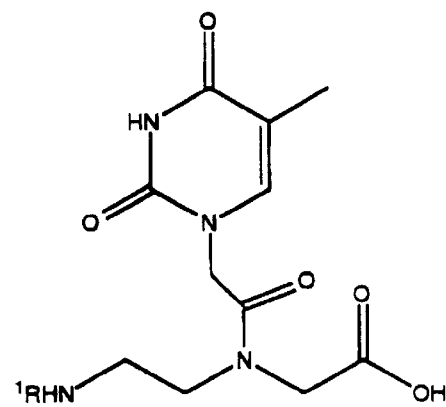
d. Structure of Fmoc-T-OH.
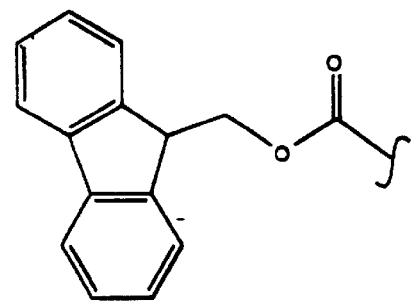
e. Structure of Fmoc Group.
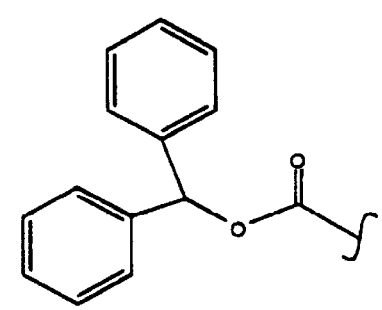
f. Structure of Bhoc Group.
$R^1$ = Fmoc  $R^2$ = Bhoc Gel Shift Assay

SEQUENCE LISTING

<160> NUMBER OF SEQ ID NOS: 14

<210> SEQ ID NO 1
<211> LENGTH: 12

-continued

```
<212> TYPE: DNA
<213> ORGANISM: Rat

<400> SEQUENCE: 1
cattgctcaa ac                                                    12

<210> SEQ ID NO 2
<211> LENGTH: 14
<212> TYPE: DNA
<213> ORGANISM: Rat

<400> SEQUENCE: 2
cagcctcttc ctct                                                  14

<210> SEQ ID NO 3
<211> LENGTH: 12
<212> TYPE: DNA
<213> ORGANISM: Rat

<400> SEQUENCE: 3
gccagatgtt gc                                                    12

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gccactgtca aggtcgtc                                              18

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
agccagcaga ccacaaag                                              18

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ccgtgtcttg gttctatgg                                             19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggtattggaa aagccgtagc                                            20

<210> SEQ ID NO 8
<211> LENGTH: 20
<212> TYPE: DNA
```

```
<213> ORGANISM: Artificial Sequence
<220> FEATURE:
<223> OTHER INFORMATION: primer

<400> SEQUENCE: 8
ctgtatttat cgtctgctgg                                               20

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
agtggagttt tgctgttcg                                                19

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
tgatgacatc aagaaggtgg tgaag                                         25

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
tccttggagg ccatgtaggc cat                                           23

<210> SEQ ID NO 12
<211> LENGTH: 12
<212> TYPE: DNA
<213> ORGANISM: Artificial Sequence
<220> FEATURE:
<223> OTHER INFORMATION: PNA oligomer having rat mismatch sequence

<400> SEQUENCE: 12
tatggcacag ac                                                       12

<210> SEQ ID NO 13
<211> LENGTH: 12
<212> TYPE: DNA
<213> ORGANISM: Rat

<400> SEQUENCE: 13
gtttgagcaa tg                                                       12

<210> SEQ ID NO 14
<211> LENGTH: 14
<212> TYPE: DNA
<213> ORGANISM: Rat

<400> SEQUENCE: 14
tacaacttca tctg                                                     14
```

USING POLYAMIDE NUCLEIC ACID OLIGOMERS TO ENGENDER A BIOLOGICAL RESPONSE

STATEMENT AS TO FEDERALLY SPONSORED RESEARCH

Funding for the work described herein was provided by the federal government, which may have certain rights in the invention.

BACKGROUND

1. Technical Field

The invention relates to administering polyamide nucleic acid oligomers to living cells such that the polyamide nucleic acid oligomers engender a sequence specific biological response.

2. Background Information

Polyamide nucleic acids (PNAs) are DNA analogs containing neutral amide backbone linkages. Unlike DNA oligomers, PNA oligomers can bind DNA by displacing one strand of the duplex to form a stable D-loop structure (Peffer et al., Proc. Natl. Acad. Sci. USA 90:10648–10652 (1993) and Møllegaard et al., Proc. Natl. Acad. Sci. USA 91:3892–3895 (1994)). Interestingly, binding of PNA oligomers to DNA is independent of DNA strand polarity, allowing PNA oligomers to bind in both parallel and anti-parallel fashion (Egholm et al., Nature 365:566–568 (1993) and Peffer et al., Proc. Natl. Acad. Sci. USA 90:10648–10652 (1993)). In addition, PNA oligomers are less susceptible to enzymatic degradation (Demidov et al., Biochem. Pharmacol. 48:1310–1313 (1994)) and bind RNA with higher affinity than analogous DNA oligomers. Taken together, these properties suggest that PNA oligomers have great potential in both antigene and antisense approaches for regulating gene expression.

The success of an oligonucleotide analog as an antigene or antisense agent requires that the oligonucleotide be taken up by cells in reasonable quantities such that the oligonucleotide reaches its target at a sufficient concentration. PNA oligomers, however, have low phospholipid membrane permeability (Wittung et al., FEBS Letters 365:27–29 (1995)) and have been reported to be taken up by cells very poorly (Hanvey et al., Science 258:1481–1485 (1992); Nielsen et al., Bioconjugate Chem. 5:3–7 (1994); Bonham et al., Nucleic Acids Res. 23:1197–1203 (1995); Gray et al., Biochem. Pharmacol. 48:1465–1476 (1997)), which would appear to limit their potential uses in antigene and antisense approaches.

Recent strategies devised to improve cellular uptake of PNA oligomers involve conjugating other molecules to PNA sequences. Specifically, conjugating a small peptide sequence that binds the insulin-like growth factor 1 receptor (IGF1R) to a PNA oligomer increases cellular uptake of labeled PNA sequences by IGF1R-expressing cells, whereas conditions using unconjugated PNA sequences or cells lacking IGF1R show negligible cellular uptake (Basu S. and Wickstrom E., Bioconjugate Chem. 8:481–488 (1997)). These results suggest that conjugating receptor ligand molecules to PNA oligomers can increase cellular uptake; however, the ability of these receptor ligand-conjugated PNA oligomers to influence biological activity once inside the target cells remains unknown. Further, PNA oligomers will gain entrance only into cells expressing that particular targeted receptor. Thus, an appropriate ligand molecule would have to be designed and coupled to PNA oligomers for each cell type of interest. In addition, the level of receptor expression can influence the permeability of ligand-conjugated PNA oligomers.

The use of PNA oligomers to manipulate brain protein expression, an approach that would greatly aid the understanding of brain function as well as neurological disease, has an additional problem. The endothelial wall of capillaries in both brain and spinal cord creates a barrier (blood-brain barrier; BBB) that excludes the uptake of molecules into these organs. Although specialized transport systems operate within the BBB to allow certain circulating molecules to cross, many pharmaceutical agents are not recognized and thus have poor BBB permeability. This appears true for PNA molecules since the transport of PNAs across the BBB is reported to be negligible (Pardridge et al., Proc. Natl. Acad. Sci. USA 92:5592–5596 (1995)). Therefore, PNA oligomers targeting brain proteins administered outside the central nervous system need to cross two barriers, the BBB and the plasma membrane of individual cells within brain, whereas PNA oligomers administered directly into brain need to cross one barrier, the plasma membrane of individual cells.

Various drug delivery strategies can circumvent the BBB permeability problem (Pardridge, Pharmacol. Toxicol. 71:3–10 (1992); Pardridge, Trends Biotechnol. 12:239–245 (1994)). For example, PNA molecules can undergo transport through the BBB when the amino terminus is biotinylated and linked to a streptavidin conjugated monoclonal antibody specific for transferrin receptor (OX26-SA; Pardridge et al., Proc. Natl. Acad. Sci. USA 92:5592–5596 (1995)). The OX26-SA antibody delivers linked molecules to the brain presumably by receptor-mediated endocytosis, given the high transferrin receptor concentrations located on the BBB. These studies suggest that antibody-conjugation strategies provide a mechanism for PNA oligomers to cross the BBB. No data, however, exist as to whether the biotinylated PNA linked to OX26-SA actually enters cells or not. In addition, the utility of PNA delivery methods that rely on conjugating other molecules to PNA oligomers remains unclear since these other molecules may influence the desired functionality of particular PNAs.

SUMMARY

The present invention relates to PNA oligomers that influence biological activity in a sequence specific manner. Specifically, this invention relates to the discovery that PNA oligomers administered extracellularly cross biological barriers and elicit a sequence specific biological response in living cells. This discovery is in direct opposition to the current understanding of the physical properties of PNA oligomers and has far-reaching implications for both gene therapy and research purposes. Further, extracellularly administering PNA oligomers to living cells circumvents the need to micro-inject PNA oligomers directly into cells as well as the need to permeabilize cells. In addition, this invention provides for the treatment of cells in vivo such that a behavioral response is observed in an organism. Thus, this invention describes methods and materials that allow any polypeptide to be manipulated and studied in living cells. For example, the expression of a specific polypeptide can be knocked-out in adult organisms for the duration of PNA oligomer treatment. In addition to greatly aiding the advancement of basic scientific research, this ability to manipulate polypeptide expression and thus function in a sequence specific manner is clearly beneficial to gene therapy approaches involving the treatment of cancer, aging, behavioral diseases, infections, and auto-immune diseases.

In addition, this invention relates to the following two discoveries: 1) antisense PNA oligomers administered to an animal cross biological barriers and modulate translation in a sequence specific manner, and 2) sense PNA oligomers administered to an animal cross biological barriers and modulate transcription in a sequence specific manner. Thus, this invention provides two powerful in vivo methods for manipulating polypeptide expression in a sequence specific manner. Clearly, having the ability to modulate two distinct steps involved in polypeptide synthesis will further the advancement of basic scientific research and provide useful methods for treating disease. The term "antisense PNA oligomer" refers to any PNA oligomer having sequence specificity for an RNA molecule found within a cell. The term "sense PNA oligomer" refers to any PNA oligomer having sequence specificity for a region of nucleic acid that can be used as the template strand during transcription, including reverse transcription.

This invention also relates to the discovery that a mismatch PNA oligomer crosses biological barriers and engenders a biological response to a degree less than that engendered by a PNA oligomer targeting the same sequence but having, for example, no base pair mismatches. In other words, this invention relates to the discovery that the degree to which a biological response is engendered can be modulated by changing the sequence of a particular PNA oligomer to introduce base pair mismatches with a target sequence. Having the ability to alter the degree of an engendered biological response provides a useful mechanism for obtaining a particular desired effect. The term "mismatch PNA oligomer" refers to any PNA oligomer having a sequence that contains at least one base pair mismatch with respect to a target sequence. The term "target sequence" refers to any purine/pyrimidine sequence to which another purine/pyrimidine sequence (e.g., PNA, RNA, or DNA oligomer) exhibits sequence specificity.

Further, this invention relates to the discovery that PNA oligomers can be detected in a biological sample collected from an animal. Specifically, the presence and amount of a PNA oligomer can be determined by adding a sequence specific probe to a biological sample and examining that sample for the presence of probe/PNA oligomer complex. The probe/oligomer complex provides an indication of the presence of the PNA oligomer. Detecting PNA oligomers in a biological sample such as blood provides a useful method for monitoring the presence and concentration of a particular PNA oligomer during a treatment regimen. For example, quantifying the concentration of a particular PNA oligomer in a patient's blood or tissue can allow clinicians to adjust the amount of PNA oligomer administered to the patient such that the desired concentration and biological response is achieved or maintained.

In general, the invention features methods of treating an animal containing a cell. The methods include administering a PNA oligomer to the animal under conditions such that the PNA oligomer enters the cell (e.g., a nervous system cell and a gastrointestinal cell) and modulates transcription in a sequence specific manner. The administration can be an extracranial (e.g., intraperitoneal, intravenous, and oral) or intracranial administration. The PNA oligomer can be carrier-free and capable of crossing the blood-brain barrier of the animal. The PNA oligomer typically has sequence specificity for at least a portion of a coding strand of DNA within the cell. That portion of a coding strand of DNA can regulate, or be a template for, synthesis of an RNA molecule (e.g., mRNA). Specific PNA oligomers can include oligomers having sequences such as set out in SEQ ID NO:s 13 and 14. The modulation of transcription can reduce expression of a polypeptide within the animal and/or cause a physiological change in the animal. The polypeptides can be expressed intracranially or extracranially (e.g., in the gastrointestinal tract) in the animal. In addition, the polypeptides expressed in the animal can include receptors (e.g., neurotensin receptors). Further, the methods can involve administering a second PNA oligomer to the animal under conditions such that the second PNA oligomer enters at least one cell within the animal and modulates translation in a sequence specific manner.

Another aspect of the invention features an article of manufacture that combines packaging material and a PNA oligomer. The packaging material includes a label or package insert indicating that the PNA oligomer can be administered to an animal to modulate transcription in a sequence specific manner.

In another aspect, the invention features methods of treating an animal containing a cell. The methods include administering a PNA oligomer to the animal under conditions such that the PNA oligomer enters the cell (e.g., a nervous system cell) and engenders a biological response in a sequence specific manner. In this case, the PNA oligomer has sequence specificity for a target sequence within the cell while possessing at least one base pair mismatch with that target sequence. A specific PNA oligomer can include a PNA oligomer having the sequence set out in SEQ ID NO: 12. The target sequence can be at least a portion of a coding strand of DNA within the cell. That portion of a coding strand of DNA can regulate, or be a template for, synthesis of an RNA molecule that, for example, regulates expression of or encodes a polypeptide. The biological response can be characterized by a physiological change in the animal.

The invention also features methods for identifying a mismatch PNA oligomer that engenders a modulated biological response in a subject animal having a target sequence. A modulated biological response is in comparison to a biological response engendered by a reference PNA oligomer. The methods include obtaining reference information about the biological response engendered by the reference PNA oligomer administered to a reference animal having the target sequence. This reference PNA oligomer has sequence specificity for the target sequence. The methods also include determining test information about the biological response engendered by a test PNA oligomer administered to the subject animal. The reference and test PNA oligomers have different sequences and the test PNA oligomer has sequence specificity for the target sequence while possessing at least one base pair mismatch with that target sequence. In addition, the methods include identifying the test PNA oligomer as a mismatch PNA if the test PNA engenders the modulated response.

Another aspect of the invention features kits for treating an animal containing a cell with a target sequence. The kits contain a plurality of PNA oligomers with each PNA oligomer having sequence specificity for the target sequence while possessing a sequence different from the sequence of the other PNA oligomers. One of the PNA oligomers can have a sequence completely complementary with the target sequence. At least one of the PNA oligomers can have a sequence having at least one base pair mismatch with the target sequence. The plurality of PNA oligomers can be a series of PNA oligomers having incrementally increasing degrees of base pair mismatch with the target sequence.

In another aspect, the invention features methods for treating an animal containing a cell with a target sequence.

The methods include selecting a first PNA oligomer from a kit. The kit contains a plurality of PNA oligomers with each PNA oligomer having sequence specificity for the target sequence while possessing a sequence different from the sequence of the other PNA oligomers. The methods also include administering the first selected PNA oligomer to the animal under conditions such that the first selected PNA oligomer enters the cell and engenders a biological response in a sequence specific manner. The methods can further include selecting a second PNA oligomer from the kit and administering that second selected PNA oligomer to the animal under conditions such that the second selected PNA oligomer enters a cell in the animal and engenders the biological response to a modulated degree compared to the response engendered by the first selected PNA oligomer.

Another aspect of the invention features an article of manufacture that combines packaging material and a PNA oligomer. The packaging material includes a label or package insert indicating that the PNA oligomer can be administered to an animal under conditions such that the PNA oligomer engenders a biological response in a sequence specific manner. The PNA oligomer can have sequence specificity for a target sequence while possessing at least one base pair mismatch with the target sequence.

Another aspect of the invention features methods for detecting a PNA oligomer in a biological sample collected from an animal. The methods include providing an oligonucleotide to the sample. The oligonucleotide has sequence specificity for the PNA oligomer. The methods also include examining the sample for the presence or absence of an oligonucleotide/PNA oligomer complex. The oligonucleotide/oligomer complex provides an indication of the presence of the PNA oligomer. The PNA can be carrier-free. The biological sample can be a tissue sample (e.g., brain, liver, kidney, and heart tissue) or a blood sample. The oligonucleotide can be a labeled oligonucleotide (e.g., radioactively labeled). The examining step can include separating the oligonucleotide from any of the oligonucleotide/PNA oligomer complexes. The separation can be an electrophoretic separation.

Another aspect of the invention features an article of manufacture that combines packaging material and an oligonucleotide. The packaging material includes a label or package insert indicating that the oligonucleotide can detect a PNA oligomer in a biological sample collected from an animal. The oligonucleotide has sequence specificity for the oligomer.

Another aspect of the invention features methods of treating animals by orally administering PNA oligomers under conditions such that the PNA oligomers engender a biological response in a sequence specific manner. The PNA oligomers can be carrier-free and are capable of crossing biological barriers such as the plasma membrane of cells and the blood-brain barrier of an animal. The PNA oligomers typically have sequence specificity for a nucleic acid sequence that encodes a polypeptide or regulates the expression of a polypeptide expressed in the animal. The polypeptides can be expressed intracranially or extracranially. Polypeptides expressed in the animal can include transporters as well as those polypeptides that participate in cell signaling. Cell signaling polypeptides include polypeptides that participate in opioid signaling. Opioid signaling polypeptides include opioid receptors, for example morphine and neurotensin receptors. Transporter polypeptides can be serotonin transporters. Extracranially expressed polypeptides include polypeptides expressed outside the brain and cranium, for example in the gastrointestinal tract. Specific PNA oligomers can include oligomers having sequences such as set out in SEQ ID NO:s 1, 2, and 3. The biological response engendered by the extracellular administration of PNA oligomers can be a modification, for example a reduction, of polypeptide expression. Biological responses also can be characterized by a physiological change in an animal.

Another aspect of the invention features an article of manufacture that combines packaging material and PNA oligomers. The packaging material includes a label or package insert indicating that the PNA oligomers can be orally administered to an animal for the purpose of engendering a biological response in a sequence specific manner.

Another aspect of the invention features methods of treating living cells by extracellularly administering PNA oligomers under conditions such that the PNA oligomers engender a biological response in a sequence specific manner. The PNA oligomers can be carrier-free and can be administered in vivo to an animal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include transporters as well as those polypeptides that participate in cell signaling. Cell signaling polypeptides include polypeptides that participate in opioid signaling. Opioid signaling polypeptides include opioid receptors, for example morphine and neurotensin receptors. Transporter polypeptides can be serotonin transporters. Extracranially expressed polypeptides include polypeptides expressed outside the brain and cranium, for example in the gastrointestinal tract. Specific PNA oligomers can include oligomers having sequences such as set out in SEQ ID NO:s 1, 2, and 3. The biological response engendered by the extracellular administration of PNA oligomers can be a modification, for example a reduction, of polypeptide expression. Biological responses also can be characterized by a physiological change in an animal.

Another aspect of the invention features a method of screening PNA oligomers for the ability to engender a sequence specific biological response by extracellularly administering PNA oligomers to living cells. The PNA oligomers can be carrier-free and can be administered in vivo to an animal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include those polypeptides that participate in cell signaling. Cell signaling polypeptides include polypeptides that participate in opioid signaling. Opioid signaling polypeptides include opioid receptors, for example morphine and neurotensin receptors. Extracranially expressed polypeptides include polypeptides expressed outside the brain and cranium, for example in the gastrointestinal tract. The biological response engendered by the extracellular administration of PNA oligomers can be a modification, for example a reduction, of polypeptide expression. Biological responses also can be characterized by a physiological change in an animal.

Another aspect of the invention features a method of identifying polypeptide function by extracellularly administering PNA oligomers to living cells such that the PNA oligomers alter the expression of the polypeptide in a sequence specific manner and examining those cells for an activity that is influenced by the specific PNA oligomer. The PNA oligomers can be carrier-free and can be administered in vivo to an animal, such as a murine mammal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include those polypeptides that participate in cell signaling. Cell signaling polypeptides include polypeptides that participate in opioid signaling. Opioid signaling polypeptides include opioid receptors, for example morphine and neurotensin receptors. Extracranially expressed polypeptides include polypeptides expressed outside the brain and cranium, for example in the gastrointestinal tract. Specific PNA oligomers can include oligomers having sequences such as set out in SEQ ID NO:s 1 and 2. The biological response engendered by the extracellular administration of PNA oligomers can be a modification, for example a reduction, of polypeptide expression. Biological responses also can be characterized by a physiological change in an animal.

Another aspect of the invention features a method of measuring the relative turnover rate of functional polypeptides having a defined activity by extracellularly administering PNA oligomers to living cells such that the PNA oligomers influence the defined activity, and determining the time after PNA oligomer administration that the defined activity is maximally influenced. In addition, the time from when the defined activity is influenced maximally to when the activity returns to normal can be determined.

Another aspect of the invention features an article of manufacture that combines packaging material and PNA oligomers. The packaging material includes a label or package insert indicating that the PNA oligomers can be extracellularly administered to living cells for the purpose of engendering a biological response in a sequence specific manner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 12a–12f depicts the structures of PNA monomers with protecting groups.

DETAILED DESCRIPTION

Figure 1:
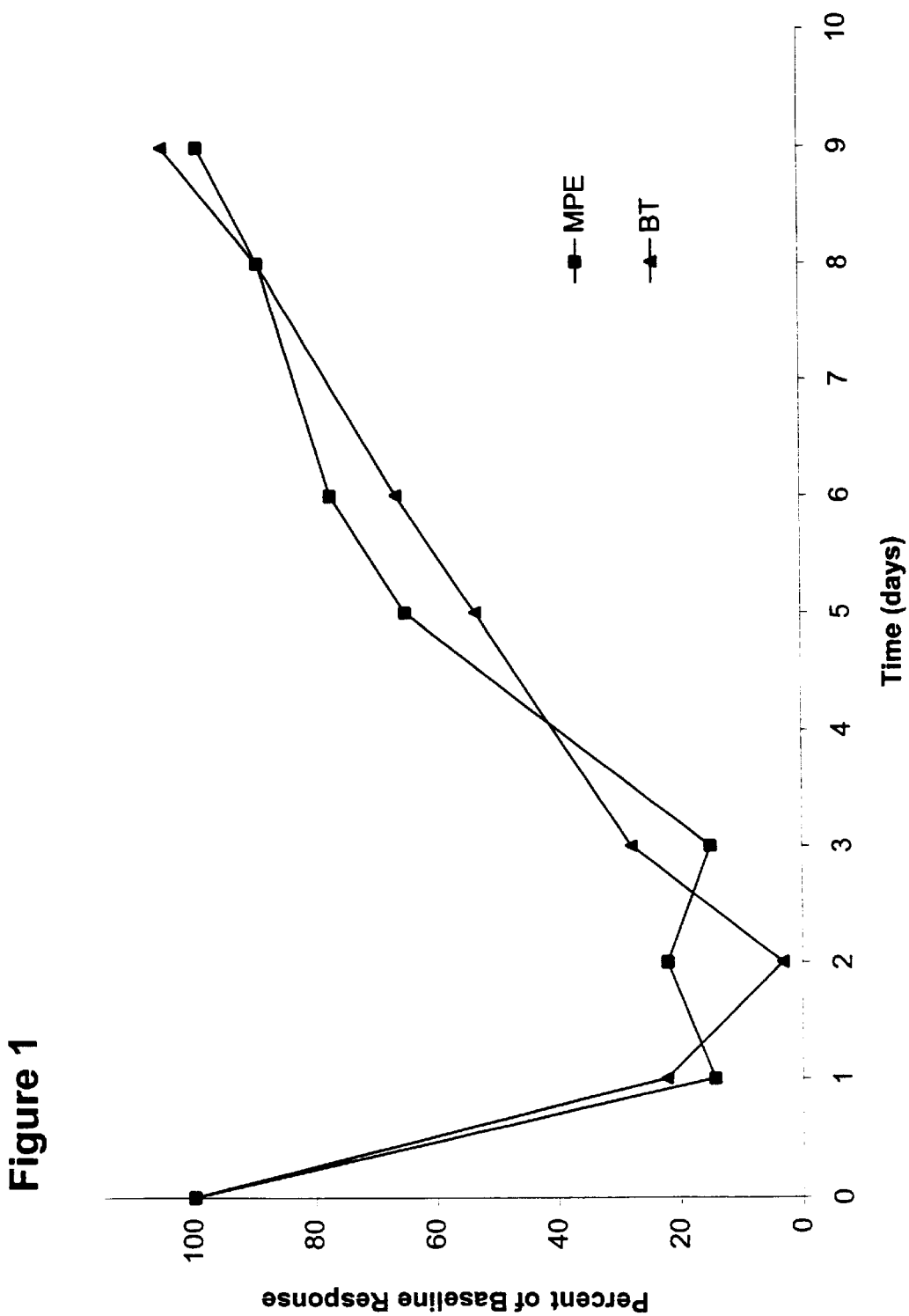
FIG. 1 is a graph plotting the maximal possible effect and body temperature as a percent of baseline response for rats treated intracranially on days −4, −2, and 0 with NTR1-PNA oligomers and challenged with neurotensin (NT).

The invention involves methods and materials for extracellularly administering PNA oligomers to living cells. Specifically, the invention provides methods of treating living cells with PNA oligomers such that the oligomers cross biological barriers and engender a biological response in a sequence specific manner. This invention also provides methods of screening potential PNA oligomers for the ability to engender a sequence specific biological response. Further, this invention provides methods of identifying the function of polypeptides and of determining the relative turnover rate of functional polypeptides.

Extracellularly Administering PNA Oligomers to Living Cells

PNA oligomers can be administered to living cells extracellularly such that they cross a biological barrier and engender a sequence specific biological response. That a PNA oligomer crosses a biological barrier can be inferred from the ability of the PNA oligomer to engender a sequence specific biological response requiring interactions with specific nucleic acid sequences contained within a living cell. For example, if a PNA oligomer having sequence specificity for the nucleic acid encoding protein X is administered extracellularly and engenders a sequence specific biological response by altering the expression of protein X, then it can be inferred that that particular PNA oligomer also crossed a biological barrier, the plasma membrane. In other words, the nature of sequence specific biological responses engendered by PNA oligomers implies that PNA oligomers crossed a biological barrier to interact with specific nucleic acid sequences within living cells. Thus, a sequence specific biological response is any response of a living cell that is attributed to the actual sequence of a PNA oligomer, such as the alteration of protein X expression as stated above. In addition to analyzing polypeptide expression, sequence specific biological responses can be determined by analyzing any biological activity including, without limitation, cellular activities such as signaling, adherence, movement, proliferation, differentiation, and apoptosis as well as physiological activities such as development, growth, reproduction, immunity, pain, anti-nociception, perception, depression, and memory.

PNA oligomers used to engender a sequence specific biological response in a living cell can be obtained from PerSeptive Biosystems (Framingham, Mass., USA) or from authorized suppliers. Alternatively, PNA oligomers can be synthesized manually from PNA monomers obtained from PerSeptive Biosystems as described elsewhere (Norton J. C., *Bioorg. Med. Chem.* 3:437–445 (1995) and Cory D. R., *Trends in Biotech.* 15:224–229 (1997)). PNA oligomers can be any length providing they contain at least two PNA monomers. Thus, PNA oligomers can range in size from dinucleotides to entire genes or more. PNA oligomers also can have any sequence providing the PNA oligomer crosses a biological barrier, such as the BBB of an organism or the plasma membrane of a cell, and engenders a sequence specific biological response. For example, a PNA oligomer can have sequence specificity for any nucleic acid sequence that encodes a polypeptide or regulates the expression of a polypeptide. With the current advances in recombinant nucleic acid and nucleic acid sequencing technology, countless nucleic acid sequences are not only known but also readily available from sequence databases such as Genebank®.

In addition, PNA oligomers can be either modified or unmodified with the condition that they cross a biological barrier and engender a sequence specific biological response. Possible types of modification can include, but are not limited to, modifications with acridine, protein, backbone chemistries, DNA, peptide, bis-PNA, biotin, and fluorescein. Unmodified PNA oligomers can include any oligomer made essentially from PNA monomers, but without further modifications designed to enhance the crossing of plasma membranes or the BBB. Such unmodified PNA oligomers are designated herein as "carrier-free." It is to be understood, however, that "carrier-free" PNA oligomers can be modified in other ways, for example to enhance detectability (e.g., with various labels).

The mode of administering PNA oligomers to living cells can be any mode wherein the administration is extracellular and the administered PNA oligomers engender a sequence specific biological response. For example, PNA oligomers can be applied directly to tissue culture medium when treating cells in vitro or can be administered to an organism when treating cells in vivo. When treating cells in vivo, PNA oligomers can be administered by various routes. Various pharmaceutically acceptable carriers can be used for in vivo administration to animals, including for example physiological saline, artificial cerebral-spinal fluid, or other known carriers appropriate to specific routes of administration.

For the purpose of this invention, two general routes of administration are provided: intracranial and extracranial. Examples of intracranial routes of administration include, but are not limited to, intracisternal, intraventricular, and intradural. Examples of extracranial routes of administration include, but are not limited to, oral, intravenous, intramuscular, intraperitoneal, subcutaneous, intradermal, topical, or the like. Oral administration can be by various methods including, without limitation, swallowing and gastric intubation. The route of administration, whether intracranial or extracranial, can depend on a variety of factors, such as treatment environment and therapeutic goals. In addition, PNA oligomers may be administered on a continuous or an intermittent basis. Further, an extracellular administration of PNA oligomers can contain PNA oligomers having a single sequence specificity or can contain different PNA oligomers having a plurality of sequence specificities.

The dosages of PNA oligomers will depend on many factors including the mode of administration and the living cells being treated whether within a living organism or within culture. Typically, the concentration of PNA oligomers contained within a single dose will be an amount that effectively engenders a sequence specific biological response without inducing significant toxicity.

Screening Potential PNA Oligomers

Potential PNA oligomers can be screened for the ability to engender a desired biological response in a sequence specific manner. The desired sequence specific biological response can be any alteration of a particular activity or can be a specific level of alteration of a particular activity. For example, one desired sequence specific biological response could be any reduction in polypeptide expression, whereas another could be the complete knock-out of polypeptide expression. To screen potential PNA oligomers, single PNA oligomers or pools of different PNA oligomers are extracellularly administered to living cells as described herein. After administration, the living cells are monitored for the desired sequence specific biological response. Particular pools of PNA oligomers that engender the desired sequence specific biological response can be divided and re-screened sequentially until a single PNA oligomer sequence is identified, if necessary.

Identifying Polypeptide Function

The function of any polypeptide expressed in a living cell can be identified by the following method. PNA oligomers having sequence specificity for the nucleic acid sequence that encodes a polypeptide or regulates the expression of a polypeptide can be administered extracellularly to living cells such that the expression of that particular polypeptide is altered in a sequence specific manner. After administration, the cells can be examined to determine an activity specifically influenced by the altered polypeptide expression caused by the administered PNA oligomers. Living cells can be treated either in vivo or in vitro and examined either in vivo or in vitro. For example, PNA oligomers can be administered to an organism and, after administration, cells taken from the organism for examination. In addition, PNA oligomers can be administered to an organism and the organism itself examined after administration. Thus, the examination of living cells can include, without limitation, examination of an organism. In addition to examining the living cells themselves after administration, any component of the living cells can be examined. For example, PNA oligomers can be administered to an organism and then cells can be extracted and manipulated so that a particular component of the cell is examined.

Measuring Relative Turn-over Rate

The relative turn-over rate of a functional polypeptide having a defined activity can be measured by the following method. PNA oligomers having sequence specificity for a nucleic acid sequence that encodes a particular polypeptide having a defined activity or that regulates the expression of the polypeptide can be administered extracellularly to living cells such that the defined activity attributed to the polypeptide is influenced in a sequence specific manner. The turn-over rate for the polypeptide can be determined by measuring the time, after administration, needed for the activity attributed to the polypeptide to be maximally influenced. In addition, the turn-over rate can be further defined by measuring the time needed for the maximally influenced activity to return to a normal level following removal of the PNA oligomers from the cellular environment. A normal level is the level of activity measured before any administration of PNA oligomers. From these data the relative turn-over rate of the polypeptide can be determined by comparison to turn-over rates of other polypeptides derived in a similar manner. These comparisons can be made between polypeptides with either similar or different biological activities.

Antisense PNA Oligomers

As described herein, a PNA oligomer can have any sequence providing the PNA oligomer crosses a biological barrier, such as the BBB of an organism or the plasma membrane of a cell, and engenders a sequence specific biological response. A particular PNA oligomer having these properties can be designated as either an "antisense" or "sense" PNA oligomer, depending on the target sequence of the PNA oligomer. For the purpose of this invention, an "antisense" PNA oligomer can be any PNA oligomer having sequence specificity for an RNA molecule found within a cell. For example, an antisense PNA oligomer can be a PNA oligomer having sequence specificity for at least a portion of a pre-mRNA, mRNA, viral mRNA, rRNA, or tRNA molecule. It is to be understood that antisense PNA oligomers also will have sequence specificity for the non-template strand of nucleic acid and not the template strand from which such RNA molecules are transcribed.

Although not limited to any particular mode of action, an antisense PNA oligomer can interact in a sequence specific manner with an mRNA molecule within a cell and prevent translation of that mRNA molecule into a polypeptide. The interaction of the antisense PNA oligomer and mRNA molecule within a cell presumably results in a PNA/RNA complex that prevents translation through steric hindrance. In addition, the formation of a PNA/RNA complex using an antisense PNA oligomer does not appear to promote the degradation of the RNA molecule. Thus, the biological response engendered by an antisense PNA oligomer does not appear to rely on the participation of polypeptides such as RNAses.

Briefly, translation of a genetic message from mRNA into a polypeptide involves three stages: initiation, elongation, and termination. During initiation, translational machinery comes together to form an initiation complex with the mRNA molecule near a translation initiation site. Once this initiation complex is assembled, elongation can begin. During elongation, the ribosome synthesizes a peptide chain according to the sequence provided by the mRNA molecule. Once the ribosome reaches a stop codon, translation is completed by a termination process. During termination, the mRNA, ribosome, and newly synthesized polypeptide disassociate.

An antisense PNA oligomer having sequence specificity for a sequence near an initiation region of the mRNA molecule can prevent translation presumably by forming a PNA/RNA complex that interferes with the formation of an initiation complex at that site. If a particular mRNA molecule has multiple initiation sites, then an antisense PNA oligomer having sequence specificity for a sequence at or near an upstream initiation site can be used to direct translation initiation to a downstream site. Thus, antisense PNA oligomers can be used to prevent translation initiation as well as direct translation initiation to a downstream site.

An antisense PNA oligomer having sequence specificity for a portion of the coding sequence of an mRNA molecule can prevent translation presumably by forming a PNA/RNA complex that interferes with elongation. It is noted that an antisense PNA oligomer having sequence specificity for a portion of the coding sequence of an mRNA molecule may produce a truncated polypeptide. Such truncated polypeptides can have modified function with respect to their full-length counterparts. For example, a cell surface receptor lacking a portion of its C-terminus may have modified intracellular signaling activity. Taken together, antisense PNA oligomers can be used to prevent elongation beyond a specific point, resulting in reduced polypeptide synthesis or the synthesis of truncated polypeptides.

An antisense PNA oligomer having sequence specificity for a sequence near a stop codon can reduce polypeptide synthesis presumably by forming a PNA/RNA complex that interferes with the termination process. Interfering with the termination process can prevent the disassociation of the ribosome, polypeptide complex from the mRNA molecule, resulting in an accumulation of such complexes along the mRNA molecule. In this case, the newly synthesized polypeptide would not be released from the ribosome and therefore would be unable to perform its biological function. Thus, antisense PNA oligomers can be used to reduce translation termination, resulting in reduced synthesis of functional polypeptides.

Sense PNA Oligomers

For the purpose of this invention, a "sense" PNA oligomer can be any PNA oligomer having sequence specificity for a region of nucleic acid that can be used as the template strand during transcription, including reverse transcription. Although not limited to any particular mode of action, a sense PNA oligomer can interact in a sequence specific manner with the template strand of a nucleic acid molecule and prevent transcription of that template. The interaction of the sense PNA oligomer and template within a cell presumably results in a PNA/nucleic acid complex that prevents transcription by steric hindrance. For example, a PNA/DNA complex can reduce the production of RNA by interfering with an RNA polymerase. Thus, a sense PNA oligomer can prevent the production of mRNA, resulting in a reduced level of polypeptide synthesis.

Use of such sense PNA oligomers to modulate transcription is typically termed an "antigene" approach since sense PNA oligomers can operate at the level of DNA. It is noted that the template strand of nucleic acid can be a DNA or RNA molecule. For example, a sense PNA oligomer can be a PNA oligomer having sequence specificity for the template strand of a host DNA molecule that can be transcribed into an mRNA molecule, or a viral RNA molecule that can be transcribed into DNA by reverse transcriptase. In addition, a sense PNA oligomer can be a PNA oligomer having sequence specificity for at least a portion of a regulatory, intron, or exon region of a template strand of nucleic acid. It is noted that a sense PNA oligomer may be a more potent inhibitor of biological activity than an antisense PNA oligomer since the amount of target available for an antisense PNA oligomer (e.g., many copies of mRNA within a cell) can be much more than that available for a sense PNA oligomer (e.g., two copies of DNA within a cell).

Sense and antisense PNA oligomers can be given in combination to engender a biological response that is more pronounced, longer lasting, or otherwise different than the biological response engendered by either the sense or antisense PNA oligomer alone. In addition, mismatch PNA oligomers can be used in combination with other PNA oligomers.

Mismatch PNA Oligomers

A mismatch PNA oligomer can be any PNA oligomer, including a sense or antisense PNA oligomer, having a sequence that contains at least one base pair mismatch with respect to a target sequence. For example, a PNA oligomer that targets 5'-GGGGGG-3' and has a sequence 5'-CCCCCC-3' would not be a mismatch PNA oligomer, but a PNA oligomer that has a sequence 5'-CCCACC-3' would be a mismatch PNA oligomer with respect to that 5'-GGGGGG-3' target sequence. In addition, any mismatch PNA oligomer is within the scope of this invention provided the mismatch PNA oligomer can cross a biological barrier, such as the BBB of an organism or the plasma membrane of a cell, and engender a sequence specific biological response. Further, the location of a base pair mismatch between a mismatch PNA oligomer and a target sequence can be anywhere along the mismatch PNA oligomer's sequence. For example, the base pair mismatch can be at the first, second, third, fourth, or up to the last base pair position along the mismatch PNA oligomer. Moreover, a mismatch PNA oligomer can have one or multiple (e.g., two, three, four, five, six, seven, and eight) base pair mismatches with respect to a target sequence.

Mismatch PNA oligomers can be used, for example, to engender a biological response less than that produced by PNA oligomers targeting the same sequence but having less or no base pair mismatches with respect to that target sequence. In other words, the sequence of a PNA oligomer can be changed such that base pair mismatches exist between the PNA oligomer and a target sequence. Introducing such changes can alter the degree of an engendered biological response that otherwise would have been engendered without the change. Typically, PNA oligomers having a greater number of mismatches with respect to their target sequences engender a biological response to a lesser degree than PNA oligomers having a lesser number of mismatches. Thus, the degree of a biological response engendered by a PNA oligomer can be modulated by changing the sequence of a PNA oligomer such that base pair mismatches exist between the PNA oligomer and a target sequence.

PNA Oligomer Kits

A kit can contain a series of different PNA oligomers. For example, a kit can contain two, three, four, five, six, seven, eight, or more PNA oligomers each having a different sequence. A kit can contain all sense PNA oligomers, all antisense PNA oligomers, or a combination of sense and antisense PNA oligomers. In addition, a kit can contain mismatch PNA oligomers. Each different PNA oligomer within a kit can have sequence specificity for the same target sequence. In this case, each oligomer of the series can contain an incrementally increasing degree of base pair mismatch with respect to the same target sequence. For example, a kit can contain a series of four PNA oligomers where one is completely complementary to a target sequence and the other three each have a sequence that creates at least one base pair mismatch with that same target sequence.

In addition, each PNA oligomer within a kit can have sequence specificity for a different target sequence. In this case, the different target sequences can be all on the same contiguous strand of nucleic acid within a cell. For example, each different PNA oligomer could have sequence specificity for a different target sequence found on the same mRNA molecule. Likewise, the different target sequences could each be part of the same region of DNA that is used as a template for synthesis of a particular mRNA.

Efficacy of PNA Oligomers

The efficacy of a particular PNA oligomer can be evaluated in vivo using a dose-response analysis. For example, an increasing concentration of a PNA oligomer can be administered to animals and the degree of responsiveness after administration measured. Evaluating the efficacy of a particular PNA oligomer can provide useful information about the potency of that PNA oligomer. In addition, concentrations that are either non-effective or at saturation can be determined. For example, a dose-response analysis can provide information about a particular PNA oligomer's efficacy in vivo as well as information about specific doses.

A dose-response analysis also can be used to evaluate individual batches or particular preparations of a PNA oligomer. For example, a dose-response analysis can be used to determine whether a particular batch of a PNA oligomer is more or less effective than another batch of the same PNA oligomer. This would allow effective and non-effective batches to be combined accordingly.

Measuring PNA Oligomers

A PNA oligomer can be detected in a biological sample collected from an animal. Specifically, a biological sample is collected from an animal and incubated with a probe such that a probe/PNA oligomer complex can form. The presence of the probe/PNA oligomer complex indicates that the PNA oligomer is within that particular biological sample.

A biological sample is any sample obtained from a living organism including, without limitation, tissue, blood, serum, urine, mucus, sweat, saliva, and stool. An animal can be a vertebrate or invertebrate animal. Vertebrate animals include mammals such as murine animals and humans.

Any appropriate manner can be used to collect a biological sample from an animal at any time before or after that animal is treated with a PNA oligomer. In addition, an animal can be perfused prior to collecting a biological sample for analysis. Once a biological sample is collected, the sample can be prepared as follows. For tissue samples such as brain, heart, kidney, liver, and spleen tissue samples, the tissue can be flash frozen and homogenized, for example, in 1 mM Tris (pH 4.0), 0.1 mM EDTA at a concentration of 1.5 ml/g wet weight of tissue. This acidic condition can protonate cytosine bases as well as the N-terminal amino group of the PNA oligomer to be detected. Such protonation can increase the solubility of a PNA oligomer and allow the PNA oligomer to separate into the aqueous phase during an extraction. In addition, a homogenized sample can be boiled for a period of time, for example, about five minutes. Boiling a sample can free any bound PNA oligomer to be detected from its target sequence, which may be within the sample. In addition, boiling a sample can inactivate nucleases that may interfere with the integrity of the probe if a the probe is sensitive to such nucleases. The sample can be spun to pellet insoluble material. For example, a sample can be spun two to three times at 35,600×g for 10 minutes each. Once spun, the supernatant can be collected and extracted to remove glycolipids that may interfere with gel electrophoresis. For example, the supernatant can be extracted with 10 volumes of $CHCl_3$:MeOH (2:1 v/v) and spun briefly at 1,000×g to separate the phases. The phase containing the PNA oligomer to be detected can be collected in a fresh tube, lyophilized, and resuspended in water (e.g., 30 to 40 µl of $H_2O$).

For a blood sample, whole blood can be collected and a buffered citrate solution added. For example, 15 µl of a 0.13 M buffered citrate solution can be added to a 150 µl whole blood sample. Then, the blood sample can be spun briefly and serum collected in a fresh tube. The serum can be diluted or used undiluted. For example, 1 µl aliquots of serum can be diluted to a final volume of 30 µl in TE buffer (pH 8.0).

A probe can be made from any type of nucleic acid or nucleic acid analog provided the probe has sequence specificity for the PNA oligomer to be detected. For example, a probe can be, without limitation, a DNA oligonucleotide probe or a PNA oligomer probe. Typically, a probe has a sequence that is fully complementary to the PNA oligomer to be detected. In other words, if a PNA oligomer to be detected has a sequence of 5'-GGGGGG-3', then a typical probe would have a sequence of 5'-CCCCCC-3'. In addition, a probe can be labeled to aid in the detection of the probe/PNA oligomer complex. For example, a probe can be labeled with biotin, digoxigenin, a radioisotope (e.g., $^3H$, $^{12}C$, $^{32}P$, $^{33}P$, $^{35}S$, and $^{125}I$), or any other molecule that enables probe detection.

To prepare a radio-labeled DNA oligonucleotide probe, a DNA oligonucleotide can be end-labeled using T4 Polynucleotide Kinase and [Gamma-$^{32}P$]ATP or [Gamma-$^{33}P$]ATP. Unincorporated nucleotides can be removed using a Chroma-Spin 10 column and the probe purified on a 20% acrylamide gel. Once separated on a gel, the probe can be excised and eluted, for example, into 100 to 150 µl of 10 mM Tris (pH 8.0), 1 mM EDTA.

The sample and the probe can be mixed together and incubated to allow the formation of a probe/PNA oligomer complex. For example, 400 pg of probe can be added to a 30 to 40 µl sample prepared as described herein. After adding the probe, the sample can be incubated at room temperature for 20 minutes.

A probe/PNA oligomer complex can be detected using any method including, without limitation, separation techniques and immunological techniques. For example, separation techniques such as gel electrophoresis or HPLC and immunological techniques such as ELISA or immunoprecipitation can be used to detect probe/PNA oligomer complexes. Briefly, separation techniques can used to detect the presence of probe containing complexes that have a molecular weight greater than that of probe alone. Immunological techniques can involve the use of an antibody having binding specificity for probe/PNA oligomer complexes and not probe alone (e.g., anti-PNA/DNA antibodies). When the method of detection involves gel electrophoresis, the assay typically is referred to as a "gel shift assay."

The methods of detecting PNA oligomers described herein also can be used to quantify the concentration of PNA oligomer within a particular biological sample. Quantification typically involves adding known amounts of a PNA oligomer to a control sample to generate a standard curve.

Modulating Polypeptide Expression

Taken together, the results presented herein demonstrate that sense, antisense, and mismatch PNA oligomers cross a biological barrier (the BBB and the plasma membrane), and engender a sequence specific biological response. In addition, these results demonstrate that sense PNA oligomers inhibit transcription and antisense PNA oligomers inhibit translation. Moreover, these results demonstrate that a very small quantity of the PNA oligomer is needed to engender a sequence specific biological response that can last for at least 24 hours. Thus, PNA oligomers can be used to treat a multitude of diseases, including those in brain previously thought to be untreatable (e.g., Huntington's disease and Alzheimer's disease).

In addition, the treatment of animals with a PNA oligomer to reduce polypeptide synthesis by inhibiting either transcription or translation can be used to create an animal that does not express a particular polypeptide for a specific period of time. Transiently knocking down polypeptide expression may provide a method for studying polypeptide function that is superior to that of current approaches involving the use of "knock-out" animals that lack a particular polypeptide during their entire lifetime, including early development. For example, knocking out polypeptide expression during an animal's entire existence may lead to compensatory mechanisms that do not accurately reflect the normal development. Transiently limiting polypeptide expression using PNA oligomers may avoid such compensatory mechanisms allowing a specific polypeptide's function to be examined during any stage of development, including adulthood.

The invention will be further described in the following examples, which do not limit the scope of the invention described in the claims.

EXAMPLES

Example 1

Extracellular Administration of PNA Oligomers Having Sequence Specificity for the Neurotensin Receptor-1

1. Synthesis of PNA Oligomers

PNA oligomers were synthesized with Fmoc-N-(2-aminoethyl) glycyl PNA monomers on an Expidite 8909 Nucleic Acid Synthesizer according to the chemistry and protocols developed by the manufacturer (PerSeptive Biosystems, Inc., Framingham, Mass.). The exocyclic amines of the bases adenine, guanine, thymine, and cytosine of each Fmoc-PNA monomer were protected with the blocking group benzhydryloxycarbonyl (Bhoc). Synthesis of the PNA oligomers (2×2 $\mu$mol) was on polyamide linker (PAL)-Polyethylene Glycol-olystyrene resin (PerSeptive Biosystems, Inc.) which produces a carboxamide group ($CONH_2$) at the COOH terminus (3') end. After synthesis, the PNA was de-protected and removed from the resin by treatment with a mixture of 80% trifluoroacetic acid (TFA) containing 20% m-Cresol for 90 minutes at 22° C. The PNA oligomer was then precipitated in diethyl ether and purified by reverse phase high performance liquid chromatography on a Vydac $C_{18}$ column at 60° C. with a buffer of 0.1% aqueous TFA and a linear gradient of 0.5% TFA containing 80% acetonitrile/20% water. A major peak (@$A_{300}$ nm) was collected, lyophilized, and verified for its correct mass weight by electro-spray ionazation mass spectrometry on a Sciex API 165B mass spectrometer (Perkin-Elmer, Foster City, Calif.).

2. Neurotensin Receptor PNA Oligomers

Neurotensin (NT) is a tridecapeptide that produces a potent, naloxone-insensitive anti-nociceptive response as well as hypothermia when injected into the periaqueductal gray (PAG) region of the rat brainstem. Currently, two subtypes of NT receptors have been identified (NTR1 and NTR2), however, their exact involvement in NT-mediated anti-nociception and hypothermia remains unclear. In an attempt to characterize NT receptors and possibly identify additional subtypes, a PNA oligomer (NTR1-PNA) having sequence specificity for NTR1 was synthesized as described above. Specifically, this NTR1-PNA was a 12-mer having an antisense sequence beginning at +103 bp from the start site of the coding region of the recombinant rat NTR1. This region was selected because it is an area thought to have high secondary structure in the mRNA. This may not be important for binding of antisense PNA oligomers, which have higher affinity for complementary nucleic acids (both RNA and DNA) than does DNA. The sequence of NTR1-PNA is 5'-CATTGCTCAAAC-3' (SEQ ID NO: 1).

3. Injecting NTR1-PNA Oligomers Intracranially

Under an Institutional Animal Care and Use Committee approved protocol and under sterile conditions male Sprague-Dawley rats (180–200 g) were stereotaxically implanted with stainless steel guide cannulae (26 gauge) into the PAG under sodium pentobarbital anesthesia (50 mg/kg, i.p.) as described in detail elsewhere (Jensen T. S. and Yaksh T. L., Brain Res. 372:301–312 (1986) and Al-Rodhan N. R. F., Brain Res. 557:227–235 (1991)). The coordinates used for PAG cannulations are −5.6 mm posterior from bregma, 1.0 mm lateral from bregma, and 5.5 mm down from the dura. The guide cannula was pre-measured to be 5.5 mm (Plastics One, Roanoke, Va.) and the internal cannula was ordered to fit below the pedestal with a 2.0 mm projection. The guide cannula was then fixed to the skull using a stainless steel screw (⅛ inch) and cranioplastic cement. A stainless steel stilette was then placed in each guide to keep it patent and free of debris. Immediately after surgery, the animals were allowed to recover before returning them to an individual housing cage. All injections began 5–7 days after surgery. If any problem, such as an infection, was observed with an animal after cannulation, then the animal was euthanized immediately by decapitation.

NTR1-PNA oligomers were injected, using a Hamilton digital syringe, into the PAG through the internal cannula, which extended 2 mm below the guide tip. The internal cannula was connected with a length of polyethylene tubing (PE-20) filled with saline solution. A small air bubble was introduced into the tubing to separate the saline from a solution containing 1.3 nmol of NTR1-PNA oligomers in artificial cerebral-spinal fluid (ACSF). The volume of the solution containing the NTR1-PNA oligomers was about 1.0 $\mu$l. The bubble was used to confirm the movement of this solution through the polyethylene tubing.

NTR1-PNA oligomers were injected into the PAG of each rat three times, on days −4, −2, and 0. Controls included rats receiving no injections, rats receiving injections of ACSF only, and rats receiving PNA oligomers having sequence specificity for an unrelated polypeptide, the mu-1 morphine receptor (MU1R). The sequence of MU1R-PNA is 5'-CAGCCTCTTCCTCT-3' (SEQ ID NO: 2).

4. Analysis of Neurotensin-mediated Biological Responses

The injection of NT in the PAG of rats produces a potent anti-nociceptive response as well as hypothermia. These responses are mediated by specific NT receptors and are not inhibited by naloxone. A very sensitive and reliable hot plate test was used to measure the anti-nociceptive effects of NT (Al-Rodhan N. R. F., Brain Res. 557:227–235 (1991)).

NTR1-PNA, MU1R-PNA, and ACSF treated as well as untreated rats were analyzed using the hot plate test for NT. One day after the last treatment, each rat was analyzed as follows. Fifteen minutes prior to testing, a pre-drug latency measurement was made by placing the rat on a hot plate maintained at a temperature of 52±0.15° C. and recording the time elapsed before the rat licked either of its hindpaws. In addition, the temperature of the rat was taken using a thermister probe inserted 3 cm in the rectum to determine the pre-drug body temperature (BT). After making these measurement, an appropriate dose of NT (18 nmol) at a volume of about 0.5 ul was administered into the PAG as described above. Thirty minutes after administering NT, the rat was again placed on a hot plate maintained at a temperature of 52±0.15° C. and the latency between the time the rat was placed on the surface and the time it licked either of its hindpaws was measured. Failure to respond in 30 seconds resulted in the removal of the rat to prevent tissue damage and the assignment of that latency. Hot plate tests were scored as the percent of maximum possible effect (% MPE) and calculated using the following equation: % MPE=[(post-drug latency−pre-drug latency)/(cut-off−pre-drug latency)]× 100; where the cut-off is 30 seconds. Untreated control rats are NT responsive and had a significant change within the 30 second time test averaging 75%±9% MPE. This average for untreated control rats was used to set the baseline MPE value to 100. Immediately after the 30 second hot plate test, BT was taken to measure NT-induced hypothermia using a thermister probe inserted 3 cm in the rectum. Again, untreated control rats are NT responsive and had a significant temperature change averaging −1.81±0.26° C., which was used to set the baseline BT value to 100. All test situations were compared to these baseline values derived from NT responsive untreated controls.

On the last day of testing, 0.5 μl of methylene blue was injected into the PAG of each rat. The rat then was decapitated and the brain removed to verify the placement of the cannula. Each brain was placed in 10% formalin/sucrose for 3 days and frozen sections (30 μm thick) were taken coronally along a plane parallel to the injection cannula. The sections were stained with Crystal violet, photographed, and compared to stereotaxic plates. The results presented were derived from rats having the correct cannula location.

Data were tested for significance by the Student's t-test with $p<0.05$ being considered significant.

FIG. 1 depicts the MPE and BT responses to NT challenge as a percent of baseline response for rats treated with NTR1-PNA oligomers as described above. Each rat received three injections of NTR1-PNA oligomers on days −4, −2, and 0. The 100 percent value on day zero was derived from untreated control rats, whereas the NTR1-PNA treated rats were first analyzed one day after the last injection on day 0. Both the NT-mediated anti-nociceptive (MPE) and hypothermia (BT) responses were significantly reduced at day one after NTR1-PNA treatment and remained significantly reduced until day five for anti-nociception and day six for hypothermia. Responsiveness to NT challenge gradually returned to normal from days five to nine. In addition, both behavioral responses were correlated having nearly identical levels of reduction, recovery, and rates of recovery.

Figure 2:
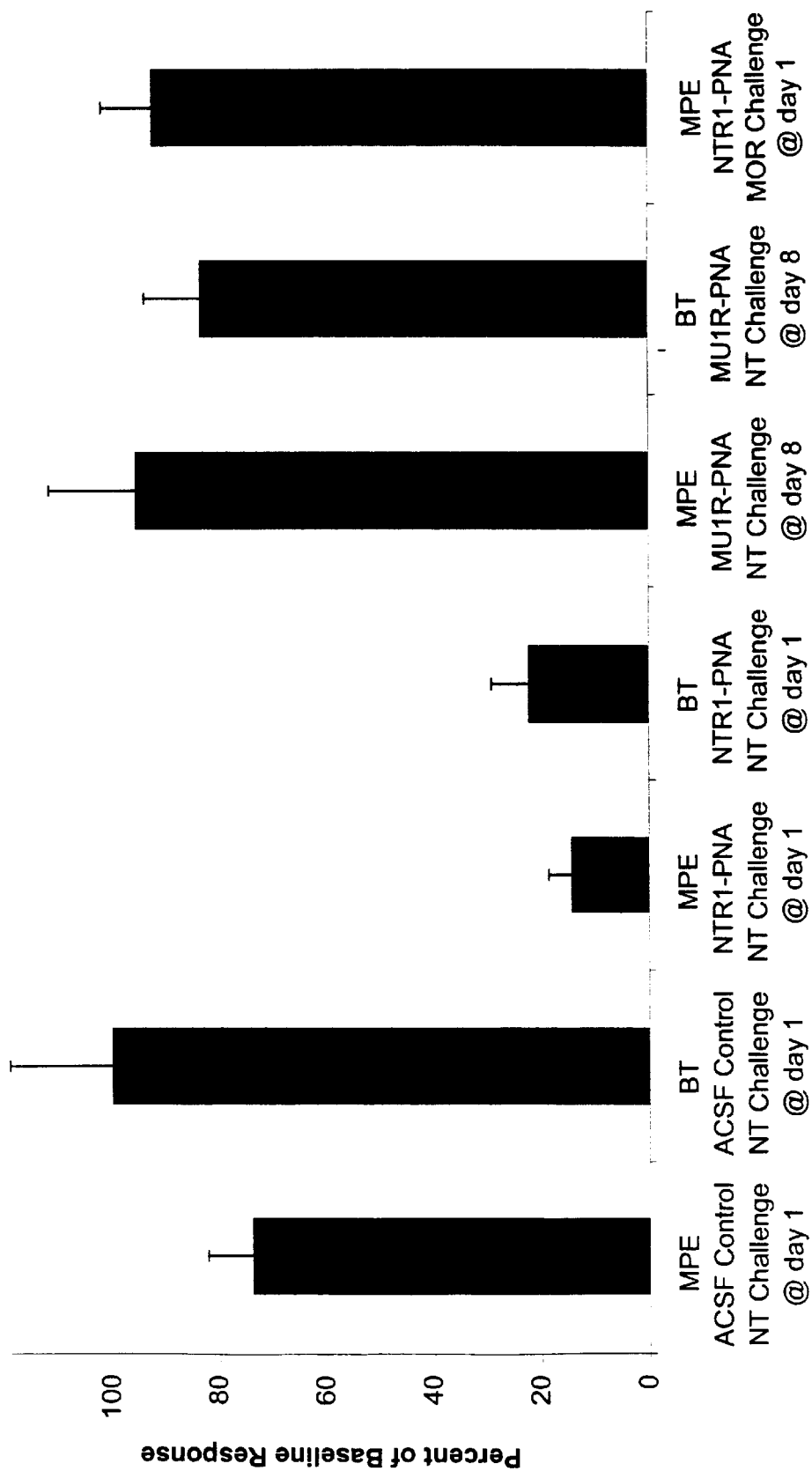
FIG. 2 is a bar graph depicting the maximal possible effect and body temperature as a percent of baseline response for rats receiving the indicated PNA oligomer treatments intracranially on days −4, −2, and 0 and challenged with either NT or morphine (MOR) on the days indicated.

FIG. 2 is a bar graph that depicts the sequence specific effects of NTR1-PNA oligomer treatment. The MPE and BT for each type of treatment was determined as a percent of baseline response by NT challenge. The MPE and BT values derived from rats injected with ACSF only and challenged with NT were equivalent to baseline responses. These animals were completely responsive to NT challenge, exhibiting little or no reaction to pain as well as a decreased body temperature. Rats injected with NTR1-PNA oligomers, however, exhibited little response to NT challenge. In fact, the MPE and BT responses to NT challenge for NTR1-PNA treated rats were 10 to 30 percent of the baseline responses. As a control to indicate the sequence specific nature of the PNA oligomer influence on these biological responses, the NT responsiveness of rats injected with MU1R-PNA oligomers was analyzed. The MPE and BT values derived from rats injected with MU1R-PNA oligomers and challenged with NT were indistinguishable from the baseline responses, indicating that the NTR1-PNA oligomers engender a biological response in a sequence specific manner. As another control, rats injected with the NTR1-PNA oligomers were analyzed for morphine (MOR) responsiveness using a tail flick assay (see Example 2 below). The MPE for rats treated with NTR1-PNA oligomers and challenged with MOR was similar to baseline response values, again indicating the specificity of the NTR1-PNA oligomers.

5. Identifying the Function of Neurotensin-1 Receptors

As stated above, two subtypes of NT receptors have been identified and additional, currently unidentified, NT receptor subtypes may exist. Further, the exact involvement of NTR1 and NTR2 in NT-mediated anti-nociception and hypothermia remains unclear. For example, NTR1 could primarily mediate anti-nociception and NTR2 could primarily mediate hypothermia or vice versa. The results described above, however, indicate that NTR1 participates significantly in both NT-mediated anti-nociception and hypothermia responses (FIGS. 1 and 2). In fact, both biological responses are correlated having nearly identical levels of reduction, recovery, and rates of recovery (FIG. 1). This identification of NTR1 function is based on the fact that the specific sequence of NTR1-PNA is not present in NTR2 and the assumption that the sequence of NTR1-PNA is unique to only NTR1 and not any other unidentified NT receptor subtypes.

6. Analysis of Neurotensin Receptors

In addition to determining the influence of NTR1-PNA oligomers on anti-nociception and hypothermia, the effects of these oligomers on NT binding sites were determined using the following NT receptor binding assay.

Binding assays were done with homogenates from rat PAG and hypothalamus tissue as described elsewhere (Kanba et al, *J. Neurochem.* 46:946–952 (1986) and Al-Rodhan N. R. F., *Brain Res.* 557:227–235 (1991)). Tissue concentrations were 1 mg wet weight per tube in a total volume of 100 μl with a final buffer concentration of 0.05 M Tris-HCl (pH 7.4) containing the following compounds to inhibit degradation of peptides: 0.02% (w/v) bovine serum albumin, 2.8 mg/ml bacitracin, 1.0 mM EDTA, 0.5 mM o-phenanthroline, 10 μg/ml pepstatin, 10 μg/ml leupeptin, 10 μg/ml aprotinin, 5 mM benzamidine, 2 mM phenylmethylsulfonylfluoride, and 50 μM bestatin. For each experiment, 80 μl of a thawed membranal suspension was incubated for 25 minutes at 20° C. in a solution containing 0.2 nM [$^{125}$I]neurotensin with a final volume of 100 μl. After incubation, the mixture was rapidly filtered to separate bound from unbound radioligand. Each filter was then dried for 2 minutes, placed on a solid scintillation sheet (Wallac Oy, Turku Finland; cat. no. 1205-441), and measured for radioactivity in a beta-plate scintillation counter (Wallac Oy; model #1205 beta plate). Non-specific binding of [$^{125}$I] neurotensin, defined as the binding in the presence of 1 μM neurotensin (~20% of total binding), was subtracted from the total binding to calculate the specific binding.

The LIGAND program was used to analyze all binding data (Munson P. J. and Rodbard D., *Analyt. Biochem.* 107:220–239 (1980)). Specifically, this program was used to calculate equilibrium dissociation constants and maximal number of binding sites.

Table I contains the results from several [$^{125}$I]neurotensin binding assays. The analysis of PAG tissue in experiment 1 was as follows. Four rats were cannulated and treated on days −4, −2, and 0 with either ACSF only or NTR1-PNA as described above. One day after the final treatment, the PAG region of the rat brain was removed, homogenized, and used in the binding assays. Rats treated with ACSF only were used to derive control values for the percent control disintegrations per minute (dpm) and percent control receptors (fmol/mg wet weight). Thus, the values for ACSF only treated rats were set to 100 percent. One day after the final treatment, the PAG region from NTR1-PNA oligomer treated rats expressed 60–70 percent fewer [$^{125}$I]neurotensin binding sites than ACSF only treated rats.

In experiment 2, five rats were untreated and used as controls, two recovered rats were treated with ACSF only, and four rats were treated with NTR1-PNA oligomers. The two rats treated with ACSF only are designated as recovered since both rats previously received a single dose of PNA oligomers intraperitoneally (one received NTR1-PNA oligomers and the other MU1R-PNA oligomers). These rats, however, were not used until five days after the intraperitoneal (i.p.) PNA oligomer treatment. Thus, at the time the binding analysis was performed, these rats were completely normal as determined by the behavioral NT-mediated responses and the MOR-mediated response described above. Again, one day after the final treatment, the PAG region from NTR1-PNA oligomer treated rats expressed fewer [$^{125}$I]neurotensin binding sites than both the recovered ACSF only treated rats and untreated control rats. In this experiment, the reduction in binding sites was about 20–30 percent of those expressed by the untreated rats. Further, the previously treated recovered rats that received ACSF only expressed significantly more NT binding sites than the untreated control rats, possibly indicating the involvement of a compensatory mechanism operating at the level of receptor densities.

NT binding sites from the hypothalamus region of the rat brain were also analyzed. In this experiment, the hypothalamus region of rat brain was removed from the same rats used in experiment 2 to analyze the PAG region (five untreated control rats, two recovered ACSF only treated rats, and four NTR1-PNA oligomer treated rats). The untreated rats were used to derive control values. One day after the final treatment, the hypothalamus region from NTR1-PNA oligomer treated rats expressed 40–50 percent fewer [$^{125}$I] neurotensin binding sites than untreated control rats. In addition to indicating that extracellularly administered PNA oligomers influence the expression of specific polypeptide, these results demonstrate that PNA oligomers injected into the PAG diffuse through brain tissue to the hypothalamus since the NTR1-PNA oligomers were injected into the PAG and not the hypothalamus.

TABLE I

[$^{125}$I]neurotensin binding sites from rats 6 days after chronic treatment with NTR1-PNA oligomers.

| PAG Tissue | n | % Control dpm's | % Control receptors |
|---|---|---|---|
| Experiment 1: | | | |
| ACSF Only | 2 | 100 | 100 |
| NTR1-PNA | 2 | 41 | 32 |
| Experiment 2: | | | |
| Untreated Control | 5 | 100 | 100 |
| Recovered* | 2 | 160 | 137 |
| NTR1-PNA | 4 | 81 | 67 |
| Hypothalamus Tissue | | | |
| Untreated Control | 5 | 100 | 100 |
| Recovered* | 2 | 136 | 101 |
| NTR1-PNA | 4 | 55 | 51 |

*Two previously treated rats, one treated intraperitoneally with NTR1-PNA and another with MU1R-PNA, were characterized behaviorally as fully recovered and normal.

7. Injecting NTR1-PNA Oligomers Extracranially

Figure 3:
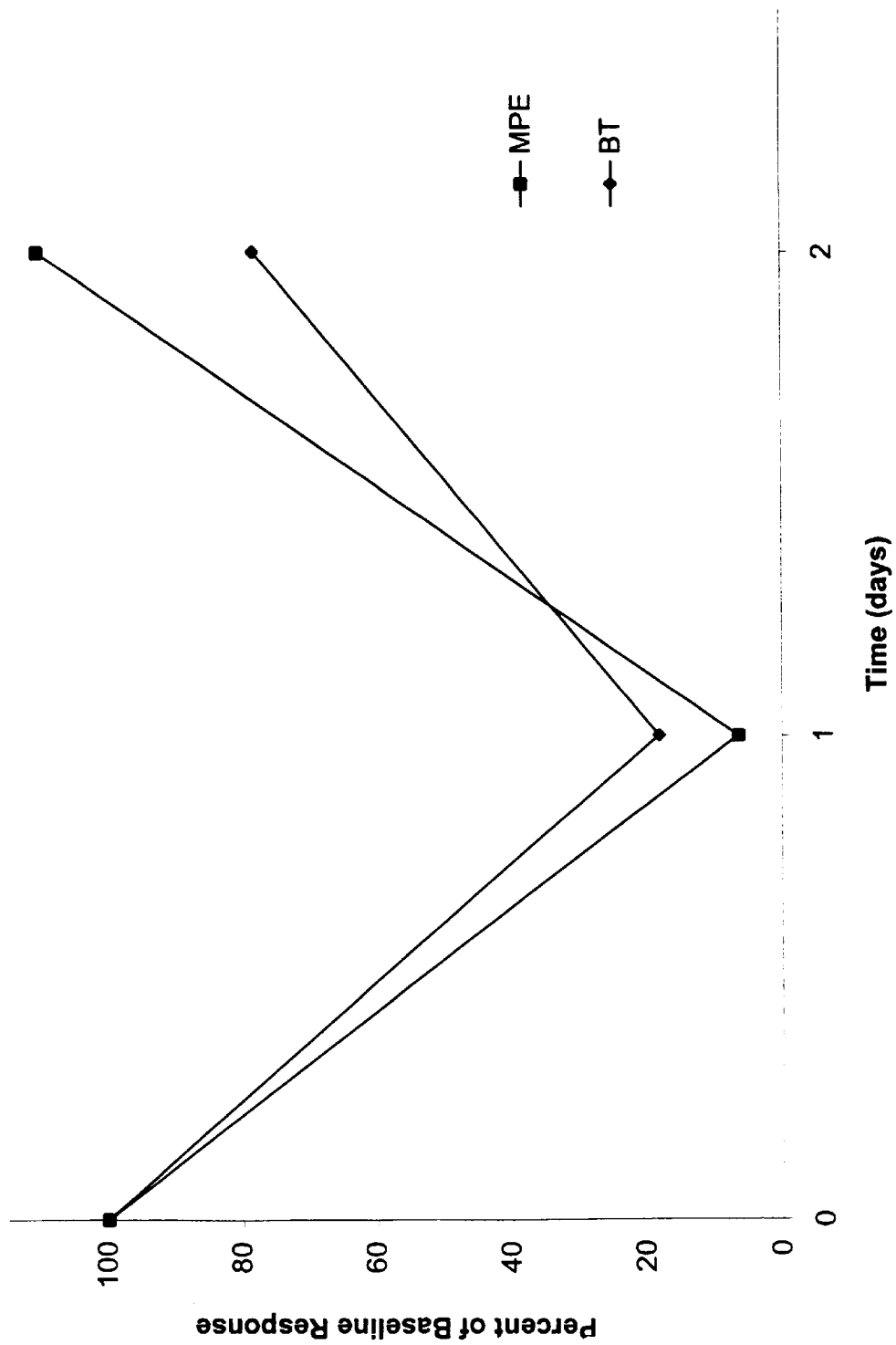
FIG. 3 is a graph plotting the maximal possible effect and body temperature as a percent of baseline response for rats treated extracranially on day 0 with NTR1-PNA oligomers and challenged with NT.
Figure 4:
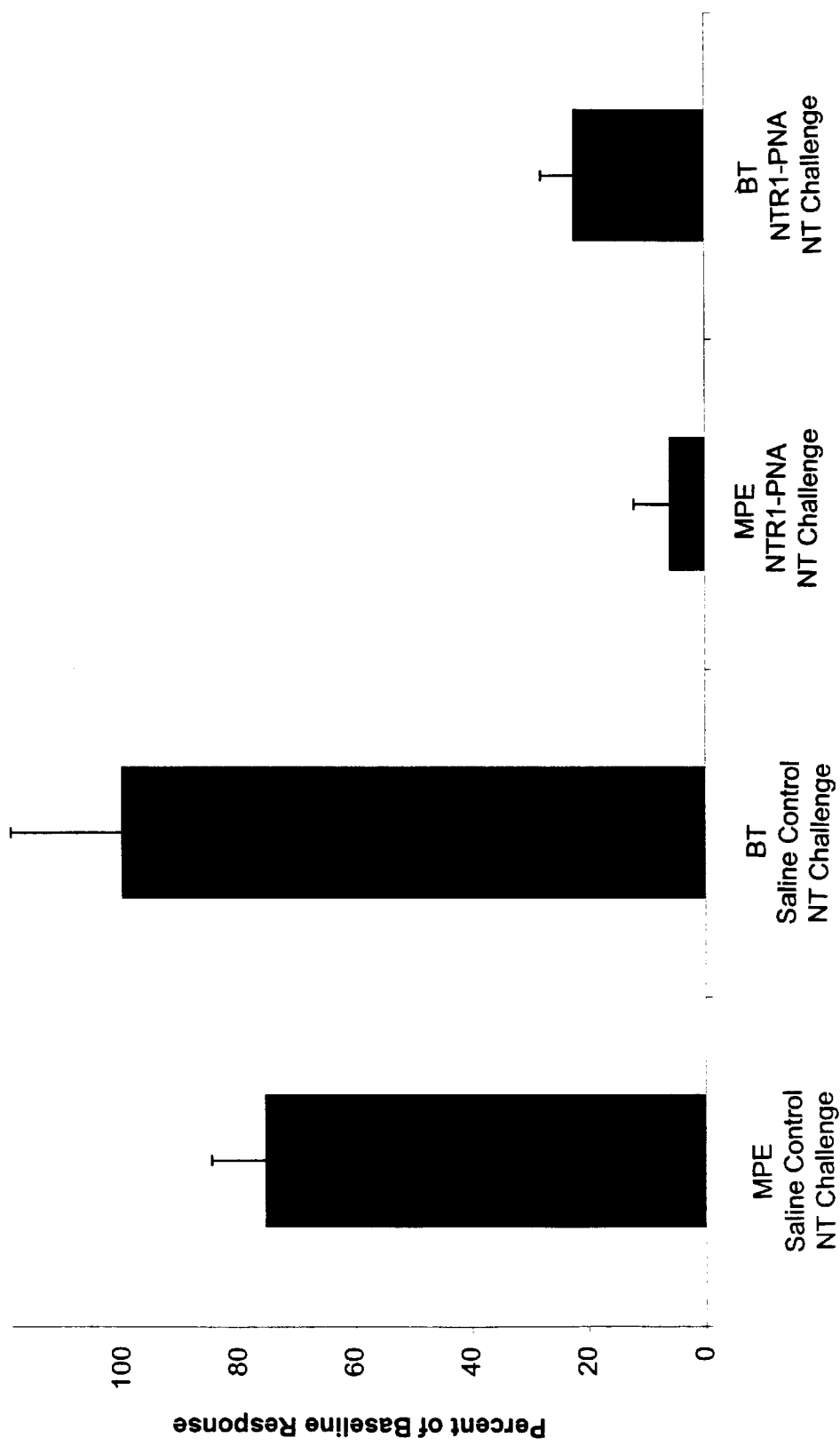
FIG. 4 is a bar graph depicting the maximal possible effect and body temperature as a percent of baseline response for rats receiving either a NTR1-PNA oligomer or saline treatment extracranially on day 0 and challenged with NT on day 1.

A solution containing 3 mg/kg of body weight of NTR1-PNA oligomers in saline was injected directly into the peritoneal cavity of male Sprague-Dawley rats (200–250 g). Each rat received a single injection on day zero and the volume injected was about 200 μl. Controls included rats receiving no injections and injections of saline only. Each day after the injection, the rats were analyzed for NT-mediated anti-nociceptive and hypothermia responses. FIG. 3 depicts the MPE and BT as a percent of baseline response for NT challenge. Baseline responses were measured from control animals not receiving injections and set to 100. Rats, however, were surgically cannulated to enable NT administration. One day after treatment with NTR1-PNA oligomers, rats were unable to respond to NT challenge. This inability to respond to NT challenge was identical to the inability observed from the PAG injections and is attributed to a reduction in NT receptors. In addition, FIG. 4 depicts the MPE and BT as a percent of baseline responses for NTR1-PNA treated, NT challenged rats as well as saline only treated, NT challenged rats at day 1. Only rats treated with NTR1-PNA oligomers exhibited a lack of NT responsiveness as determined by NT-mediated anti-nociception and hypothermia responses. Thus, NTR1-PNA oligomers administered extracranially were able to cross the BBB and the plasma membrane of cells to specifically influence the expression and thus the function of NT receptors in brain.

8. Analysis of Neurotensin Receptors Outside Brain

In addition to determining the influence of extracranially administered NTR1-PNA oligomers on anti-nociception and hypothermia, the effects of these oligomers on NT binding sites outside the central nervous system were determined.

Binding assays were performed using procedures similar to those described elsewhere (Kitabgi P. et al., *Peptides* 5:917–923 (1984) and Ahmad S. et a., *Biochim et Biophys Acta* 896:224–238 (1987)).

Table II contains the results from an [$^{125}$I]neurotensin binding assay using small intestine (jejunum and ileum) membranal preparations from NTR1-PNA treated and untreated rats. The small intestine tissue was harvested from the rats 1 day after receiving a single i.p. injection of NTR1-PNA oligomers as described above. Untreated rats were used to derive control values for the percent control dpm and percent control receptors (fmol/mg). Thus, the values for untreated rats were set to 100 percent. One day after treatment, the small intestine tissue from NTR1-PNA treated rats expressed 98 percent fewer [$^{125}$I]neurotensin binding sites than untreated rats, indicating that NTR1-PNA oligomers administered extracranially engender a biological response in both brain and the periphery (small intestine cells). These results indicate that the extracranial administration of PNA oligomers can engender a sequence specific biological response systemically.

TABLE II

[$^{125}$I]neurotensin binding sites from rats 1 day after i.p. treatment with NTR1-PNA oligomers.

| Small Intestine | n | % Control dpm's | % Control receptors |
|---|---|---|---|
| Untreated Control | 2 | 100 | 100 |
| NTR1-PNA | 1 | 41 | 2 |

Example 2

Extracellular Administration of PNA Oligomers Having Sequence Specificity for the mu-1 Receptor 1. Morphine Receptor PNA Oligomer Synthesis and Intracranial Administration Morphine (MOR) produces a potent, naloxone-sensitive anti-nociceptive response in animals. This anti-nociceptive response is mediated by MOR receptors. PNA oligomers having sequence specificity for the mu-1 receptor (MU1R-PNA) were designed and synthesized as described above. The MU1R-PNA oligomers are 14-mers having an antisense sequence corresponding to approximately –50 bp from the start site of the coding region of the recombinant mu-1 receptor. Thus, the MU1R-PNA does not have sequence specificity for the coding region of the mu-1 receptor gene, but does have sequence specificity for an upstream sequence presumed to be involved in regulating the expression of mu-1 receptors. In addition, this region is not predicted to have a high degree of secondary structure at the mRNA level. The sequence of MU1R-PNA is 5'-CAGCCTCTTCCTCT-3' (SEQ ID NO: 2). MU1R-PNA oligomers were injected into the PAG region of cannulated rats as described above.

2. Analysis of Morphine-mediated Biological Responses

The injection of MOR into rats produces a potent anti-nociceptive response. This response is mediated by specific MOR receptors and is inhibited by naloxone. A very sensitive and reliable tail flick test was devised and used to measure the anti-nociceptive effects of MOR (D'Amour F. E. and Smith D. L, *J. Pharm. Exp. Therap.* 72:74–79 (1941)).

MU1R-PNA, NTR1-PNA, and ACSF treated as well as untreated rats were analyzed using the MOR-specific tail flick test. One day after the last treatment, each rat was analyzed as follows. Thirty minutes prior to testing, a pre-drug latency measurement was made by placing the tail of the restrained rat in oil maintained at a temperature of 60° C. and recording the time elapsed before the rat flicked its tail. After making this measurement, an appropriate dose of MOR (5 mg/kg of body weight) at a volume of about 200 $\mu$l was injected i.p. Thirty minutes after administering MOR, the restrained rat's tail was again placed in the oil maintained at 60° C. and the latency between the time the tail was placed in the oil and the time the rat flicked its tail was measured. Failure to respond in 12 seconds resulted in the removal of the rat's tail to prevent tissue damage and the assignment of that latency. Tail flick tests were scored as the percent of MPE and calculated using the following equation: % MPE=[(post-drug latency−pre-drug latency)/(cut-off−pre-drug latency)]×100; where the cut-off is 12 seconds. Untreated control rats are MOR responsive and had a significant change within the 12 second time test averaging 86%±5.2% MPE. This average for untreated control rats was used to set the baseline MPE value to 100. All test situations were compared to this baseline response value derived from MOR responsive untreated controls. To test the significance, data were analyzed using the Student's t-test with p<0.05 being considered significant.

Figure 5:
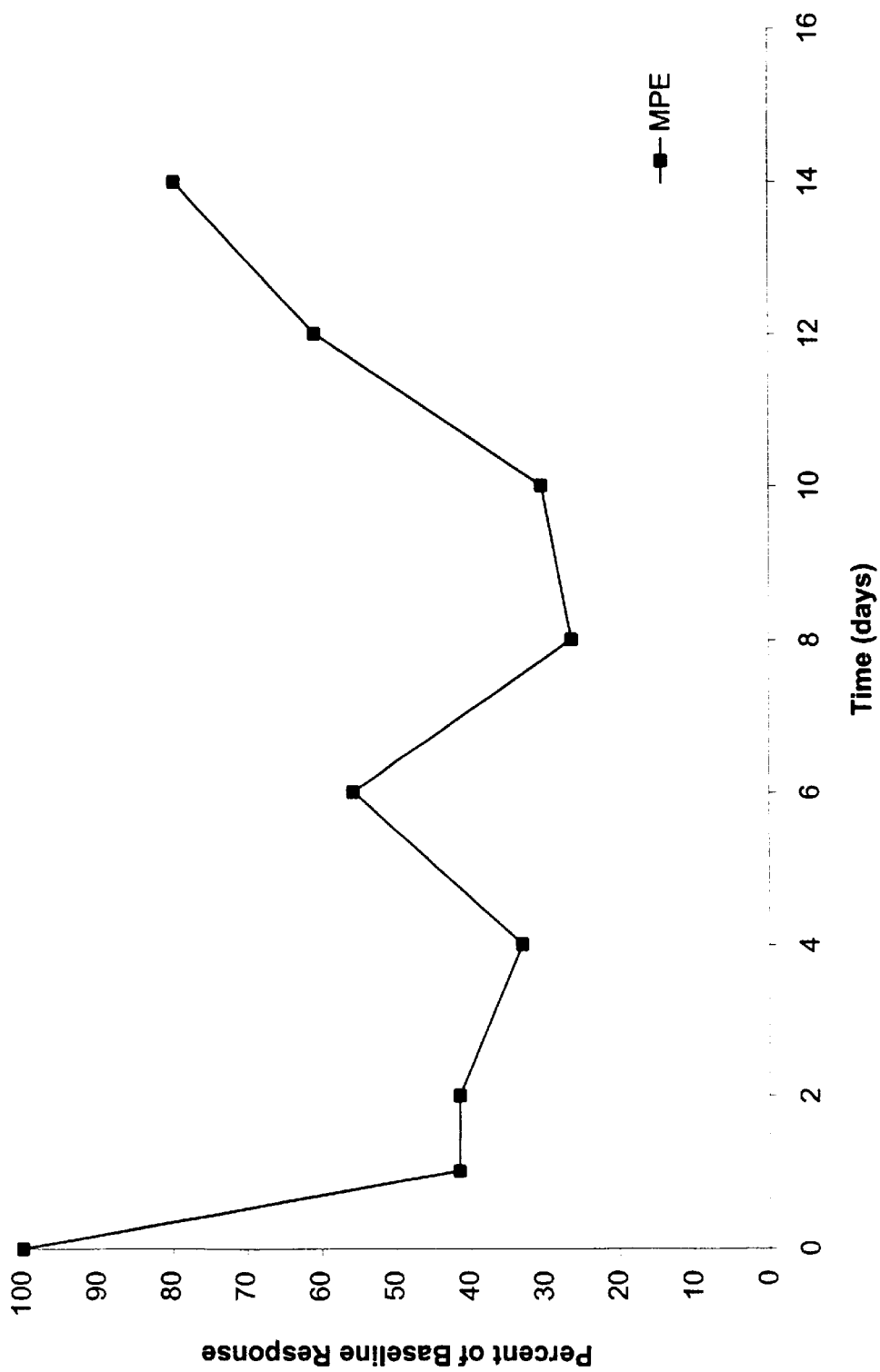
FIG. 5 is a graph plotting the maximal possible effect as a percent of baseline response for rats treated intracranially on days −4, −2, and 0 with MU1R-PNA oligomers and challenged with MOR.

FIG. 5 depicts the MPE response to MOR challenge as a percent of baseline response for rats treated with MU1R-PNA oligomers as described above. Each rat received three injections of MU1R-PNA oligomers on days −4, −2, and 0. The 100 percent value on day zero was derived from untreated control rats, whereas the MU1R-PNA treated rats were first analyzed one day after the last injection on day 0. The MOR-mediated anti-nociceptive response was significantly reduced at day one after MU1R-PNA treatment and remained significantly reduced until day twelve. Responsiveness to MOR challenge gradually returned to normal after day twelve.

Figure 6:
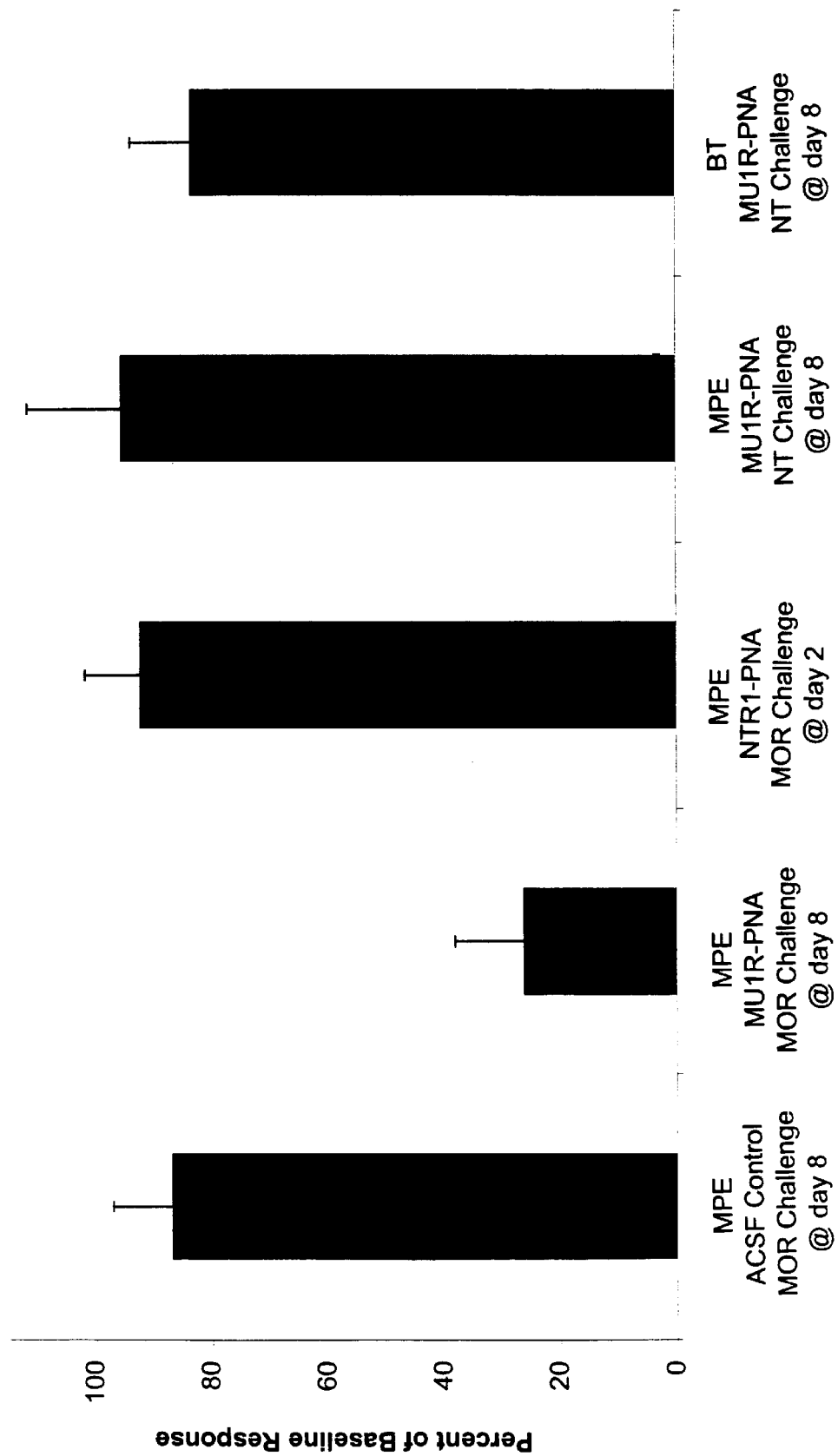
FIG. 6 is a bar graph depicting the maximal possible effect and body temperature as a percent of baseline response for rats receiving the indicated PNA oligomer treatments intracranially on days −4, −2, and 0 and challenged with either NT or MOR on the days indicated.

FIG. 6 is a bar graph that depicts the sequence specific effect of MU1R-PNA oligomer treatment. The MPE response to MOR challenge as a percent of baseline response was determined for each type of treatment. The MPE values derived from rats injected with ACSF only and challenged with MOR were equivalent to baseline responses. These animals were completely responsive to MOR challenge, exhibiting no reaction to pain. Rats injected with MU1R-PNA oligomers, however, exhibited little response to MOR challenge. In fact, the tail flick response to MOR challenge for MU1R-PNA treated rats was 20 to 40 percent of baseline response. As a control to indicate the sequence specific nature of the PNA oligomer influence on this biological response, the MOR responsiveness of rats injected with NTR1-PNA oligomers was analyzed. The MPE values derived from rats injected with NTR1-PNA oligomers and challenged with MOR were indistinguishable from baseline responses, indicating that the MU1R-PNA oligomers engender a biological response in a sequence specific manner. As another control, rats injected with the MU1R-PNA oligomers were analyzed for NT responsiveness using the hot plate test described above as well as measuring hypothermia. The MPE and BT responses for rats treated with MU1R-PNA oligomers and challenged with NT were similar to baseline response values, again indicating the specificity of MU1R-PNA oligomers.

3. Injecting MU1R-PNA Oligomers Extracranially

Figure 7:
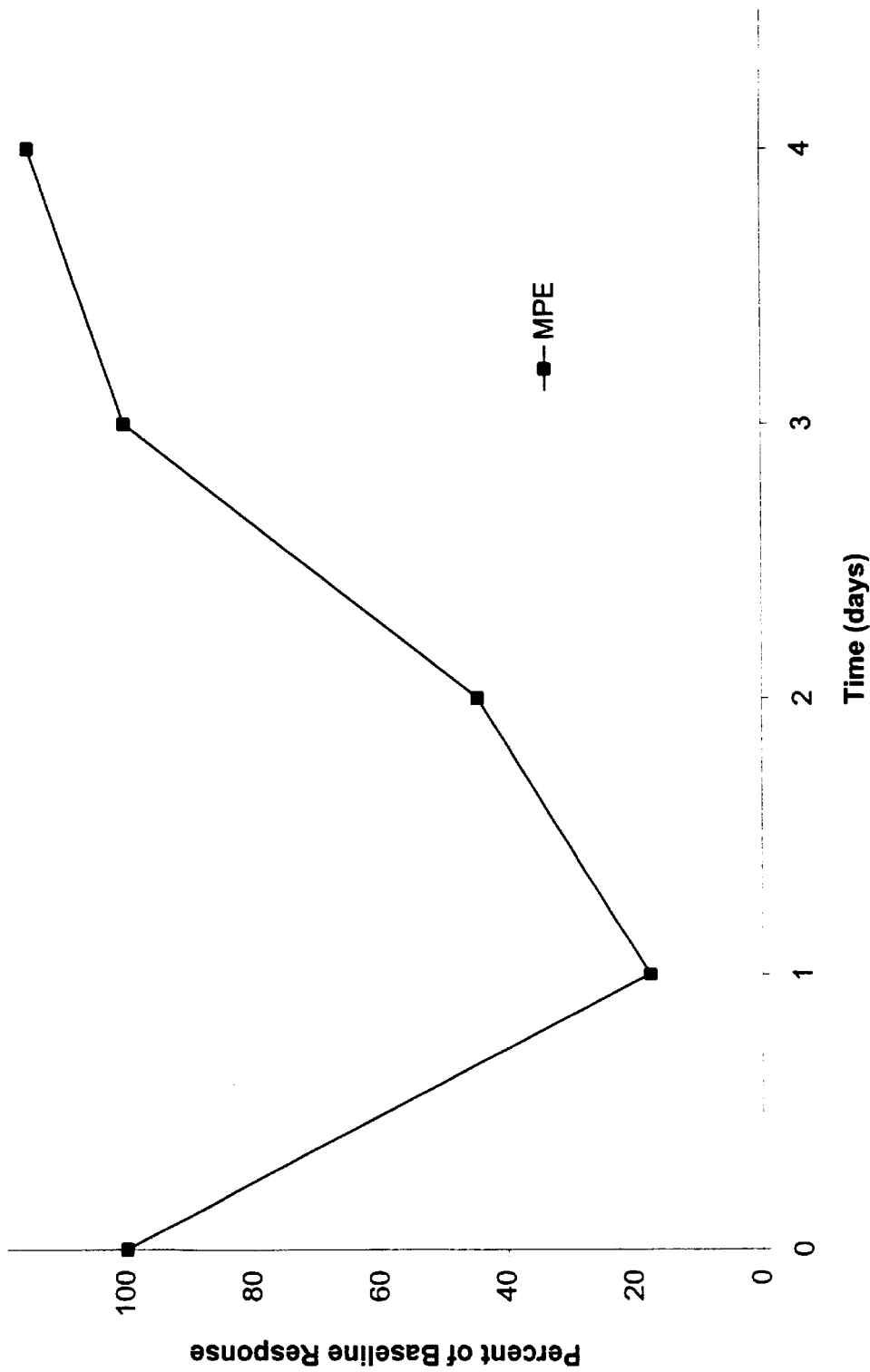
FIG. 7 is a graph plotting the maximal possible effect as a percent of baseline response for rats treated extracranially on day 0 with MU1R-PNA oligomers and challenged with MOR.
Figure 8:
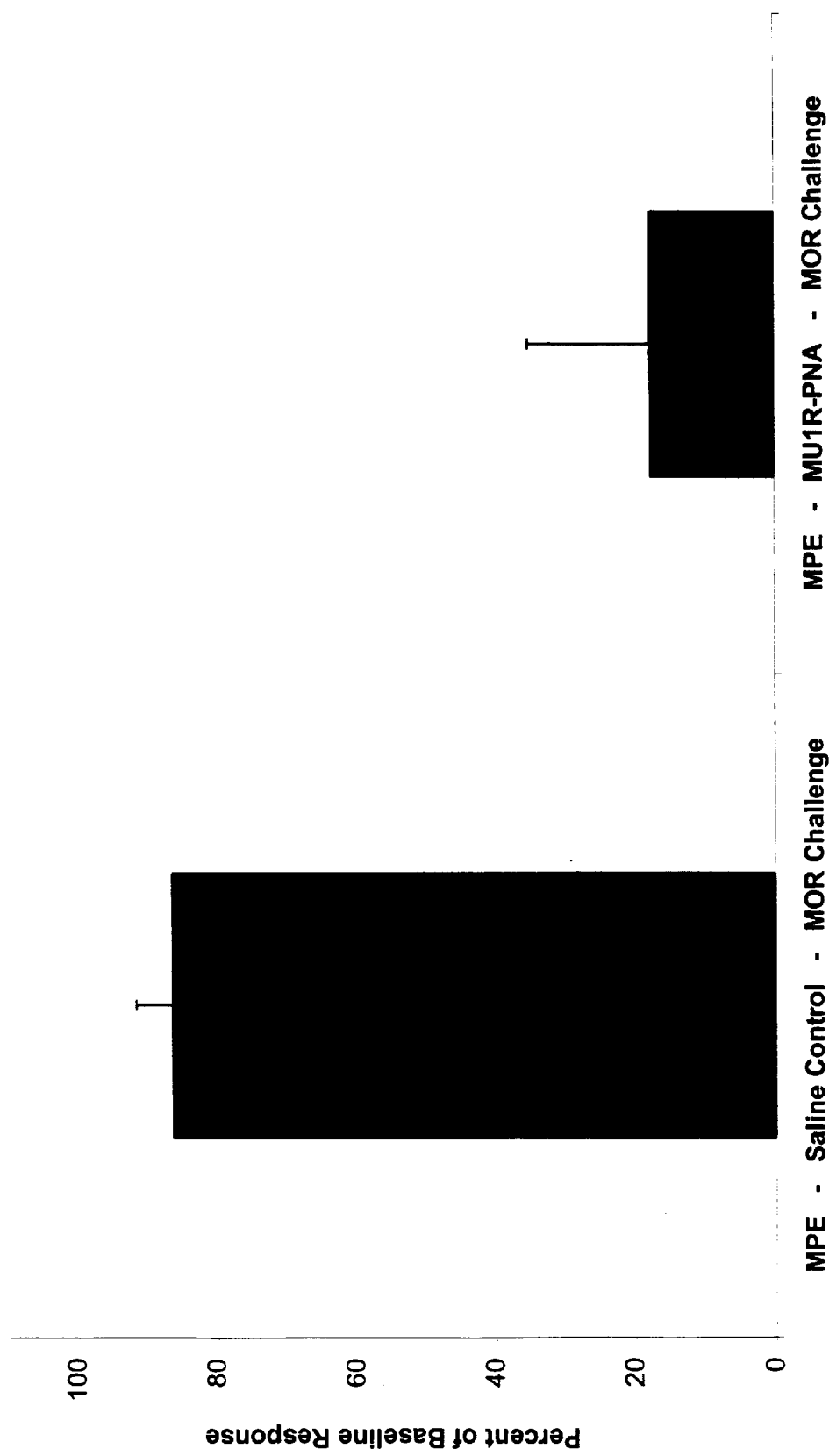
FIG. 8 is a bar graph depicting the maximal possible effect as a percent of baseline response for rats receiving either a MU1R-PNA oligomer or saline treatment extracranially on day 0 and challenged with MOR on day 1.

A solution containing 3 mg/kg of body weight of MU1R-PNA oligomers in saline was injected directly into the peritoneal cavity of male Sprague-Dawley rats (200–250 g). Each rat received a single injection on day zero and the volume injected was about 200 $\mu$l. Controls included rats receiving no injections and injections of saline only. Each day after the injection, the rats were analyzed for MOR-mediated anti-nociception. FIG. 7 depicts the MPE response to MOR challenge as a percent of baseline response. Baseline responses were measured from control animals not receiving injections and set to 100. One day after treatment with MU1R-PNA oligomers, rats were unable to respond to MOR challenge. This inability to respond to MOR challenge was identical to the inability observed from the PAG injections and is attributed to a reduction in mu-1 receptors. In addition, FIG. 8 depicts the MPE response to MOR challenge for MU1R-PNA treated rats as well as rats treated with only saline at day 1. Only rats treated with MU1R-PNA oligomers exhibited a lack of MOR responsiveness as determined by the tail flick anti-nociceptive response to MOR. Thus, MU1R-PNA oligomers administered extracranially were able to cross the BBB and the plasma membrane of cells to specifically influence the expression and thus the function of mu-1 receptors in a sequence specific manner in brain.

4. Determining the Relative Turn-over Rate for Neurotensin-1 and mu-1 Receptors

Figure 9:
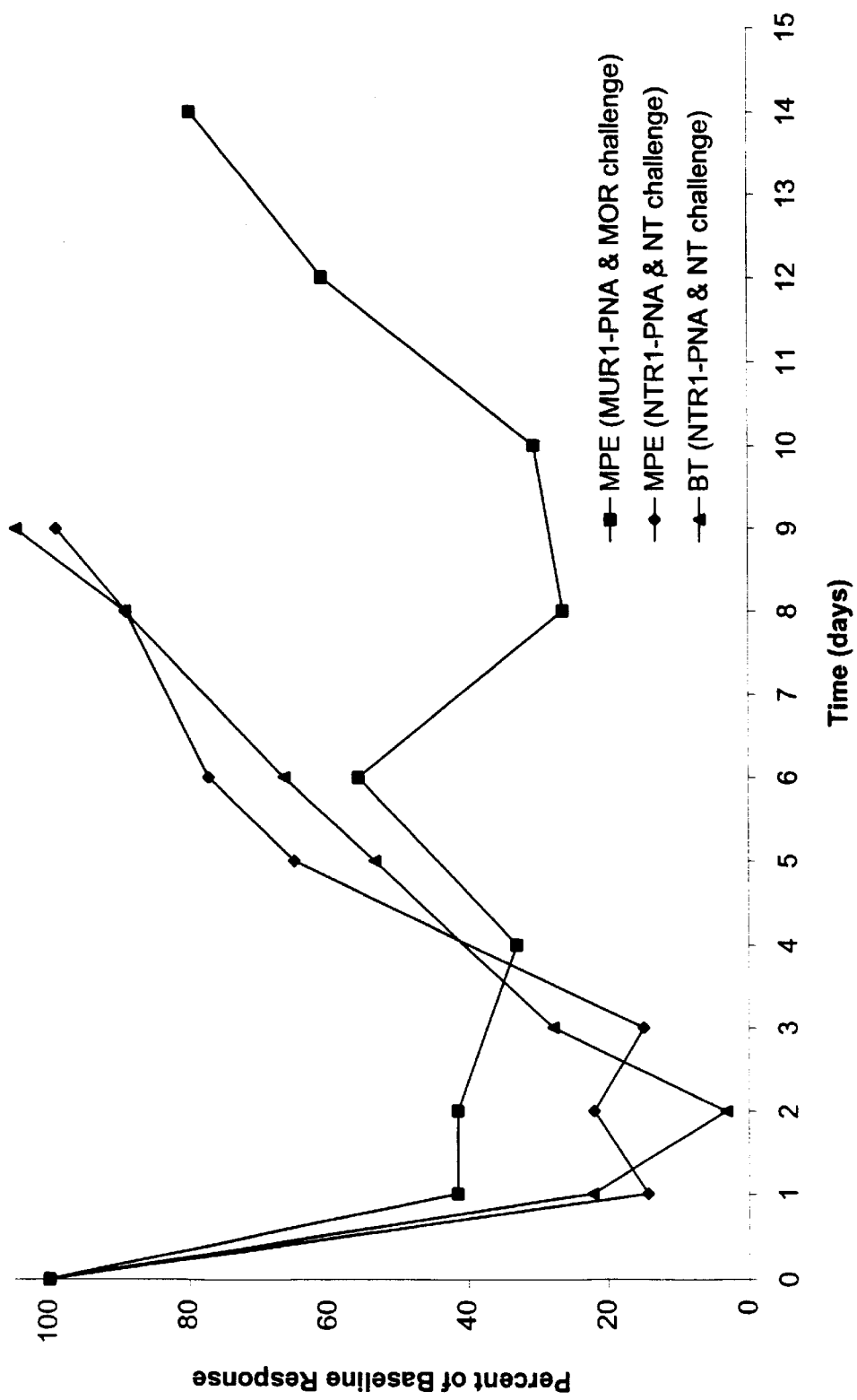
FIG. 9 is a graph plotting the maximal possible effect and body temperature as a percent of baseline response for rats treated intracranially on days −4, −2, and 0 with the indicated PNA oligomers and challenged with either NT or MOR.

To determine the relative turn-over rate of functional NTR1 and mu-1 receptors, a comparison was made between the biological responses influenced in rats by the administration of NTR1-PNA and MU1R-PNA oligomers. The MPE (hot plate) and BT responses for rats treated with NTR1-PNA oligomers and challenged with NT were compared to the MPE (tail flick) response for rats treated with MU1R-PNA oligomers and challenged with MOR (FIG. 9). Each rat received three injections into the PAG of either NTR1-PNA or MU1R-PNA oligomers on days −4, −2, and 0. The 100 percent values on day zero were derived from untreated control rats, whereas the NTR1-PNA and MU1R-PNA treated rats were first analyzed one day after the last injection on day 0. Since the time needed for MOR responsiveness to return to normal is greater than the time needed for NT responsiveness to return to normal, mu-1 receptors appear to have a slower relative turn-over rate.

Example 3

Extracellular Administration of PNA Oligomers Having Sequence Specificity for the Plasma Membrane Serotonin Transporter 1. Serotonin Transporter PNA Oligomers PNA oligomers having sequence specificity for the rat plasma membrane serotonin transporter (SERT-PNA) were designed and synthesized by manual procedures as described herein. The SERT-PNA oligomers are 12-mers having an antisense sequence corresponding to approximately 310 bp downstream from the start site of the coding region of the recombinant plasma membrane serotonin transporter. In addition, this region is predicted to have a high degree of secondary structure at the mRNA level. The sequence of SERT-PNA is 5'-GCCAGATGTTGC-3' (SEQ ID NO: 3).

2. Injecting SERT-PNA Oligomers Extracranially and Analyzing Serotonin Transport Serotonin (5-hydroxytryptamine; 5-HT) is a monoamine neurotransmitter that is packaged into vesicular compartments so that its release into the synapse can be regulated. Once released, serotonin can bind to its post-synaptic and pre-synaptic receptors. It can then be transported back into the pre-synaptic neuron by plasma membrane serotonin transporters. Within the nerve ending, serotonin can be repackaged for later release or degraded by monoamine oxidase (MAO) into its metabolite, 5-hydroxyindole-3-acetic acid (5-HIAA) Thus, serotonin rarely accumulates in the synaptic cleft and the high fidelity of chemical signaling mechanisms is maintained. Extraneuronal excess of serotonin, however, can be brought about by administering drugs that prevent either serotonin breakdown, such as a MAO inhibitor, or serotonin re-uptake such as fluoxetine. In rats, the administration of these drugs results in stereotyped hyperactivity. Other features of excess serotonin in rats include hind limb abduction, lateral head weaving, tremors, rigidity, Straub tail, hyperreactivity, piloerection, and salivation. Wet dog shakes, compulsive circling, and ataxia of hind legs have also been noted. The combination of antidepressant drugs, such as a MAO inhibitor with a plasma membrane serotonin transport inhibitor, results in a potentially fatal outcome, named "serotonergic syndrome."

To test the ability of SERT-PNA oligomers to engender a biological response, e.g., a reduction of plasma membrane serotonin transporter expression, SERT-PNA oligomers were administered to rats with and without tranylcypromine (TCP), a MAO inhibitor. The combination would be like combining a serotonin-selective re-uptake inhibitor (SSRI) such as fluoxetine with a MAO inhibitor, causing an excess of extraneuronal serotonin and leading to readily measurable behavioral consequences such as hyperactivity and the serotonergic syndrome. Thus, any results observed for rats receiving SERT-PNA oligomers plus TCP that are similar to results observed for rats treated with fluoxetine plus TCP would indicate that the SERT-PNA oligomers specifically reduced serotonin re-uptake by reducing the expression of the plasma membrane serotonin transporter.

A solution containing 5 mg/kg of SERT-PNA oligomers in saline was injected directly into the peritoneal cavity of male Sprague-Dawley rats (200–250 g). Each rat received a single injection on day zero and the volume injected was about 200 µl. Controls included rats receiving injections of saline only and injections of TCP only.

To monitor hyperactivity, an Opto-Varimex-Minor activity chamber (Columbus Instruments, Columbus, Ohio) was used. Briefly, this activity chamber records the number of times an animal disrupts an infrared beam while in a 42 cm by 42 cm chamber. Other signs of hyperactivity were noted by gross observation.

As a positive control, previously untreated rats were injected intraperitoneally with 15 mg/kg TCP followed by, 30 minutes later, 10 mg/kg fluoxetine (n=2), and monitored. Typically, these rats exhibited extreme hyperactivity within 60 minutes of fluoxetine treatment. Rats (n=3) injected intraperitoneally with 5 mg/kg of SERT-PNA oligomers and then injected with 15 mg/kg TCP 48 hours later also exhibited extreme hyperactivity within 10 minutes of TCP treatment. In addition, these rats exhibited head weaving, forepaw padding, body tremors, moving in circles, wet dog shakes, hyperreactivity, and hind limb ataxia. Thus, the combination treatment of SERT-PNA plus TCP results in a biological response equivalent to the biological response observed after the fluoxetine plus TCP treatment.

Figure 10:
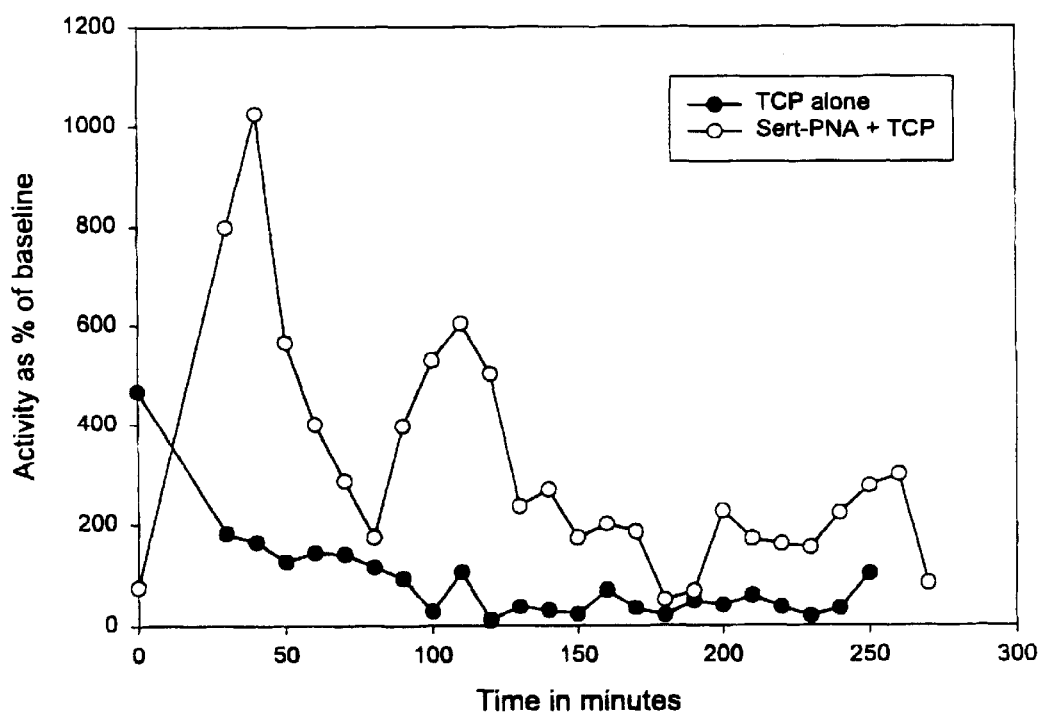
FIG. 10 is a graph plotting the activity as a percent of baseline for rats treated extracranially with SERT-PNA oligomers and challenged with tranylcypromine (TCP) 48 hours later.

The control rats, rats treated with 15 mg/kg TCP only, did not exhibit the extreme hyperactivity observed in either the TCP plus fluoxetine- or SERT-PNA oligomer plus TCP-treated rats. The TCP only-treated animals, however, did exhibit a brief period of hyperactivity. The level of this TCP only-induced hyperactivity was substantially and consistently less than the hyperactivity levels observed in the positive controls. FIG. 10 is a graph from one representative experiment depicting the rapid increase over basal activity for animals pretreated with SERT-PNA oligomers, then given TCP. The basal activity was determined by monitoring the animal, after a 60 minute habituation period, for 30 minutes prior to administration. Animals treated with TCP alone initially exhibited a slight increase in activity that quickly dissipated. In addition, these animals only exhibited head-weaving and increased salivation and none of the other behavioral signs attributed to serotonin excess. Taken together, these results indicate that the expression of the plasma membrane serotonin transporter was reduced by extracranial administration of antisense PNA oligomers to this polypeptide.

Example 4

Oral Administration of PNA Oligomers Having Sequence Specificity for the Neurotensin Receptor-1

1. Administering NTR1-PNA Oligomers Orally

Figure 11:
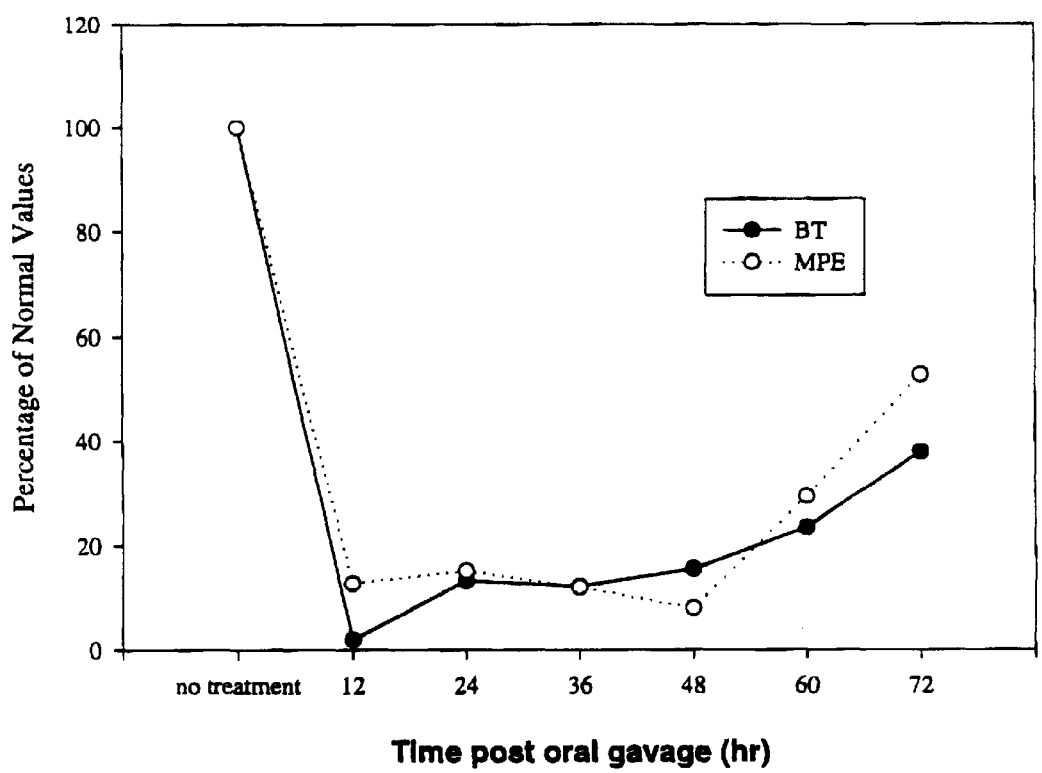
FIG. 11 is a graph plotting maximal possible effect and body temperature as a percent of baseline response for rats receiving a single oral administration of NTR1-PNA oligomers and challenged with NT at the times indicated.

Nine rats, with surgically implanted brain cannulae as described in Example 1, were given 10 mg/kg of NTR1-PNA oligomers by gastric intubation. Briefly, a feeding tube was placed into the stomach through the mouth and 500 µl of NTR1-PNA oligomers in saline administered. Twelve hours later, each rat received an injection of NT directly into the brain and was tested for hypothermic and anti-nociceptive responses to NT, as described in Example 1. The responses to NT were either completely abolished (8/9) or nearly completely abolished (1/9) in these animals. FIG. 11 depicts the MPE and BT responses to NT challenge as a percent of baseline response for rats treated orally with NTR1-PNA oligomers. Twelve hours after receiving a single oral administration of NTR1-PNA oligomers, the rats completely failed to respond to NT challenge (p<0.05 for MPE; p<0.001 BT). This complete lack of NT responsiveness remained for at least 48 hours after the single oral NTR1-PNA oligomer treatment.

These animals were sacrificed and their brains and intestinal tissue removed for NT binding site analysis.

2. Analysis of Neurotensin Receptors

In addition to determining the influence of orally administered NTR1-PNA oligomers on anti-nociception and hypothermia, the effects of these oligomers on NT binding sites were determined using the NT receptor binding assay described in Example 1.

TABLE III

[$^{125}$I]neurotensin binding sites from rats 24 hours after a single oral administration of NTR1-PNA oligomers.

| Tissue | n | NT responsiveness | number of receptors (mean ± SEM in fmol/mg wet wt.) | percent of control | $K_D$ (mean ± SEM in nM) |
|---|---|---|---|---|---|
| PAG | | | | | |
| Control | 5 | YES | 290 ± 9 | 100 | 9.0 ± 0.3 |
| NTR1-PNA | 5 | LOST | 140 ± 20 | 48 | 8.2 ± 0.7 |
| Hypothalamus | | | | | |
| Control | 3 | YES | 470 ± 7 | 100 | 8 ± 1 |
| NTR1-PNA | 5 | LOST | 240 ± 30 | 51 | 7.0 ± 0.8 |
| Small Intestine | | | | | |
| Control | 3 | YES | 16 ± 2 | 100 | 4.2 ± 0.6 |
| NTR1-PNA | 5 | LOST | Below Detection (BD) | BD | BD |

Table III contains the results from several [$^{125}$I] neurotensin binding assays performed using PAG, hypothalamus, and small intestine tissue from the same rats examined behaviorally after oral treatment with NTR1-PNA oligomers. The expression of NT binding sites in PAG, hypothalamus, and small intestine tissue was dramatically reduced 24 hours after the oral administration of 10 mg/kg of NTR1-PNA oligomers. In fact, 50 percent of the NT binding sites were reduced in PAG and hypothalamus, whereas the NT binding sites in the small intestine were completely abolished. The NT binding affinities for each test condition were statistically equivalent, indicating that reduced number of NT binding sites are not the result of an experimental artifact associated with the binding assays or a lack of activity by the NT binding sites present. Further, the addition of excess NTR1-PNA oligomers to brain homogenates used in binding assays did not change these results, indicating that the mere presence of PNA oligomers does not affect binding assays. Interestingly, the oral administration of 10 mg/kg of NTR1-PNA oligomers reduced NT binding sites in the PAG and hypothalamus to a greater extent than the intraperitoneal administration of 3 mg/kg of the same PNA oligomer (See Example 1).

Example 5

Manual Synthesis of PNA Oligomers

Figure 13:
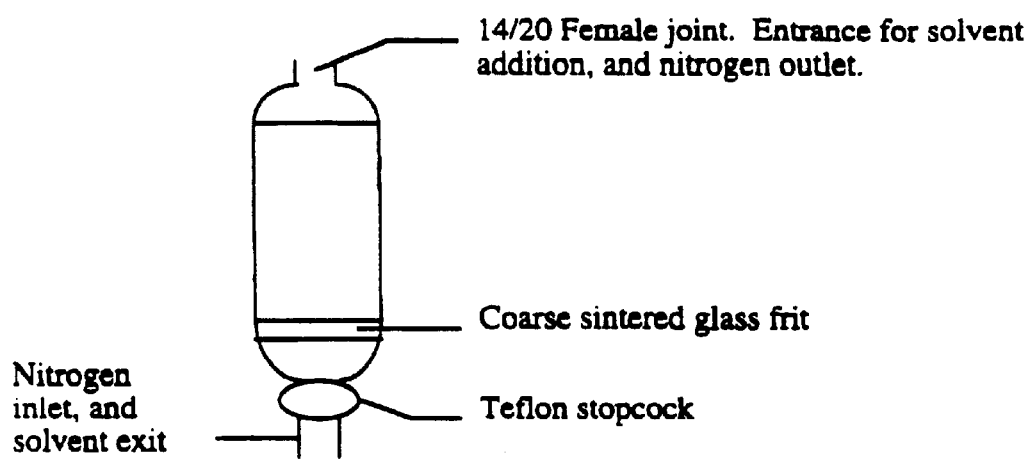
FIG. 13 is a diagram depicting the fritted reaction vessel used to manually synthesize PNA oligomers.

The synthesis of PNA oligomers was performed by means of solid-phase synthesis. The procedure used is as follows:

In general, the Fmoc-PAL-PEG-PS (Fmoc-peptide amine linker-polyethylene glycol-polystyrene) resin was washed and swollen. The resin and all PNA monomers had an Fmoc (9-fluorenylmethoxycarbonyl; see FIG. 12) group attached to the amino ends. This Fmoc protecting group was removed immediately prior to the addition of a monomer and at the end of the synthesis. The first PNA monomer formed an amide bond with the resin and the subsequent PNA monomers formed the amide bond with the growing chain's terminal amino group. Any free amino ends, that fail to react with a monomer, were capped with an acetyl group to prevent undesired PNA sequences from forming, or other reactions from occurring. The Kaiser Test detected if any amino groups were still present. If the Kaiser Test was negative, then the next Fmoc group was removed. The adenine, cytosine, and guanine monomers had Bhoc (Benzhydryloxycarbonyl; FIG. 12) groups protecting the primary amines on the bases. After the desired PNA sequence was synthesized, the PNA was cleaved from the resin during which the remaining Bhoc protecting groups were also removed. The PNA was then precipitated, and soon afterwards purified. The synthesis took place in the fritted reaction vessel, depicted in FIG. 13, so that the reaction mixture was stirred by nitrogen bubbling as well as shaking of the vessel on a mechanical shaker. The explicit procedure for the Fmoc PNA synthesis cycle was as follows.

To prepare the resin, 300 mg (50 μmol of the available amino groups) of the Fmoc-PAL-PEG-PS resin was placed in the reaction vessel and washed four times with 8 mL dichloromethane (DCM). The vessel and resin were then dried over phosphorous pentoxide ($p_2O_5$) under high vacuum for one hour or overnight. The resin was swelled in 7 mL

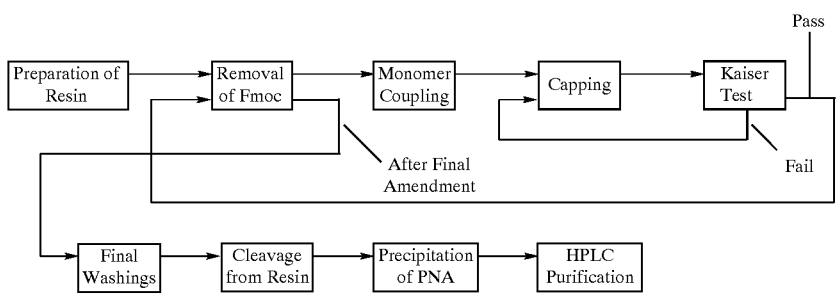

1-Methyl-2-pyrrolidinone (NMP) and bubbled/shaken for ten minutes. The solvent was then drained by vacuum.

The Fmoc group was removed from the Fmoc-PAL-PEG-PS resin by adding 4 mL 20% piperidine/NMP (Pip/NMP), bubbling/shaking for ten minutes, and then draining the solvent by vacuum. The resin was washed twice with N,N-dimethylformamide (DMF), with one minute elapsing per washing. Another 4 mL 20% Pip/NMP was added, bubbled/shaken for 10 minute, and drained. The resin was washed five times with 4 mL of a 1:1 mixture of DCM and DMF. The resin was now ready for the addition of the first PNA monomer.

Before a monomer was added to the resin, the carboxyl group of the monomer was "activated" using O-(7-azabenzotriazol-1-yl)-1,1,3,3-tetramethyluronium hexafluorophosphate (HATU), Diisopropylethylamine (DIPEA), and 2,6-Lutidine. The optimized amounts of each were found to be 200 µmol (four equivalents) to the 300 mg of resin as indicated in Table IV. The structures of the PNA monomers are depicted in FIG. 12.

TABLE IV

Materials used to make the activated monomer complexes.

| Activated Monomer Ingredients | Amount |
| --- | --- |
| Fmoc-A(Bhoc)-OH (mg) | 157 |
| Fmoc-B(Bhoc)-OH (mg) | 152 |
| Fmoc-G(Bhoc)-OH (mg) | 160 |
| Fmoc-T-OH (mg) | 109 |
| HATU (mg) | 82 |
| DIPEA (µL) | 38 |
| 2,6-Lutidine (µL) | 25 |

The PNA monomer and HATU were placed into an Eppendorf vial and 1.4 mL NMP was added. The resulting mixture was vortexed until both dissolved. Then, DIPEA and 2,6-Lutidine were added and the vial shaken again. The solution was transferred to the reaction vessel and bubbled/shaken for twenty-five minutes. The resin was then washed five time with 4 mL 1:1 DCM/DMF each time.

A capping solution was prepared by mixing 45 mL DMF, 3 mL 2,6-Lutidine, and 2.5 mL Acetic anhydride. Six mL of the capping solution was added to the resin and bubbled/shaken for ten minutes. This solution acetylates and blocks any amino ends that may not have reacted with the monomer, thereby forbidding later additions to the amino ends. This capping reduces the chances of producing PNA oligomers of varying lengths, and also increases the purity and quantity of the final product. After the capping step, the resin was washed five times with 4 mL DMF aliquots.

After each capping, the Kaiser Test may be performed to check for free amino ends. A few beads were removed from the reaction vessel and placed in a small borosilicate glass tube. Two drops of 76% w/w Phenol/Ethanol was added to the tube. After adding the Phenol/Ethanol, four drops of 0.0002 M Potassium cyanide/Pyridine and two drops of 0.28 M Ninhydrin/Ethanol were added. The tube was rotated to mix the solution and then heated in a heating block set to 100° C. for five minutes. The tube was removed and the color of the beads observed. A yellow color indicates the absence of free amino ends. If a purple/blue color is observed, fresh capping solution was made up and the capping step repeated. Experience has shown that with fresh capping solution, the Kaiser Test need not be performed after every step, but is done after every third monomer addition.

At this point there was a PNA monomer attached to the resin. In order to add another monomer, the Fmoc group must be removed from the monomer. Thus, the PNA synthesis cycle was repeated with the removal of Fmoc, followed by coupling, capping, and again removal of the Fmoc.

After the final monomer was added, the Fmoc was removed and the resin washed with a 1:1 mixture of DCM/DMF as above. The resin was then washed sequentially five times with 4 mL DCM and five times with 4 mL Methanol. The resin and the reaction vessel were dried overnight in a lyophilizer.

A cleaving solution was prepared with 1.2 mL of freshly distilled m-cresol and 4.8 mL trifluoroacetic acid (TFA). Six mL of the cleaving solution was added to the dried reaction vessel and bubbled/shaken for two hours. The rate of nitrogen flow for bubbling must be slow such that the TFA does not evaporate too quickly (i.e., before the two hours bubbling/shaking step). Occasionally, additional TFA was added to maintain the volume of the cleaving solution. After two hours, the cleaving solution was drained into a 125 mL side-arm filtering flask. The resin was washed two times with 5 mL TFA with the washes being drained into the flask. Nitrogen was blown into the flask at a quick rate to evaporate all of the TFA. A small Dewar flask filled with water slightly above room temperature was placed around the filtering flask to provide a heat sink for the evaporation of the TFA.

Freshly distilled ether (45 mL), chilled to −20° C., was added to the filtering flask to precipitate the PNA while swirling. If the precipitate did not appear very granular, the flask was placed in a −20° C. freezer for thirty minutes. The precipitate was then centrifuged at 3000 rpm for three minutes. After decanting, this step was repeated two more times. The precipitate was dried under high vacuum for fifteen minutes.

The PNA oligomer was then purified by reverse phase HPLC, on a Vydac (2.2 cm×25 cm) $C_8$ column with a gradient elution of 5% B to 100% B in 100 minutes (solvent A=0.1% TFA; solvent B=80% acetonitrile in 0.1% aq. TFA; flow rate=8 mL/min; $\alpha_{max}$=260 nm).

Fractions containing PNA oligomers were collected by lyophilization and stored in dry form at −20° C.

Example 6

Determining PNA Tissue Distribution

To determine the tissue distribution of PNA oligomers after administration, the following experiments are performed. PNA oligomers are administered to rats, recovered from selected tissue after administration, and quantified. Concentrated samples of PNA oligomers, as achieved during syntheses, are readily quantified by UV spectrometry. This method may not be sufficiently sensitive, however, to detect femtomolar concentrations of PNA oligomers that might be found in the plasma of animals after oral administration or in brain after intravenous administration. Thus, analytical equipment such as HPLC coupled with a laser-activated fluorescence detector that can potentially detect sub-attomol ($10^{-18}$ mol) concentrations is used to measure, with high sensitivity, non-radioactive forms of PNA oligomers. This is the simplest, most direct approach for measuring unmodified PNA oligomers directly. Alternative methods of detecting PNA oligomers include the use of radioactive or fluorescent forms of PNA oligomers. Modifying a PNA oligomer, however, to improve detectability may alter plasma membrane or BBB permeability as well as the ability of a PNA oligomer to bind to complementary nucleic acids. Thus, each modified PNA oligomer is tested for functionality before performing tissue distribution experiments. Briefly, modified PNA oligomers are administered to a rat and tested for their ability to engender a biological response as described herein.

Unmodified PNA oligomers are synthesized by automated or manual procedures. Manual synthesis generally provides around 5 to 10 fold greater quantities of PNA oligomers than automated synthesis. The unmodified PNA oligomers are modified to produce radioactive or fluorescent PNA oligomers, if necessary.

1. Automated Synthesis of PNA Oligomers

PNA oligomers are synthesized with Fmoc-N-(2-aminoethyl) glycyl PNA monomers on an Expidite 8909 Nucleic Acid Synthesizer according to the chemistry and protocols developed by the manufacturer (PerSeptive Biosystems, Inc., Framingham, Mass.). The exocyclic amines of the bases adenine, guanine, and cytosine of each Fmoc-PNA monomer are protected with the blocking group benzhydryloxycarbonyl (Bhoc). Synthesis of the PNA oligomers (2×2 $\mu$mol) is on polyamide linker (PAL)-Polyethylene Glycol-olystyrene resin (PerSeptive Biosystems, Inc.) which produces a carboxamide group ($CONH_2$) at the COOH terminus (3') end. After synthesis, the PNA is de-protected and removed from the resin by treatment with a mixture of 80% trifluoroacetic acid (TFA) containing 20% m-Cresol for 90 minutes at 22° C. The PNA oligomer is then precipitated in diethyl ether and purified by reverse phase high performance liquid chromatography on a Vydac $C_{18}$ column at 60° C. with a buffer of 0.1% aqueous TFA and a linear gradient of 0.1% TFA containing 80% acetonitrile/20% water. A major peak (@$A_{300}$ nm) is collected, lyophilized, and verified for its correct mass weight by electro-spray ionazation mass spectrometry on a Sciex API 165B mass spectrometer (Perkin-Elmer, Foster City, Calif.).

2. Manual Synthesis of PNA Oligomers

PNA oligomers are synthesized on a 50 $\mu$mol scale on PS-PEG-PAL resin (PerSeptive Biosystems) using 4 equivalents each of HATU (O-(7-azabenzotriazol-1-yl)-1,1,3,3-tetramethyluronium hexafluorophosphate), diisopropylethylamine, and 2,6-lutidine as carboxyl-activating agents, and 4 equivalents of the protected PNA monomers (PerSeptive Biosystems). The monomers used in the synthesis are Fmoc-2-aminoethylglycine derivatives of 9N-carboxymethyl-N6-benzhydryloxyadenine, 9N-carboxymethyl-N2-benzhydryloxyguanine, 1N-carboxymethylthymine, and 1N-carboxymethyl-4N-benzhydryloxycytosine. The Fmoc group is removed with 20% piperidine in N-methylpyrrolidinone and the deblocking of the Bhoc groups and the removal of the PNA oligomer is carried out in one pot by treatment of the resin-bound PNA with trifluoroacetic acid/m-cresol (4:1 v/v). The crude PNA oligomers are purified by HPLC (Vydac preparative column, C-8, 10 $\mu$m particle size, 22×250 mm) with a gradient elution of 5% B to 100% B in 100 minutes (solvent A=0.1% TFA; solvent B=80% acetonitrile in 0.1% TFA; flow rate=8 ml/minute; UV detection at 260 nm). Correct mass weight is verified as for the automated synthesis described above.

3. Detecting Unmodified PNA Oligomers after Administration

To detect intravenously administered PNA oligomers in blood, Sprague-Dawley rats (200 g male) are prepared by cannulating the jugular vein with silicon tubing under light anesthesia with ether according to well-established procedures. Unmodified PNA oligomers such as NTR1-PNA, MU1R-PNA, or SERT-PNA oligomers are dissolved in isotonic sodium chloride solution and the appropriate dose (e.g., 0.2 to mg/kg) is administered into the jugular vein as a bolus dose. Blood samples (about 0.3 ml) are withdrawn through the cannula at 10, 20, 30, 40, 60, 90, 120, 150, 180, and 240 minutes after the administration into heparinized tubes and centrifuged at 3,000 RPM for 10 minutes. The plasma is then harvested and prepared for HPLC analysis. A total of four rats are used at each dose level. The concentration verses time data generated is subjected to a non-linear pharmacokinetic analysis according to an appropriate model (e.g., one- or two-compartment model) using WinNonlin™ or the MPK pharmacokinetic package, and the various pharmacokinetic parameters (e.g. $\alpha$, $\beta$, $k_{12}$, $k_{21}$, $k_{10}$, $V_C$, $V_\beta$, $V_{ss}$, total clearance, area-under-the-curve (AUC), mean residence time, etc.) are computed.

Similar experiments are performed to detect orally administered PNA oligomers in blood. In this case, unmodified PNA oligomers are administered by gastric intubation (oral administration) and samples collected and analyzed as described above. In addition, the rate and extent of absorption of PNA oligomers in the gastrointestinal tract are determined for PNA oligomers administered orally. Absolute bioavailability of PNA oligomers is calculated from the ratio of log $AUC_{(0-\infty)}$ of the oral administration to log $AUC_{(0-\infty)}$ of the intravenous infusion. The anti-logs of this ratio represents the absolute bioavailability.

In addition to blood, other tissues such as brain and liver are analyzed for the presence of unmodified PNA oligomers. The most appropriate sampling time to examine selected tissues is from when $C_{max}$ (maximum concentration of PNA oligomers) is achieved in the blood to about 5 times the $t_{1/2}$ (half-life). Other sampling times are those times when the maximum behavioral and biochemical effects of the PNA oligomer are observed. Briefly, gross regions (e.g., frontal cortex, cerebellum) are rapidly dissect out, placed on ice, and ground up. The ground up tissue is then is prepared for HPLC analysis to detect the presence of PNA oligomers. The HPLC elution system is the same as described herein for the synthesis of PNA oligomers.

Further, PNA oligomer entry into brain, as well as the accumulation of serotonin as a biochemical marker for the reduction of plasma membrane serotonin transporter expression (See Example 7), is analyzed using in vivo microdialysis online measurements (Kalivas et al., J. Neurochem. 56:961–967 (1991)). Although the implanted microprobe could potentially compromise the BBB, healing around the microprobe should prevent extracranially administered PNA oligomers from leaking into brain. These microdialysis techniques are also useful for detecting modified PNA oligomers such as the radioactive or fluorescent forms of PNA oligomers described below.

4. Synthesis and Detection of Tritiated PNA Oligomers

Experiments using radiolabeled forms of PNA oligomers are performed to determine tissue distribution by measuring radioactivity in a liquid scintillation spectrometer. Tritiated PNA oligomers are made to have increased delectability from unmodified PNA oligomers by tritium exchange. This method provides a compound with a specific activity of at least 10 Ci/mmol. Alternatively, an amino group is added to the 5'-end of an unmodified PNA oligomer. This amino group then is methylated to varying degrees with $CT_3I$ (available from Amersham at 60–85 Ci/mmol) as follows to furnish tritiated mono-, di-, and tri-methylated PNA oligomer derivatives having a minimum specific activity of about 60 Ci/mmol:

Radiolabel 1: $R^1=CT_3$; $R^2=H$; $R^3=H$ (lowest specific activity, N atom basic)

Radiolabel 2: $R^1$ and $R^2=CT_3$; $R^3=H$ (intermediate specific activity, N atom basic)

Radiolabel 3: $R^1$, $R^2$, and $R^3=CT_3$ (highest specific activity, N atom quaternized)

This approach is particularly useful because (a) the positive charge on the nitrogen atom remains intact; (b) the specific activity level of the PNA oligomer is adjustable, depending upon the extent of tritiated methylation; and (c) the resulting structural perturbation of the PNA oligomer after methylation is minimal compared to the native PNA oligomer.

Once synthesized and tested for effectiveness, the tritiated PNA oligomers are administered to animals and their tissue distribution examined. At various sampling times after administration, animals are sacrificed and selected tissues rapidly removed. For example, PNA oligomer entry into brain is measured by sacrificing animals and harvesting brain tissue. Again, gross regions (e.g., frontal cortex, cerebellum) are rapidly dissect out, placed on ice, and ground up. Supernatant fractions are prepared from the ground up tissue and the radioactivity counted. To verify that the recovered radioactive PNA oligomers have the same elution profile as the compound administered to the animal, the recovered radioactive samples are analyzed by HPLC.

Another method for detecting tritiated PNA oligomers involves the use of autoradiographic techniques ex vivo. Briefly, adult male Sprague-Dawley rats are sacrificed by decapitation at various times after injection of [$^3$H]PNA and their brains rapidly frozen on dry ice. Coronal sections (20 microns) are cut on a cryostat at $-16°$ C. and mounted on gelatin coated slides (Fisher Plus Slides). Film radiographs are processed by apposition of radiolabeled section to Biomax MS film with Biomax MS intensifying screens (Kodak). Exposure is for several weeks to months at $-80°$ C. Enhancing equipment, such as the Cyclone™ Storage Phosphor System (Packard Instrument Co.), is also used to increase radioactive signal detection. Quantitative optical density analysis is used to quantify the radioactivity using NIH Image software running on a Macintosh computer. From this analysis, the time course for the entry of radioactive PNA oligomers into brain is determined. In addition, this technique determines any unique regional distribution for individual PNA oligomers.

5. Synthesis and Detection of Iodinated PNA Oligomers

PNA oligomers having a higher specific activity are made from unmodified PNA oligomers by chemically adding a radiolabel by iodination. Briefly, a tyrosine residue is added to the 5'-amino end of an unmodified PNA oligomer and tested to determine if this modification influences the ability of the PNA oligomer to engender a biological response, such as reducing polypeptide expression. If the added tyrosine does not interfere with the function of the PNA oligomer, then the PNA oligomer is modified further by iodinating the tyrosine residue by standard techniques. This radioiodination procedure typically provides a compound having specific activity of about 2,000 Ci/mmol.

Once synthesized and tested for effectiveness, iodinated PNA oligomers are administered to animals and their tissue distribution examined. Experiments similar to the experiments described above are performed, but instead of detecting tritium, the selected tissues are tested for the presence of $^{125}$I.

6. Synthesis and Detection of Fluorescent PNA Oligomers

Modified PNA oligomers having increased delectability are made by adding a fluorescent tag to unmodified PNA oligomers. Briefly, a fluorescein or a dansyl group is conjugated to the 5'-amino end of an unmodified PNA oligomer. This modified PNA oligomer is then tested for functionality and used to measure tissue distribution after administration as described above, understanding that the method of detection involves detecting the presence of a fluorescent tag, not radioactivity.

Example 7

Measuring the Time Course for Onset and Recovery of Biological Responses Engendered by PNA Oligomers To determine the time course for onset and recovery of biological responses engendered by PNA oligomers, the following experiments are performed. These experiments are performed for various routes of administration, such as intravenous, intraperitoneal, and oral. In addition, these types of behavioral, biochemical, and molecular analyses are performed for PNA oligomers targeting different polypeptide as well as for each different PNA oligomer targeting the same polypeptide.

1. Behavioral Responses

For NTR1-PNA oligomers, hypothermia and anti-nociception (hot plate test) after intracranial challenge with NT (18 nmol) are measured as described in Example 1. Briefly, rats surgically implanted with indwelling cannulas receive an administration of NTR1-PNA oligomers by a particular route. These animals are tested for NT-induced hypothermia and anti-nociception 6, 12, 24, and 48 hours after NTR1-PNA oligomer administration to determine the time course for the onset of the effects. Longer and shorter time periods are also tested depending upon the response.

For MU1R-PNA oligomers, anti-nociception (tail flick test) after intraperitoneal challenge with MOR (5 mg/kg) is measured as described in Example 2. MOR-mediated anti-nociception is also measured using the hot plate test described in Example 1. The rationale for use of the hot plate test in this context is provided in Matthes et al., Nature 383:819–823 (1996). Briefly, rats receiving MU1R-PNA oligomers are tested for responsiveness to MOR challenge at various times after MU1R-PNA oligomer administration to determine both the time course for the onset of loss of MOR responsiveness and the time course for the recovery of MOR responsiveness. Since desensitization or tolerance to drug challenge (NT and MOR) can occur with repeated injections, separate groups of animals, staggered with respect to time of testing, are used so that at least 12 hours elapse before the next drug challenge in a particular animal. After determining the time course for the onset of the effects, a time course for the recovery of the response is determined by testing each animal group for up to several days.

For SERT-PNA oligomers, loss of serotonin transport activity is measured by intraperitoneally administering TCP (15 mg/kg) to SERT-PNA oligomer-treated rats and observing behaviors associated with extraneuronal serotonin as described in Example 3. Briefly, rats pretreated with SERT-PNA oligomers are given an injection of TCP and observed for hyperactivity in Opto-Varimex-Minor activity chamber (Columbus Instruments, Columbus, Ohio). Baseline values are measured first by placing the animal in the chamber for a 60 minute habituation period and then recording activity for 30 minutes prior to intraperitoneal TCP administration. After TCP administration, the animals are observed for activity for up to 3 hours. In addition, animals are scored for the presence or absence of the following signs: hind limb abduction, lateral head weaving, tremors, rigidity, Straub tail, hyperreactivity, piloerection, salivation, chromodacryorrhea, wet dog shakes, compulsive circling and ataxia of hind legs.

In experiments using TCP, separate groups of animals that were never exposed to TCP are used since previous results indicate that repeated treatments with TCP, in animals not treated with PNA oligomers, can result in hyperactivity. This hyperactivity, however, was usually of lower magnitude than that seen in animals treated with SERT-PNA oligomers plus a MAO inhibitor. In addition, repeated TCP treatment usually is not accompanied by other signs of serotonin excess (e.g., chromodacryorrhea or bloody tears, hind limb abduction, and wet dog shakes).

To provide additional evidence that the behavioral responses are attributed to reduced polypeptide or messenger RNA expression, rats are sacrificed after behavioral testing and examined at the biochemical and molecular level.

2. Measuring Polypeptide Expression

Onset and recovery times for polypeptide expression are also determined after treatment with various PNA oligomers. In general, after the time required for a maximum effect of a particular PNA oligomer is determined, the time course for recovery is carefully measured after both acute and chronic treatment. Thus, after determining the time point where maximal inhibition is obtained for a given PNA oligomer treatment, the PNA oligomer is given to a different groups of animals. These animals are sacrificed (n=3 at each time point) and analyzed at various time points after the predetermined time when the level of inhibition is maximal to determine the recovery phase. For example, separate groups of animals are sacrificed at 6 hours, 12 hours, 24 hours, 36 hours, 2 days, 3 days, 4 days, and 5 days after the respective time for maximum effect of each PNA oligomer treatment. Times for measurement of recovery after chronic treatment with PNA oligomers are the same as with acute treatment. Chronic treatments are achieved by using an osmotic minipump (Alzet; 2ML4, 2 ml capacity, 2.5 $\mu$l/hour delivery rate) infusing its contents into a jugular or subcutaneous cannula for about four weeks. Additional measures for the animals chronically treated with PNA oligomers include daily measurement of body weight, gross observation of behavior, and analysis of blood samples at the end of the chronic treatment to determine blood chemistries, including liver function studies.

Radiolabeled ligand binding assays for NTR1, MU1R, and the plasma membrane serotonin transporter are performed to determine both the reduction and recovery of specific polypeptide expression. In general, separate groups of animals (n=3 at each time point) are treated with specific PNA oligomers, at a dosage determined to be effective, and sacrificed at 6, 12, 24, 36, and 48 hours after treatment. Brain tissue is collected for NTR1, MU1R, and serotonin transporter binding, intestinal tissue (ileum and jejunum) is collected for NTR1 and MU1R binding, and blood collected for serotonin transporter binding. The binding and biochemical assays are performed as described in Examples 1–3. These types of measurements reflect both polypeptide turnover as well as rates of polypeptide synthesis.

NTR1 binding sites for animals treated with NTR1-PNA oligomers are tested by measuring the binding of radiolabeled NT in brain and intestinal tissue (ileum and jejunum). Using competition binding assays, the concentration ($B_{max}$) of binding sites for NT in homogenates prepared from freshly obtained PAG, hypothalamus, jejunum and ileum tissue of adult Sprague-Dawley rats is measured. Homogenates of brain and the jejunum and ileum tissue are prepared as described in Example 1. In addition, the jejunum and ileum tissue is prepared from whole intestinal tissue homogenates with the rough nuclear membrane being used for binding assays. Competition binding assays are performed as described elsewhere (Gaudriault et al., *J. Neurochem.* 62:361–368 (1994)) with the following modifications: binding buffer also contains 0.5% glycerol, 0.01 mM phenylmethylsulfonylfluoride, 7 $\mu$l pepstatin, 0.8 $\mu$M aprotonin, 12 $\mu$M leupeptin, 0.1 mM iodoacetamide, and 0.25 mM EDTA (all from Fisher Scientific, Pittsburgh, Pa.), but does not contain N-benzyloxycarbonyl prolyl prolinal. Brain homogenates (about 1 mg wet/wt of polypeptide) are incubated with [$^{125}$I]NT (0.2nM; NEN, Boston, Mass.) and increasing concentrations of non-radioactive [$^{126}$I]NT in a total volume of 100 $\mu$L. Assays are performed in 96 well plates with about 2.5 mg wet wt per well for PAG and hypothalamus samples and about 125 $\mu$g polypeptide per well for intestine samples. The radioligand binding data are analyzed with the software program LIGAND running on a PC.

MU1R binding sites for animals treated with MU1R-PNA oligomers are tested by measuring the binding of radiolabeled morphine in brain. As with NTR1, the $B_{max}$ for MOR binding sites is determined. Again, homogenates from freshly obtained PAG and jejunum and ileum tissue of adult rats are prepared and competition binding assays are performed as described herein. Briefly, assays are performed in 96 well plates with about 2.5 mg wet wt per well for PAG samples and about 125 $\mu$g protein per well for intestine samples. Typically, 2 nM [$^3$H]morphine (NEN, Boston, Mass.) is used for each binding assay.

The expression of the plasma membrane serotonin transporter is determined by measuring the binding of radiolabeled imipramine in brain. Imipramine is an antidepressant that binds plasma membrane serotonin transporters reversibly. Briefly, about 300 mg of cerebral cortex are homogenized in 10 volumes of 50 mM Tris-HCl buffer (pH 7.7) with a Brinkmann Polytron (setting 7 for 10 seconds). The homogenate is centrifuged at 20,000×g for 15 minutes (4° C.). The pellets are resuspended in 50 mM Tris-HCl (pH 7.4) containing 4 mM $CaCl_2$ and incubated for 15 minutes at 37° C. Samples then are spun down and the washing procedure repeated. After final centrifugation, the pellets are resuspended in 50 volumes of 50 mM Tris-HCl containing 4 mM $CaCl_2$, 10 $\mu$M pargyline, and 0.1% ascorbic acid. The binding assay is performed by incubating 100 $\mu$l of different concentrations of imipramine (0.01 nM–0.1 $\mu$M), 100 $\mu$l [$^3$H]imipramine (10 $\mu$M), and 800 $\mu$l of tissue preparation at 37° C. for 30 minutes. For non-specific binding, 100 $\mu$l of imipramine is added to a set of tubes. The binding is terminated by rapid filtration over a glass filter coated with 0.5% polyethylenimine using a Brandell cell harvester. The filters are then washed 3 times with 2 ml 0.9% NaCl. The radioactivity is counted and the data analyzed.

In addition, the expression of the plasma membrane serotonin transporter is determined by measuring the binding of radiolabeled paroxetine in brain. Briefly, about 300 mg of cerebral cortex are homogenized in 15 ml ice cold 50 mM Tris buffer containing 120 mM NaCl and 5 mM KCl at pH 7.4 using a Brinkmann Polytron (setting 4 for 5 seconds). The homogenate is centrifuged at 18,000×g and 4° C. for 10 minutes. The pellets are resuspended in buffer, homogenized, centrifuged again, and resuspended to a final concentration of 60 $\mu$g polypeptide/ml in the binding assay buffer. The homogenates are incubated for 60 minutes at 22° C. with 0.1 nM [$^3$H]paroxetine and varying concentrations (1 pM–10 nM) of paroxetine in a final volume of 1 ml. Non-specific binding is determined in the presence of 100 $\mu$M serotonin. The reaction is stopped by the addition of 6 ml ice-cold buffer and filtration through Whatman filters pre-coated with 2% polyethyleneimine using a Brandel Harvester. The filters are then washed 3 times with 2 ml 0.9% NaCl. The radioactivity is measured and the data analyzed as described above.

Platelets also express serotonin transporters. To analyze [$^3$H]imipramine binding to platelets, the following procedure is performed. Whole blood is collected from an animal by cardiac puncture, after the sternum is split. The blood is aspirated during systole and transferred to plastic tubes containing 10 U porcine sodium heparin/ml blood. The tube is then capped and inverted several times. The blood is carefully centrifuged at 177×g at 20° C. for 12 minutes, accelerating to the set g force over an eight minute span. The resulting platelet-rich plasma (PRP) is removed and stored in a cryovial −80° C. until use. The binding assay is performed by a modification of previously described methods (O'Shaugnessey et al., *Microsurgery* 17:238–242 (1996) and Paul et al., *Life Sci.* 26:953–959 (1980)). Briefly, PRP is centrifuged at 18,000×g for 10 minutes at 4° C. Platelet membranes are washed and centrifuged twice with 50 volumes of buffer (Tris-HCl 0.5 M; NaCl 0.2 M; KCl 0.005 M; 0.01 M lithium-HEPES). Membranes are disrupted with a Brinkmann Polytron at setting 6 for 10 seconds. Membranes are washed again, centrifuged, and resuspended in buffer to a final polypeptide concentration of 3.5 mg/ml. Incubation reactions for each assay contain 25 μl [$^3$H]imipramine (1 nM), 25 μl cold competitor, and 200 μl of membranal preparation. Incubation are for 1 hour at 4° C. After incubation, the reaction mixture is diluted with 5 ml cold buffer and filtered through Brinkmann GF/F glass fibre filters that are then washed three times and counted on Wallac Betaplate™ counter. Data analyses is the same as described above for the other binding assays.

In addition, [$^3$H]paroxetine binding to platelets is measured as follows. After collecting the blood as described above, the blood is carefully centrifuged at about 180×g at 20° C. for 12 minutes, accelerating to the set g force over an eight minute span. The PRP is removed and stored in a cryovial at −80° C. until use. The binding assay is performed using methods described elsewhere with slight modification (Marcusson et al., *J. Neurochem.* 50:1783–1790 (1988) and Wall et al., *Mol. Pharmacol.* 43:264–270 (1993)). Briefly, the PRP is centrifuged at 18,000×g for 10 minutes at 4° C. Platelet membranes are washed and centrifuged twice with 50 volumes of buffer (Tris-HCl 0.5 M; NaCl 0.2 M; KCl 0.005 M; 0.01 M lithium-HEPES). Membranes are disrupted with a Brinkmann Polytron at setting 6 for 10 seconds. Membranes are again washed, centrifuged, and resuspended in buffer to a final polypeptide concentration of 3.5 mg/ml. Incubation reactions contain 25 μl [$^3$H]paroxetine (0.5 nM), 25 μl cold competitor, and 200 μl of membranal preparation. Incubations are for 1 hour at 4° C. After incubation, the reaction mixture is diluted with 5 ml cold buffer and filtered through Whatman GF/F glass fibre filters that are then washed three times and counted on a Wallac Betaplate™ counter. Data analyses is the same as described above for the other binding assays.

For rats treated with SERT-PNA oligomers, increases in extracellular levels of serotonin also are measured by means of intracerebral microdialysis. Any increases in serotonin levels is attributed to a decrease in plasma membrane serotonin transport activity. Briefly, rats are stereotaxically (spatial coordinates: 2 mm anterior to the bregma, 3 mm from the mid-sagittal suture, and 6 mm ventral from the dura) implanted into the anterior lateral striatum with a microdialysis probe (CMA/12, 3 mm length, BAS, W. Lafayette, Ind.) connected online to an HPLC apparatus for analysis of serotonin levels. These animals are allowed to move about freely after the probe has been inserted. The probe is inserted into the lateral striatum by a guide cannula. A polycarbonate/polyether copolymer dialysis membrane is used, with an inner diameter of 400 μm and a molecular weight cutoff of 20,000. The perfusion fluid consists of 4.0 mM KCl, 130 mM NaCl, 2.0 mM CaCl$_2$, 1.2 mM MgCl$_2$, and 0.2 mM phosphate buffered saline to give a pH of 7.4 and a final sodium concentration of 137 mM. The flow rate is about 2.0 μl/min. Serotonin and 5-HIAA (5-hydroxy indole acetic acid) are determined using HPLC with electrochemical detection. The mobile phase (20 mM sodium acetate, 10 mM citric acid, 3.0 mM EDTA, 800 μM octane sulphonic acid sodium salt monohydrate, 1.0 mM diethylamine, and 10% (vol/vol) methanol, pH 5.0, with 2.0 pmol N-methyl-5HT as an internal standard) is filtered through 0.2 μm nylon membrane filters and degassed under vacuum before pumping at a rate of 1.5 ml/minute through a 3.0 μm C$_{18}$ HR-80 reversed phase analytical column (8.0 cm×4.6 mm i.d.; ESA, Inc., Chelmsford, Mass.) that is connected to a model 5011 high sensitivity analytical cell (ESA, Inc.). Electrochemical detection is performed using a model 5200A Coulochem II EC Detector (ESA, Inc.).

Attempts are made, as described above, to use this method to measure PNA oligomers as well. In any case, the placement of the probe is verified by histological techniques similar to the techniques used to determine the cannula placement as described in Example 1.

In a more direct assessment of polypeptide expression, monoclonal or polyclonal antibodies to the various polypeptides are used to immunoprecipitate polypeptides radiolabeled ex vivo in cellular homogenates. These cellular homogenates are obtained from animals treated with PNA oligomers.

Ribosomal preparations are prepared from the brain of control and PNA oligomer-treated animals as described elsewhere (Hendrich and Porterfield, *Proc. Soc. Exp. Biol. Med.* 213: 273–280 (1996)). Briefly, tissue homogenization is done in medium (E) composed of 50 mM Tris, 250 mM KCl, and 10 mM MgCl$_2$ at a pH of 7.6. The mixture is centrifuged at 13,000 g for 15 minutes. The supernatant is filtered through glass wool, and Lubrol-WX (10% in 10 mM MgCl$_2$) and deoxycholic acid (10% in distilled H$_2$O) is added to give a 0.5% Lubrol and a 1.0% deoxycholic acid mixture. This mixture is placed in a teflon-glass homogenizer and gently mixed with three strokes of the pestle, while standing for 30 minutes. Each sample is then diluted with three volumes of Medium E and centrifuged for 2 hours at 78,000 g. The supernatant is discarded, the pellet is rinsed with Medium E and transferred to the homogenizing tube in a total volume of 2 ml of Medium E. The pellet is then resuspended by a few gentle strokes of the pestle. The resuspended pellets are then layered on 5 ml of 1 M sucrose in Medium E and centrifuged through this medium for 2.5 hours at 105,000 g. The supernatant is discarded and the pellet is washed with Medium G (50 mM Tris, 150 mM KCl, and 10 mM MgCl$_2$ at a pH of 7.6). The pellet is suspended in Medium G, frozen with liquid nitrogen, and stored at −80° C. Ribonuclease inhibitor (5 units) from placenta is utilized and all procedures are carried out in an ice bath.

PNA oligomer-treated animals are sacrificed when the PNA oligomers are known to engender a maximum reduction in polypeptide expression as determined from the experiments described above. Endogenous polypeptides being synthesized are then radiolabeled with [$^{35}$S] methionine. A time course for the production of 10% (w/v) TCA-precipitable radioactivity is determined with an aliquot from each ribosomal preparation to establish the viability of the preparation and the maximum time of incorporation of the radiolabeled methionine. Antibodies to the polypeptide targeted by the PNA oligomer administered to the animal is used to immunoprecipitate the products by standard techniques (Jagus R., In Methods in Enzymology. Edited by: S L Berger and A R Kimmel. Vol. 152. Orlando, Academic Press, Inc., 1987, pp. 296–304). The immunoprecipitated material is then analyzed by polyacrylamide gel electrophoresis to determine the presence or absence of the specifically targeted polypeptide. Antibodies against MU1R and the plasma membrane serotonin transporter are commercially available (Chemicon International, Inc.).

3. Measuring Messenger RNA Expression

Quantitative reverse transcriptase-PCR (RT-PCR) is performed on PNA oligomer-treated and control animals using GAPDH (glyceraldehyde 3-phosphate dehydrogenase) as an internal standard. Total RNA is isolated from approximately 20 mg of tissue using the S.N.A.P.™ Total RNA Isolation Kit (Invitrogen, Carlsbad, Calif.) according to the manufacturer's instructions. The first strand cDNA is synthesized from 500 ng of total RNA using the cDNA CycleKit (Invitrogen, Carlsbad, Calif.) also according to the manufacturer's instructions. Polynucleotide kinase, Taq DNA polymerase, primers, and dNTPs are obtained from Gibco BRL. [$\gamma$-$^{32}$P]ATP is obtained from New England Nuclear (Boston, Mass.). Sense primers are end-labeled and purified from free nucleotides using Chroma Spin 10 columns (Clontech, Palo Alto, Calif.). The PCR cycles are performed on a GeneAmp PCR System 9600 (Perkin Elmer, Norwalk, Conn.).

The following primers are used:

NTR1, +694S: 5' GCC ACT GTC AAG GTC GTC 3' (SEQ ID NO: 4)

NTR1, +965AS: 5' AGC CAG CAG ACC ACA AAG 3' (SEQ ID NO: 5)

(This amplifies products of 271 bp for rat and 259 bp for human in the coding region)

SERT, +1532 5' CCG TGT CTT GGT TCT ATG G 3' (SEQ ID NO: 6)

SERT, +1074AS 5' GGT ATT GGA AAA GCC GTA GC 3' (SEQ ID NO: 7)

(This amplifies a 173 bp product at 3' end of coding region)

MOR1, +859S: 5' CTG TAT TTA TCG TCT GCT GG 3' (SEQ ID NO: 8)

MOR1, +1091AS: 5' AGT GGA GTT TTG CTG TTC G 3' (SEQ ID NO: 9)

(This amplifies a 233 bp product at 3' end of coding region)

GAPDH, +6S: 5' TGA TGA CAT CAA GAA GGT GGT GAA G 3' (SEQ ID NO: 10)

GAPDH, +11AS: 5' TCC TTG GAG GCC ATG TAG GCC AT 3' (SEQ ID NO: 11)

(This amplifies products of 238 bp for wild-type and 175 bp for deletion mutant in the coding region)

PCR fragments of the human NTR and of a GAPDH deletion mutant are used as exogenous standards to control for tube-to-tube variation in the appropriate PCR amplifications. The NTR1 +694S and +965AS primers amplify 271 bp and 259 bp fragments for the rat and human NTR, respectively. The GAPDH +6S and +11AS primers amplify 238 bp and 175 bp fragments for GAPDH and its deletion mutant, respectively. Exogenous standards for the serotonin transporter and the MOR1 are generated using the PCR Mimic™ Construction Kit (Clontech).

PCR reactions contain 20 mM Tris (pH 8.4), 50 mM KCl, 200 $\mu$M dNTPs, 500 $\mu$M of each primer, 1.5 mM MgCl$_2$, 0.5 units Taq DNA polymerase, 10% DMSO, 5×10$^5$ cpm labeled primer, and 0.2 $\mu$l cDNA in a 25 $\mu$l reaction. After an initial denaturation at 94° C. for 1 minute, cycle parameters are 94° C. for 30 seconds, 55° C. for 30 seconds, and 72° C. for 30 seconds for approximately 25 cycles, followed by a 10 minute extension at 72° C. PCR is stopped before the reactions reach the plateau phase that is determined empirically for both the target and the control. Products are separated on a 5% Long Ranger™ sequencing gel containing 7 M urea, and detected using a Storm860™ Phosphoimager (Molecular Dynamics, Sunnyvale, Calif.). Data is analyzed using Image Quant™ Software (Molecular Dynamics, Sunnyvale, Calif.).

In addition, quantitative in situ hybridization histochemistry is also performed to measure specific mRNA levels using procedures known to those skilled in the art.

Example 8

Biological Responses Engendered by Sense Antisense, and Mismatch PNA Oligomers

1. Sense, Antisense, and Mismatch PNA Oligomers

As described in Examples 1 and 4, the antisense PNA oligomer NTR1-PNA reduced NT responsiveness after either an intracranial or extracranial administration as evidenced by the failure of NT to induce anti-nociception and hypothermia. In addition, this reduced NT responsiveness correlated with a reduction in NTR1 polypeptide as evidenced by a reduction in [$^{125}$I]NT binding. It is noted that the antisense PNA oligomer NTR1-PNA may be designated herein as either NTR1-PNA or AS-NTR1-PNA to reflect the antisense nature of its sequence. Table V contains a list of PNA oligomers used to evaluate the ability of PNA oligomers to engender biological responses in a sequence specific manner.

TABLE V

Gene targets, sense, antisense, and mismatch PNA sequences.

| PNA Abbreviation | Rat Gene Product | Gene Product Abbreviation | PNA Sequence | Location of Complementary Sequence |
|---|---|---|---|---|
| NTR1-PNA or AS-NTR1-PNA | Neurotensin Receptor Subtype 1 | NTR1 | 5'-CATTGCTCAAAC-3' (SEQ ID NO: 1) | Coding Region (Anti-sense NTR1) |
| mismatch-AS-NTR1-PNA | Neurotensin Receptor Subtype 1 | NTR1 | 5'-TATGGCACAGAC-3' (SEQ ID NO: 12) | Coding Region (Anti-sense NTR1) |
| Sense-NTR1-PNA | Neurotensin Receptor Subtype 1 | NTR1 | 5'-GTTTGAGCAATG-3' (SEQ ID NO: 13) | Coding Region (Sense NTR1) |
| MU1R-PNA | Morphine Receptor Subtype 1 | MU1R | 5'-CAGCCTCTTCCTCT-3' (SEQ ID NO: 2) | 5' non-coding region |

2. Effects of PNA Oligomer Treatment on Neurotensin Responsiveness

Four different PNA oligomers were used to study NT responsiveness (Table V). The sequence of the sense-NTR1-PNA oligomer (5'-GTTTGAGCAATG-3' (SEQ ID NO:13)) has specificity for NTR1 and is complementary to the AS-NTR1-PNA oligomer. In addition, the sequence of the mismatch-AS-NTR1-PNA oligomer is similar to that of the AS-NTR1-PNA oligomer but contains a mismatch at every third base pair (mismatch indicated in bold; 5'-TATGGCACAGAC-3' (SEQ ID NO:12)).

These PNA oligomers were made on an Expedite 8909 synthesizer or manually synthesized on a 50 µmol scale using PS-PEG-PAL resin (1 equiv) and Fmoc-protected nucleobase monomers (6 equiv; Perseptive Biosystems, Inc., Framingham, Mass.) in the presence of diisopropylethylamine and 2,6-lutidine. PNAs were removed from the resin support and blocking groups were removed by cleavage (2 hours) at RT in 80% TFA containing 20% (v/v) m-cresol. The PNAs were precipitated into cold diethyl ether and were purified by RP-HPLC on a Vydac Q8 column (25 mm×250 mm) at 55° C.

AS-NTR1-PNA, mismatch-AS-NTR1-PNA, and MU1R-PNA were injected intraperitoneally (10 mg/kg) independently, into separate groups of male Sprague-Dawley rats (Harlan, Prattville, Ala.). The sense-NTR1-PNA oligomer, however, was microinjected directly into the periaqueductal gray (PAG; 5 µg), the major area in the brain involved with perception of pain (nociception). Twenty-four hours after injection of a PNA oligomer, rats were tested with NT (18 nmol), which was microinjected into the PAG because NT is rapidly degraded upon systemic administration and does not cross the blood-brain barrier. Thirty minutes after receiving NT, animals were scored for anti-nociception (hot plate at 52° C.) and hypothermia (rectal probe). Again, anti-nociception scores were calculated as percent of maximum possible effect (% MPE) with the following equation: % MPE=[(post-drug latency time minus pre-drug latency time)/(cut-off time minus pre-drug latency time)]×100; where the cut-off time (i.e., the time when the animal was removed from the device) was 30 seconds for a hot plate test and 12 seconds for a tail flick test. Statistical analysis was done using the rank sum test.

Figure 14:
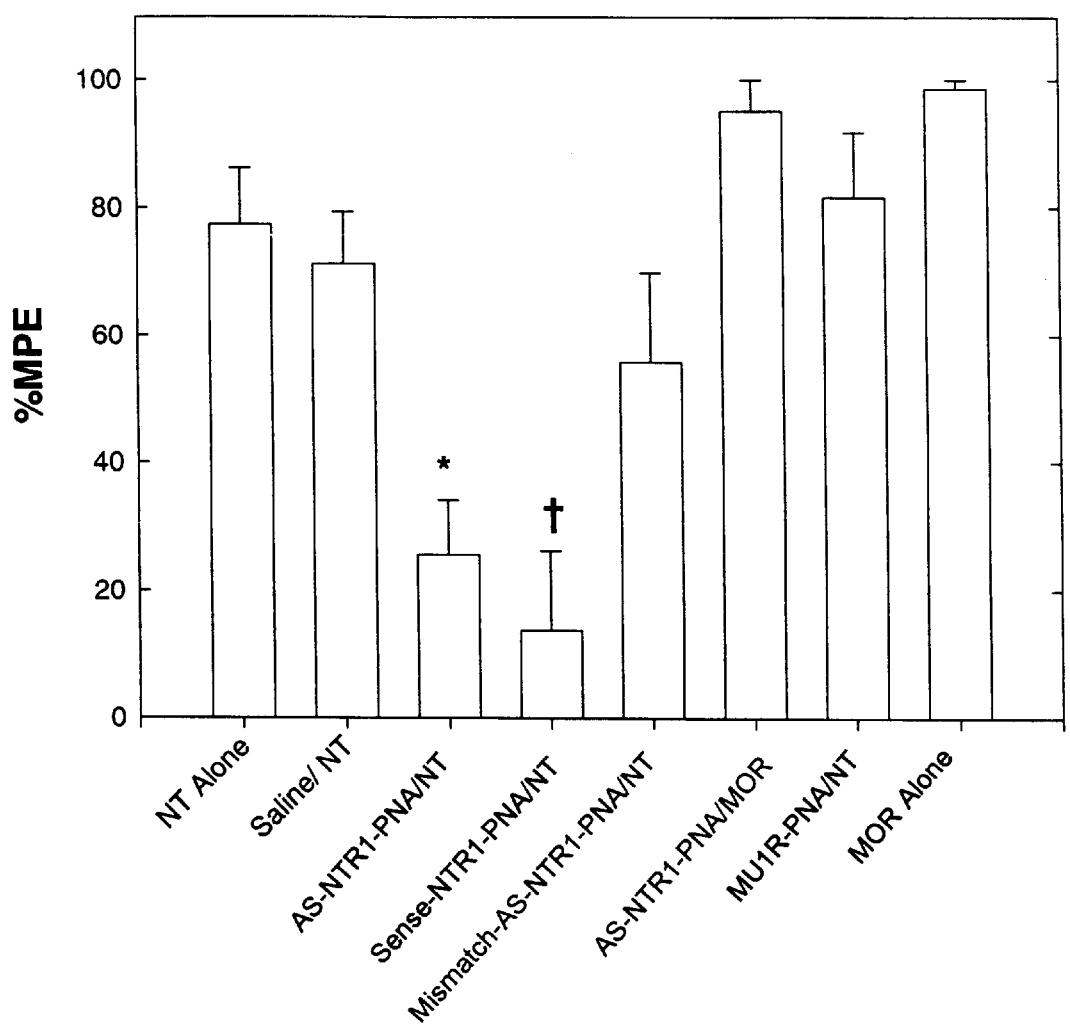
FIG. 14 is a bar graph depicting the maximal possible effect as a percent of baseline response for rats receiving saline, AS-NTR1-PNA, sense-NTR1-PNA, mismatch-AS-NTR1-PNA, or MU1R-PNA oligomer on day 0 and challenged with NT or MOR on day 1. The description before the slash ("/") at the bottom of each bar indicates pretreatment, while the drug listed after the slash indicates the drug used for testing. * represents P<0.001 vs. NT alone, and † represents P=0.002 vs. NT alone.

Animals receiving the AS-NTR1-PNA oligomer (10 mg/kg) intraperitoneally scored an average of 25% MPE (P<0.001 vs. untreated animals) compared to no pretreatment or vehicle-treated (no PNA) animals, which scored 77% and 71% MPE, respectively (FIG. 14). Thus, the animals that received the AS-NTR1-PNA oligomer and then NT, more readily perceived the pain and therefore spent less time on the hot plate because the effects of NT were blocked by this PNA treatment. Animals receiving the mismatch-AS-NTR1-PNA oligomer (10 mg/kg) intraperitoneally scored a mean of 60% MPE, which was not statistically significant compared to untreated animals (P=0.38). It is noted, however, that five of the seven animals receiving the mismatch-AS-NTR1-PNA oligomer exhibited a % MPE value below the mean % MPE obtained from untreated animals. Thus, the overall effect of the mismatch-AS-NTR1-PNA oligomer appears to be a modulation of the response observed in the AS-NTR1-PNA oligomer-treated animals. The animals receiving sense-NTR1-PNA oligomer (PAG; 5 µg) had an anti-nociceptive score of 14% MPE (P=0.002 vs. untreated animals). In addition, two animals receiving sense-NTR1-PNA oligomer (10 mg/kg) intraperitoneally had an anti-anti-nociceptive score of 5.4±5.4% MPE. The animals that received the MU1R-PNA oligomer (10 mg/kg) intraperitoneally (serving as a control for toxic or nonspecific PNA effects) scored 82% MPE in response to NT, a value that was nearly identical to that for animals receiving no pretreatment or vehicle. As an added measure of specificity for the NT system, animals that were treated with the AS-NTR1-PNA oligomer and lacked anti-nociception when tested with NT were tested with MOR (5 mg/kg; intraperitoneal injection) and thirty minutes later scored for anti-nociception using the tail flick assay described herein. These AS-NTR1-PNA oligomer-treated animals scored 95% MPE, which was essentially identical to that found for animals not injected with PNA and tested with morphine (scored 99% MPE).

Figure 15:
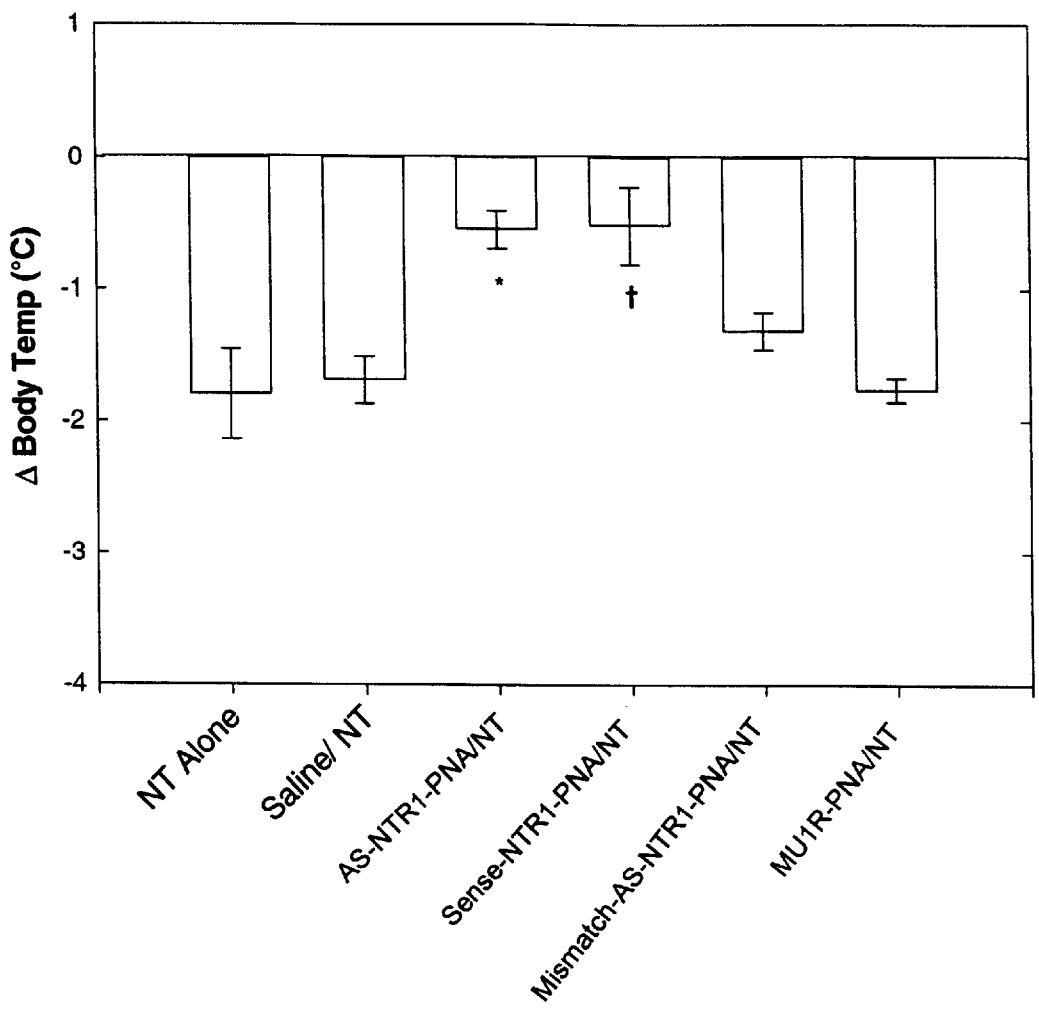
FIG. 15 is a bar graph depicting the body temperature change as a percent of baseline response for rats receiving saline, AS-NTR1-PNA, sense-NTR1-PNA, mismatch-AS-NTR1-PNA, or MU1R-PNA oligomer on day 0 and challenged with NT on day 1. The description before the slash ("/") at the bottom of each bar indicates pretreatment, while the drug listed after the slash indicates the drug used for testing. * represents P<0.001 vs. NT alone, and † represents P=0.008 vs. NT alone.

Immediately after the 30 minutes NT anti-nociception test, animals were examined for body temperature changes in response to NT (FIG. 15). Animals treated with the AS-NTR1-PNA oligomer (10 mg/kg) intraperitoneally or the sense-NTR1-PNA oligomer (PAG; 5 µg) had a body temperature change of –0.5° C., while the no pretreatment or vehicle control animals had a body temperature change of –1.8 and –1.7° C., respectively. These differences were highly significant (P<0.01). In addition, the two animals treated with the sense-NTR1-PNA oligomer (10 mg/kg) intraperitoneally had a body temperature change of –0.45±0.15° C. Animals treated with the mismatch-AS-NTR1-PNA oligomer (10 mg/kg) intraperitoneally had a mean body temperature change of –1.3° C., which was not significantly different when compared to that for untreated animals (P=0.83). It is noted, however, that six of the seven animals receiving the mismatch-AS-NTR1-PNA oligomer exhibited a body temperature change that was less than the mean body temperature change observed in animals not receiving a PNA oligomer. Thus, the overall effect of the mismatch-AS-NTR1-PNA oligomer appears to be a modulation of the response observed in the AS-NTR1-PNA oligomer-treated animals. The animals that received the MU1R-PNA oligomer (10 mg/kg) intraperitoneally had a body temperature change similar to that of the untreated animals. Thus, these behavioral results indicated that PNA oligomers act in a sequence specific manner and that the mere injection of a PNA does not, by itself, alter whole animal responses to a test drug. Moreover, these results indicate that the introduction of base pair mismatches can modulate the observed biological responses.

Figure 16:
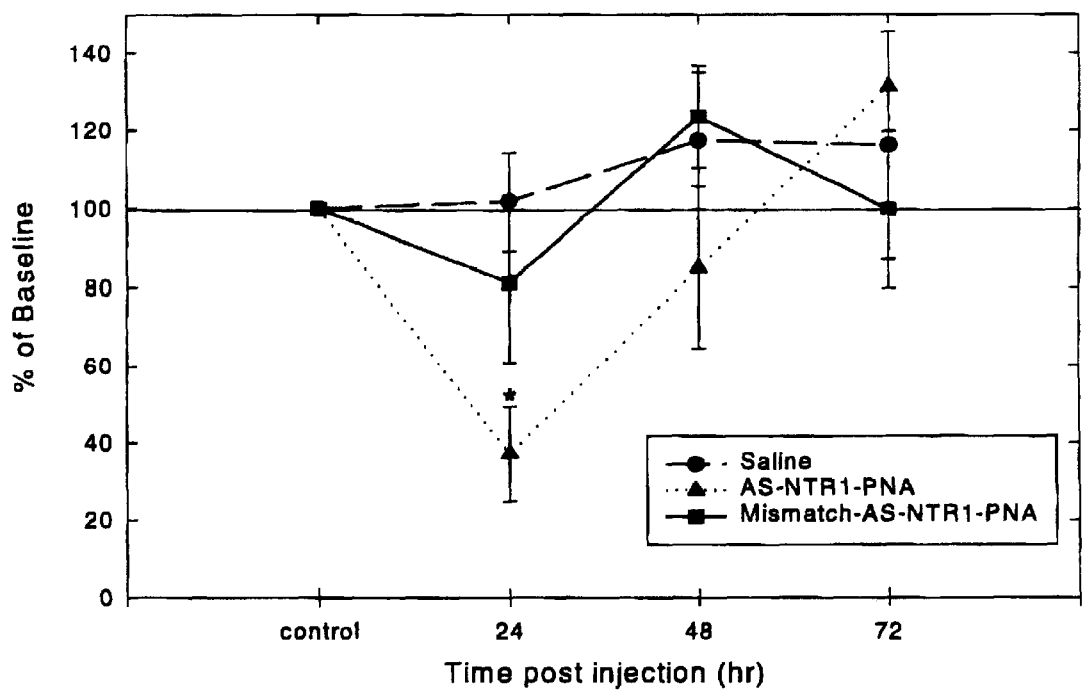
FIG. 16 is a graph plotting maximal possible effect as a percent of baseline response for rats receiving saline (n=4), AS-NTR1-PNA (n=4), or mismatch-AS-NTR1-PNA (n=4) and challenged with NT at the times indicated.
Figure 17:
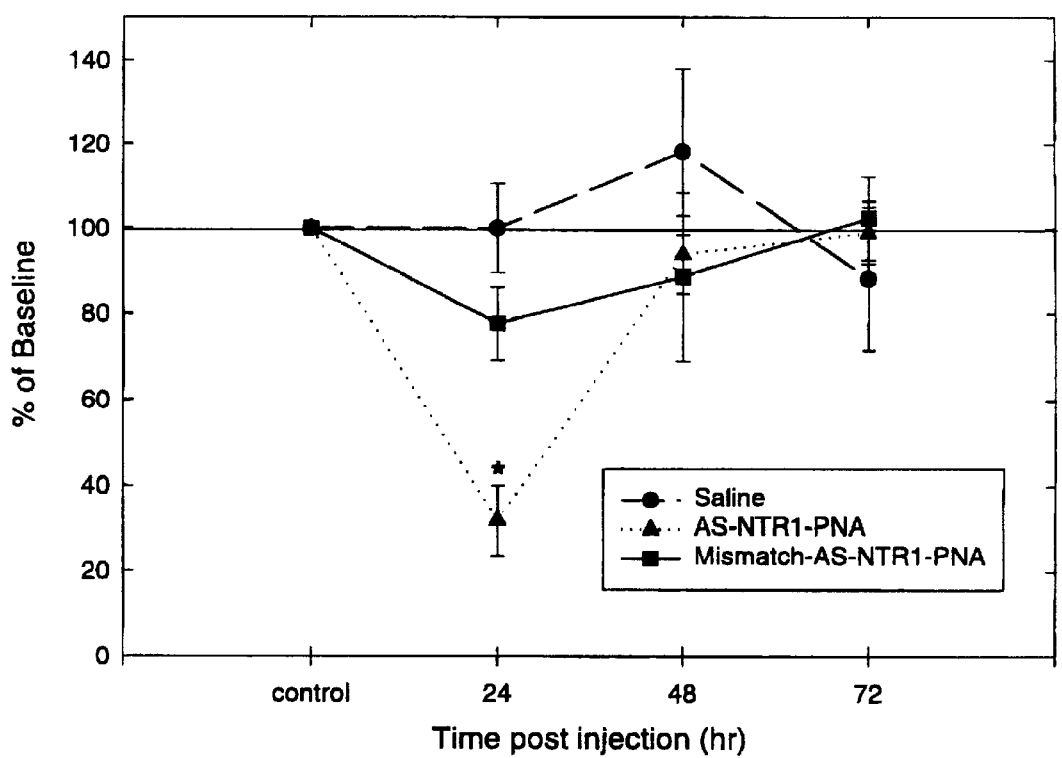
FIG. 17 is a graph plotting body temperature change as a percent of baseline response for rats receiving saline (n=4), AS-NTR1-PNA (n=4), or mismatch-AS-NTR1-PNA (n=4) and challenged with NT at the times indicated.

The time course for recovery of the inhibitory effect of a single PNA injection (10 mg/kg) was determined with another group of animals, which were tested every 24 hours with NT, until the responses to NT returned to the level seen in untreated animals (FIGS. 16 and 17). The responses to NT in animals that had received the AS-NTR1-PNA oligomer returned to baseline levels within 48 hours after PNA injection and remained normal at 72 hours. Later time points were not included in the analysis, as some animals (including controls) started to respond erratically to NT after receiving more than three doses of the peptide which is likely due to receptor desensitization. This reversibility of the inhibitory effects of PNA treatment further indicates the sequence specific manner in which PNA oligomers act. In other words, the responses observed after PNA oligomer treatment do not appear to be the result of non-specific or toxic effects on cells.

3. Dose-response Analysis

Figure 18:
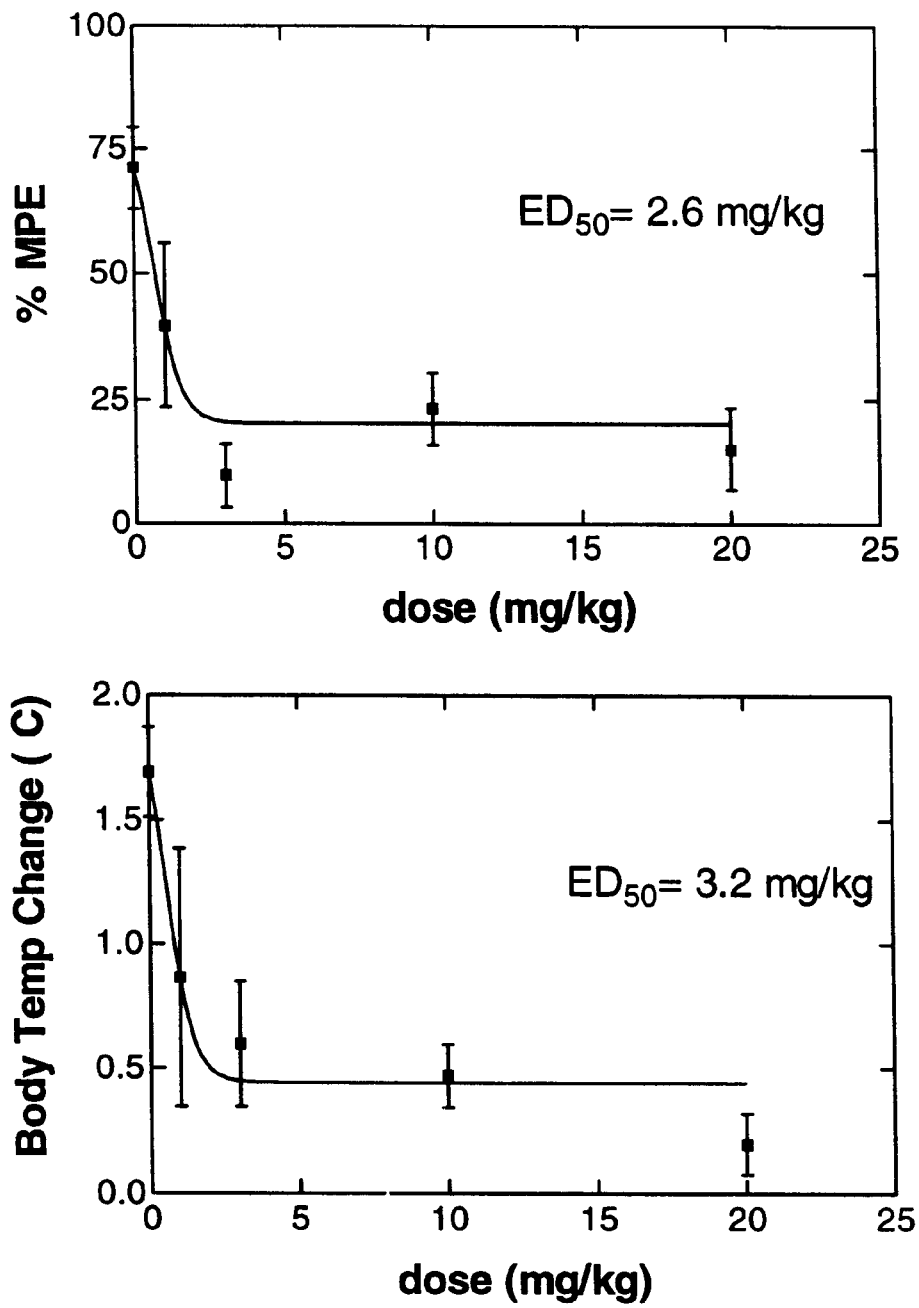
FIG. 18 is a graph plotting maximal possible effect (top panel) and body temperature change (bottom panel) as a percent of baseline response for rats receiving AS-NTR1-PNA (n≧4 at each dose) intraperitoneally. $ED_{50}$'s were calculated by determining the effective dose (mg/kg) that gave 50% of the maximal response.

To determine the potency of PNA treatment in vivo, dose-response curves for the AS-NTR1-PNA oligomer were obtained (FIG. 18). The AS-NTR1-PNA oligomer produced steep dose-response curves, which are characteristic of antisense effects, and appeared to have identical potency at reducing both responses to NT with $ED_{50}$'s of 2.6 and 3.2 mg/kg for anti-nociception and hypothermia, respectively. The dose response data are representative results utilizing one batch of PNA. Some variation in potency from different PNA preparations was observed. For this reason, all other experiments were performed at 10 mg/kg, a dose which provided consistent results regardless of PNA batch.

4. Effects of PNA Oligomer Treatment on Neurotensin Binding Sites

AS-NTR1-PNA oligomer treatment blocked the pharmacological effects of NT by reducing the expression of NTR1 polypeptide. Animals that received the AS-NTR1-PNA oligomer intraperitoneally were sacrificed 24 hours after injection for use in binding assays to measure levels of [$^{125}$I]NT and [$^3$H]morphine binding sites. From these animals the PAG, the rest of brain, and portions of the small intestine (jejunum and ileum) were harvested. The small intestine was selected because it is a peripheral site containing both NT and morphine binding sites.

Briefly, homogenates were prepared from freshly obtained PAG and the rest of brain of adult rats as according to Goedert M, et al., Brain Res. 304, 71–81 (1984) with the following modifications: the assay buffer contained the peptidase inhibitors 1,10 phenanthroline (1 $\mu$M) and aprotonin (5 mg/ml). For PAG and rest of brain binding assays, tissues were incubated with 0.3 mM [$^{125}$I]NT (NEN, Boston, Mass.) or 1 nM [$^3$H]morphine at room temperature for 30 or 60 minutes, respectively. Total and nonspecific binding was measured as described above except that binding sites were normalized to protein concentrations by BCA protein determination (Pierce Chemical Co., Rockford, Ill.).

Purified plasma membrane homogenates were prepared from freshly obtained jejunum and ileum and radioligand binding assays performed according to Goedert M, et al., Brain Res. 304, 71–81 (1984) and Makman M H, et al., Brain Res. 762, 247–250 (1997) with the following modifications: binding buffer contained 1,10 phenanthroline (1 $\mu$M) and aprotonin (5 mg/ml), and incubations were carried out at room temperature for 30 minutes for NT and 60 minutes for morphine. For these assays, intestinal homogenates (500 $\mu$g protein) were incubated with 80 pM [$^{125}$I]NT (NEN, Boston, Mass.) or 2 nM [$^3$H]morphine in a final volume of 1 ml. Nonspecific binding in brain and intestinal assays was determined using 1 $\mu$M unlabeled NT or morphine (RBI, Natick, Mass.). Binding data were analyzed as specific bound dpm/$\mu$g protein and compared to control (no PNA) animals for percent change.

The AS-NTR1-PNA oligomer treated animals had a 35%, 40%, and 65% reduction in the number of NTR1 binding sites in the PAG, rest of brain, and small intestine, respectively, compared to untreated animals (P<0.05 in all cases)(Table VI). In these animals, there was no significant difference in the number of morphine binding sites in the rest of brain or the small intestine compared to controls. These results again indicated the sequence specific manner in which PNA oligomers engender biological responses. In addition, the results indicate that PNA oligomers delivered intraperitoneally crossed not only the blood brain barrier, but also the plasma membrane of cells in brain and in the small intestine to knock down NTR1 polypeptide production.

TABLE VI

Biological responses engendered by intraperitoneal administration of the AS-NTR1-PNA oligomer.

| Tissue | Pretreatment | Responsiveness: NT[#] | Responsiveness: Morphine[##] | Binding (% change vs control) NT | Binding (% change vs control) Morphine |
|---|---|---|---|---|---|
| PAG | control | normal | normal | — | ND |
|  | AS-NTR1-PNA | lost | normal | −35 ± 9* | ND |
| Rest of Brain | control | normal | normal | — | — |
|  | AS-NTR1-PNA | lost | normal | −40 ± 1* | 2 ± 2 |
| Small Intestine | control | normal | normal | — | — |
|  | AS-NTR1-PNA | lost | normal | −65 ± 5* | −7 ± 8 |

*represents P < 0.05 (statistical analysis was done using the rank sum test with P < 0.05 being considered significant);
[#]represents NT responsiveness (anti-nociception and hypothermia);
[##]represents MOR responsiveness (anti-nociception);
ND represents not determined.

The observed decrease in [$^{125}$I]NT binding at peripheral sites (small intestine) was greater than that in brain. This result suggests that while the PNA oligomer clearly crosses the BBB and enters neuronal cells, it may enter peripheral sites more readily. In addition, the fact that a 35–40% reduction in [$^{125}$I]NT binding resulted in a nearly complete loss in behavioral and physiological responsiveness to NT indicates that the NT/NTR1 cascade is a threshold phenomenon.

5. Effects of PNA Oligomer Treatment on mRNA Levels

Messenger RNA (mRNA) levels for NTR1, MU1R, and GAPDH were measured in control and PNA-treated animals. Briefly, total RNA was isolated from approximately 20 mg of tissue using the S.N.A.P. total RNA Isolation Kit (Invitrogen, Carlsbad, Calif.). Quantitative RT-PCR was performed on treated and control animals using GAPDH as an internal standard and PCR fragments of the human NTR and of a GAPDH deletion mutant as exogenous standards. First strand cDNA was synthesized from approximately 500 ng of total RNA using the cDNA Cycle Kit (Invitrogen, Carlsbad, Calif.). PCR was performed on a GeneAmp PCR System 9600 (Perkin Elmer, Norwalk, Conn.) using end-labeled primer and TAq DNA Polymerase (Gibco-BRL, Gaithersburg, Md.). Products were separated on a 5% acrylamide gel containing 7 M urea, and detected using a Storm860 Phosphoimager (Molecular Dynamics, Sunnyvale, Calif.). Data were analyzed using ImageQuant Software (Molecular Dynamics, Sunnyvale Calif.). To control for any diurnal mRNA level fluctuations that may occur, the PNA injection time was controlled such that the tissue harvest time was identical in each animal group.

Figure 19:
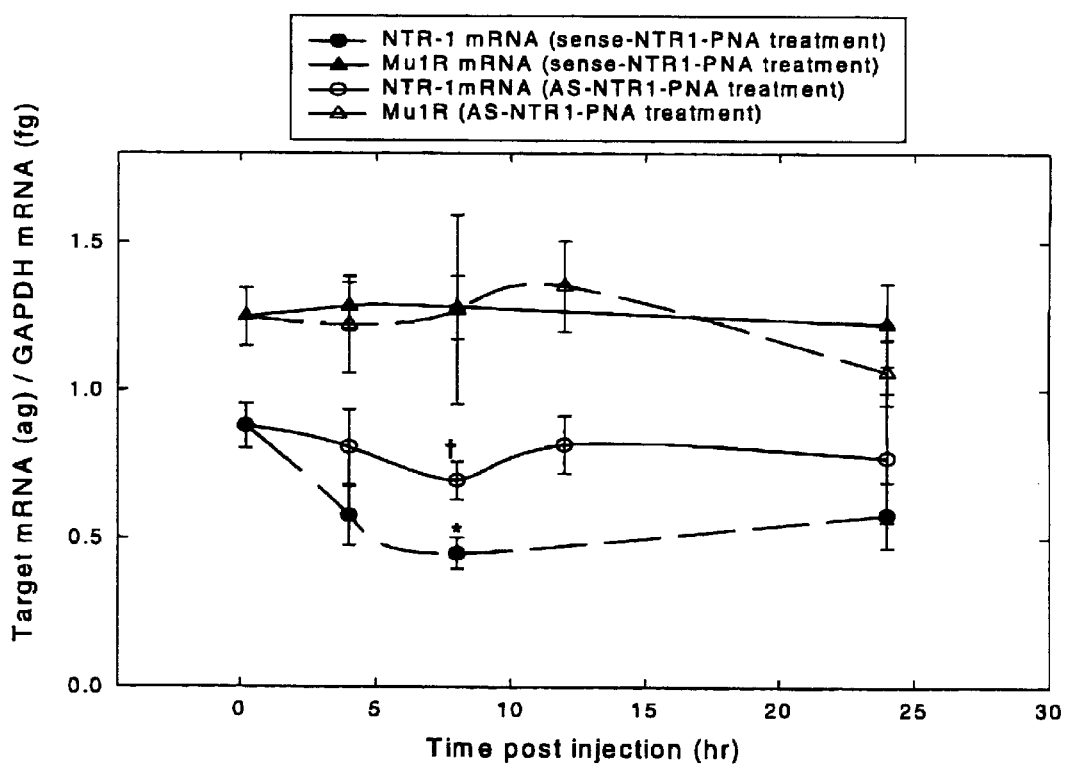
FIG. 19 is a graph plotting the ratio of NTR1 or MU1R mRNA to GAPDH mRNA in animals treated with the AS-NTR1-PNA or sense-NTR1-PNA oligomers. The 0 time represents animals receiving no PNA. * represents P<0.005 vs control, and † represents P<0.05 vs. sense-NTR1-PNA.

Animals treated intracranially with the AS-NTR1-PNA oligomer (5 $\mu$g) exhibited no significant change in the NTR1/GAPDH or MU1R/GAPDH ratio of mRNA over time (FIG. 19). This result indicates that antisense PNA oligomers do not activate mRNA degradation mechanisms such as those involving RNase H, but that PNA/RNA complexes block the translation of mRNA molecule into a polypeptide presumably by steric hindrance. On the other hand, animals treated intracranially with the sense-NTR1-PNA oligomer (5 µg) exhibited a 50% reduction in the NTR1/GAPDH ratio of mRNA at 8 hours (P<0.05 vs control and vs AS-NTR1-PNA treated animals at 8 hours). Importantly, no change in the MU1R/GAPDH ratio was observed at any time point in the animals treated with the sense-NTR1-PNA oligomer. Taken together, these results indicate that sense PNA oligomers are effective antigene agents in vivo.

6. Effects of PNA Oligomer Treatment on Reverse Transcription

An in vitro reverse transcription assay was performed as follows. Total RNA was isolated from 20 mg of tissue using the RNeasy Kit (Qiagen, Chatsworth, Calif.). After isolation, total RNA (1 µg) was incubated with the PNA oligomers (600 ng) at 40° C. for 40 minutes. Exogenous cRNA standards were added, and cDNA was synthesized using the cDNA Cycle Kit and gene-specific primers for NTR1 and GAPDH (Invitrogen, Carlsbad, Calif.). The exogenous cRNA standards were synthesized from dsDNA templates using the Megashort-Script Kit (Ambion, Austin, Tex.). The dsDNA templates for exogenous cRNA standards for the NTR1- and GAPDH-specific cDNA reactions were constructed using the PCR MIMIC Construction Kit (Clontech) and composite primers. The composite primers contained the T7 RNA Polymerase binding site as well as NTR1- or GAPDH-specific sequences that correspond to the primer sequences used in each individual cDNA reaction. After using the cDNA Cycle Kit, quantitative PCR was performed on each sample. The products then were separated on a 2% agarose gel and stained with Vista Green (Amersham, Arlington Heights, Ill.). Products were detected using a Storm860 Phosphoimager (Molecular Dynamics, Sunnyvale, Calif.) and data were analyzed using Image Quant Software (Molecular Dynamics, Sunnyvale, Calif.).

Figure 20:
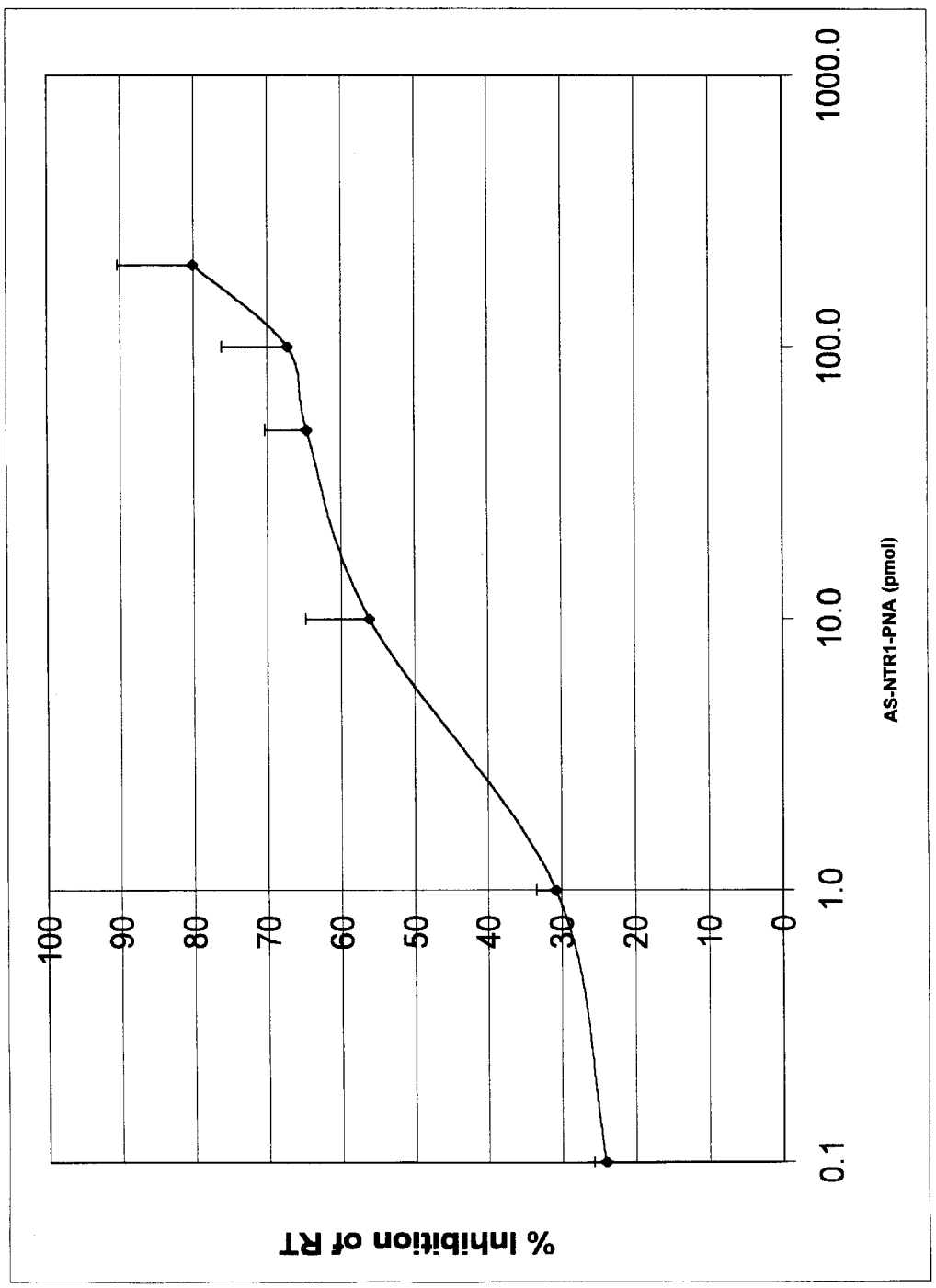
FIG. 20 is a graph depicting the percent inhibition of reverse transcription versus increasing concentrations of the AS-NTR1-PNA oligomer.

Using this in vitro reverse transcription assay, 1 µg of total RNA isolated from the brain of an untreated rat was incubated with 600 ng of the AS-NTR1-PNA or mismatch-AS-NTR1-PNA oligomer and NTR1 cDNA production assessed. Total RNA samples containing the mismatch-AS-NTR1-PNA oligomer exhibited a level of NTR1 cDNA synthesis similar to that observed in samples containing no PNA. Total RNA samples containing the AS-NTR1-PNA oligomer, however, exhibited a 65% reduction in NTR1 cDNA synthesis as evidenced by gel electrophoresis. Specifically, reactions containing the AS-NTR1-PNA oligomer consistently failed to produce NTR1 cDNA product with the same intensity as that produced in reactions not containing the AS-NTR1-PNA oligomer. Controls such as cRNA standards for the target gene and GAPDH verified the efficiency of cDNA synthesis and PCR product formation. In addition, PNA/RNA complexes inhibited reverse transcription in a dose-dependant manner (FIG. 20). Taken together, these results indicate that PNA/RNA complexes inhibit reverse transcriptase in a sequence specific as well as dose dependant manner.

Example 9

Direct Measurement of PNA Oligomers in Tissue

Behavioral, physiological, and binding data indicate that the AS-NTR1-PNA oligomer not only acts in a sequence specific manner, but also crosses the blood brain barrier (BBB) in its carrier-free form after intraperitoneal administration. To confirm the presence and measure the amount of PNA in brain after extracranial administration, a sensitive gel shift assay was developed. This assay involves using a radioactively-labeled oligonucleotide having sequence specificity for a PNA oligomer as a probe to detect that PNA oligomer. Briefly, a sample is prepared and incubated with a probe. If the sample contains a PNA oligomer having sequence specificity for the probe, then the probe can bind that PNA oligomer. This bound form of the probe then can be detected and quantified using gel electrophoresis since a probe bound to a PNA oligomer migrates differently than an unbound probe on a gel.

Brain extracts were prepared from either untreated animals or animals treated intraperitoneally with 10 mg/kg of the AS-NTR1-PNA oligomer. For the treated animals, brain tissue was collected 8 hours post treatment. To prepare brain extracts, flash frozen brain tissue (minus the PAG and hypothalamus) were homogenized in 1 mM Tris (pH 4.0), 0.1 mM EDTA at a concentration of 1.5 ml/g wet weight of tissue. This acidic condition can protonate cytosine bases as well as the N-terminal amino group of the PNA oligomer, which presumably increases the solubility of the PNA oligomer and allows the PNA oligomer to be found in an aqueous phase during the later extraction step. Samples were boiled for five minutes. This boiling step can free the bound PNA oligomer from its target sequence, and inactivate nucleases that may interfere with the integrity of the DNA oligonucleotide probe. Then, the samples were spun two to three times at 35,600×g for 10 minutes each to pellet insoluble material and the supernatants collected. Supernatants were extracted with 10 volumes of $CHCl_3$:MeOH (2:1 v/v) to remove glycolipids that may interfere with gel electrophoresis, and spun briefly at 1,000×g to separate phases. For the standard curves using known amounts of a PNA oligomer, the PNA oligomer was added to the supernatant before the $CHCl_3$:MeOH extraction. The supernatants were collected in a fresh tube, lyophilized, and resuspended in 30 to 40 µl of water.

Once prepared, approximately 400 pg of probe was added to each 30 to 40 µl sample. To prepare the probe, a DNA oligonucleotide (Gibco BRL, Gaithersburg, Md.) complementary to the AS-NTR1-PNA oligomer was end-labeled using T4 Polynucleotide Kinase (Gibco BRL) and [Gamma-$^{32}$P]ATP or [Gamma-$^{33}$P]ATP (New England Nuclear, Boston, Mass.) according to manufacturer's instructions. Unincorporated nucleotides were removed using a Chroma-Spin 10 column (Clontech, Palo Alto, Calif.) and gel purified on a 20% acrylamide gel. The portion of the gel containing the probe was excised and the probe was eluted into 100 to 150 µl of 10 mM Tris (pH 8.0), 1 mM EDTA.

After adding the probe, the samples were incubated at room temperature for 20 minutes. After incubation, Ficoll loading buffer (10×) was added to each sample and the samples were run on a 1.5 mm thick 20% polyacrylamide gel in TBE for 150 volt-hours (e.g., 180 Volts for 50 minutes). Gels were incubated in gel drying solution (Bio-Rad, Hercules, Calif.) for 30 minutes and dried on a gel dryer. Signal was detected using a Storm860 Phosphoimager (Molecular Dynamics, Sunnyvale, Calif.) and data were analyzed using ImageQuant Software (Molecular Dynamics, Sunnyvale, Calif.).

Figure 21:
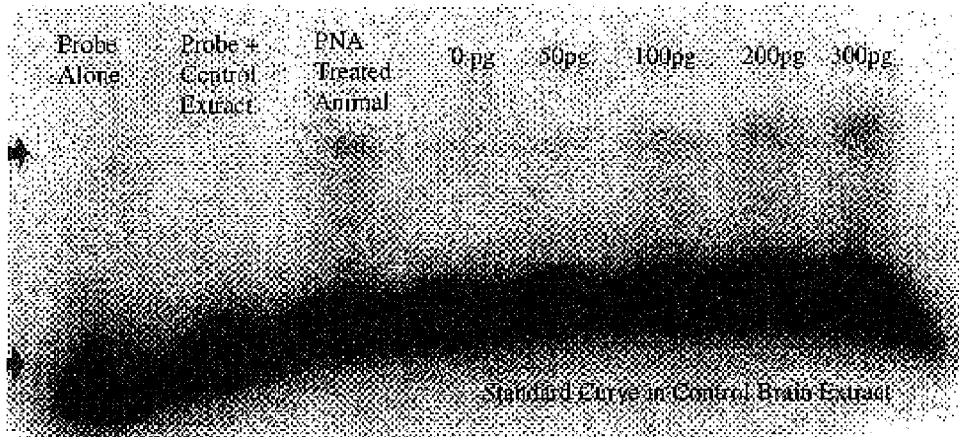
FIG. 21 is a picture of a gel depicting a gel shift assay using brain extracts collected from treated or untreated animals. Lane 1) probe alone in TE buffer; Lane 2) control brain+probe; Lane 3) brain extract from AS-NTR1-PNA-treated animal+probe. Lanes 4–8 contained control brain extract with probe 0, 50, 100, 200, 300 pg of PNA standard, respectively. The top arrow indicates the position of PNA/oligonucleotide probe complex, while the bottom arrow indicates the position of excess free oligonucleotide probe.

AS-NTR1-PNA oligomer was detected in brain extracts prepared from treated animals and not in those extracts prepared from untreated animals. To control for the possibility that PNA oligomers may be in the capillaries of brain tissue after intraperitoneal injection and not actually in the cellular tissue of brain itself, animals were perfused with sterile saline just prior to the collection of brain tissue. Again, the AS-NTR1-PNA oligomer was detected in brain extracts prepared from treated animals and not untreated animals (FIG. 21). In addition, the levels of PNA oligomer detected in brain extracts from perfused and non-perfused treated animals were similar, indicating that very little, if any, PNA oligomer remains in blood after 8 hours when given intraperitoneally at a concentration of 10 mg/kg. Moreover, the shifts in mobility observed in samples from treated animals were similar to the shifts observed in control samples spiked with the AS-NTR1-PNA oligomer. Since the loss of even a single PNA base is easily distinguishable using this gel shift assay, these similar shifts in mobility indicate that the AS-NTR1-PNA oligomers recovered from brain were unaltered. Taken together, these results indicate that extracranially administered PNA oligomers cross the BBB and remain in brain tissue for at least 8 hours in their original form.

Figure 22:
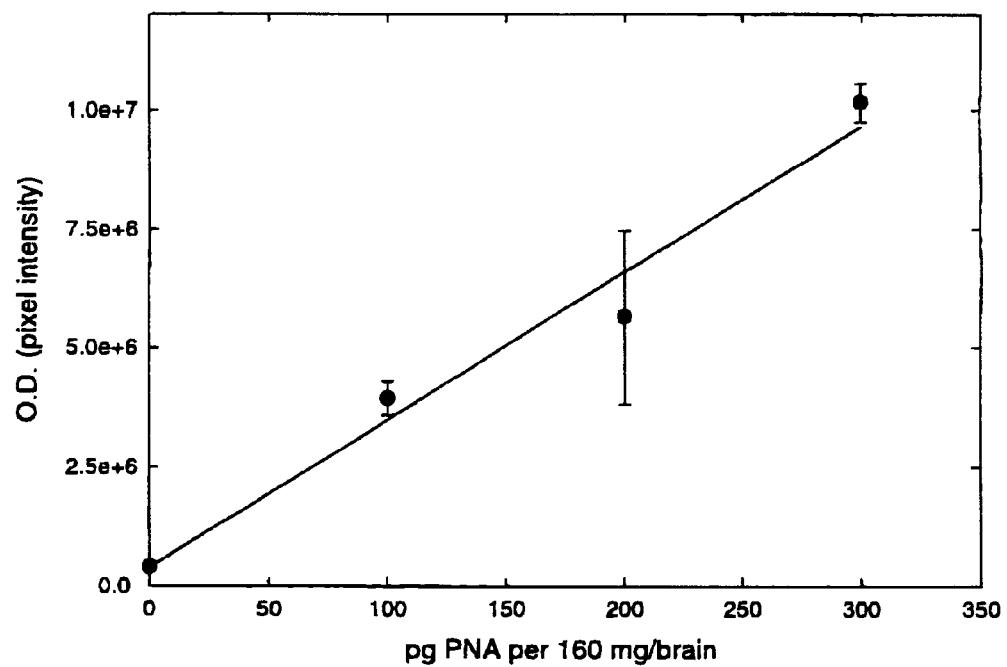
FIG. 22 is a graph plotting a representative standard curve obtained from a gel shift assay using brain tissue.

Using known amounts of the AS-NTR1-PNA oligomer added directly to brain tissue collected from untreated animals and correcting for recovery of the PNA oligomer during extraction (60%), a standard curve (y=31030x+375700; $R^2$=0.97) was produced (FIGS. 21 and 22). From this standard curve, the concentration of the AS-NTR1-PNA oligomer within brain 8 hours after intraperitoneal administration was calculated as 2.4±0.3 ng/whole brain. It is noted that as little as 50 pg of the AS-NTR1-PNA oligomer was detected when directly added to 160 mg wet weight of brain tissue from an untreated animal (500 pg/whole brain) as evidenced by a shift in the electrophoretic mobility of the radioactively-labeled probe. Thus, this gel shift assay not only detects the presence of AS-NTR1-PNA oligomer within brain, but also provides a measure of the amount of PNA within brain tissue.

This gel shift assay was used to detect PNA oligomers in tissues other than brain, including heart, kidney, liver, spleen, and blood. Animals were injected intraperitoneally with 10 mg/kg of the AS-NTR1-PNA oligomer and perfused 2 hours later with sterile saline. Brain, heart, kidney, liver, and spleen tissue were collected and prepared as described above.

For blood, the AS-NTR1-PNA oligomer (10 mg/kg) was injected intravenously into animals. Five minutes later, 150 µl of whole blood was collected and 15 µl of 0.13 M buffered citrate solution was added. Then, the blood samples were spun briefly and serum collected in a fresh tube. The serum was diluted (1 µl aliquots of sera were diluted to a final volume of 30 µl in TE buffer, pH 8.0) and probe added as described above for brain tissue.

The AS-NTR1-PNA oligomer was detected in each tissue as evidenced by the presence of the shift in mobility of the radio-labeled probe. This shift is similar to the shift observed in FIG. 21. In addition, a standard curve was produced by adding known amounts of the PNA oligomer to liver tissue prior to extraction. This standard curve was similar to the standard curve produced using brain extract. From these results, the level of detection using $^{32}$P- or $^{33}$P-labeled probe was within the range of 30 pg to greater than 400 pg of PNA per lane. Thus, this gel shift assay provides a very sensitive and reliable assay for detecting PNA oligomers within biological samples collected from an animal.

Example 11

Sense and Antisense Combination Treatments

Sense and antisense PNA oligomers are given in combination to engender a biological response that is more pronounced, longer lasting, or otherwise different from the biological response engendered by either the sense or antisense PNA oligomer alone. The sense and antisense PNA oligomers given in combination typically are not complementary to each other and thus do not exhibit sequence specificity for an identical target sequence.

For example, four groups of animals can be used to determine the effects of a combination treatment of sense and antisense PNA oligomers. Each group can contain four rats. The first group of rats can be treated intraperitoneally with an antisense PNA oligomer, such as the AS-NTR1-PNA oligomer (e.g., 10 mg/kg). The second group of rats can be treated intraperitoneally with a sense PNA oligomer, such as, +376S-NTR1-PNA (e.g., 10 mg/kg). The +376S-NTR1-PNA oligomer (5'-TACAACTTCATCTG-3' (SEQ ID NO:14)) is a 14-mer that targets a portion of the coding strand of DNA that encodes NTR1. The +376 designation indicates that the +376S-NTR1-PNA oligomer targets a portion of nucleic acid encoding NTR1 that is 376 nucleotides 3' of the NTR1 translational start site. The third group of rats can be treated intraperitoneally with both an antisense and sense PNA oligomer, such as the AS-NTR1-PNA oligomer (e.g., 10 mg/kg) and the +376S-NTR1-PNA oligomer (e.g., 10 mg/kg). The fourth group of rats can be treated with the vehicle used to deliver the PNA oligomers, such as saline.

After treatment, each group of rats can be tested for NT responsiveness. As described herein, a hot plate test can be used to assess NT-induced anti-nociception and rectal temperature can be used to assess NT-induced hypothermia. In addition, the [$^{125}$I]NT binding assay described herein can be used to assess the level of reduction in NTR1 polypeptide expression.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for engendering a biological response in an animal containing a cell, said method comprising administering to said animal a polyamide nucleic acid oligomer containing neutral amide backbone linkages under conditions wherein said oligomer enters said cell and engenders said biological response in a sequence specific manner, said oligomer having sequence specificity for a target sequence within said cell while possessing at least one base pair mismatch with said target sequence, and wherein said biological response is associated with said target sequence.

2. The method of claim 1, wherein said oligomer comprises a sequence of SEQ ID NO:12.

3. The method of claim 1, wherein said target sequence comprises at least a portion of a coding strand of DNA within said cell, wherein said portion regulates, or is a template for, synthesis of an RNA molecule.

4. The method of claim 1, wherein said target sequence comprises at least a portion of an RNA that regulates expression of or encodes a polypeptide.

5. The method of claim 1, wherein said biological response is characterized by a physiological change in said animal.

6. The method of claim 1, wherein said cell is a nervous system cell.

7. A method for engendering a biological response in an animal containing a cell with a target sequence, said method comprising:
   a) selecting a first polyamide nucleic acid oligomer from a kit, said kit comprising a plurality of polyamide nucleic acid oligomers containing neutral amide backbone linkages, wherein each of said oligomers has sequence specificity for said target sequence while possessing a sequence different from the sequence of the other oligomers, and
   b) administering said first selected oligomer to said animal under conditions wherein said first selected oligomer enters said cell and engenders said biological response associated with said target sequence in a sequence specific manner.

8. The method of claim 7, wherein said method further comprises:
   a) selecting a second polyamide nucleic acid oligomer from said kit, and
   b) administering said second selected oligomer to said animal under conditions wherein said second selected oligomer enters said cell and engenders said biological response to a modulated degree compared to the response engendered by said first selected oligomer.

9. The method of claim 1, wherein said method comprises detecting said biological response.

10. The method of claim 1, wherein said oligomer is carrier-free.

11. The method of claim 1, wherein said oligomer is acridine-free.

12. The method of claim 1, wherein said oligomer is protein-free.

13. The method of claim 1, wherein said oligomer is DNA-free.

14. The method of claim 1, wherein said oligomer is peptide-free.

15. The method of claim 1, wherein said oligomer is bis-PNA-free.

16. The method of claim 1, wherein said oligomer is biotin-free.

17. The method of claim 1, wherein said oligomer is fluorescein-free.

18. The method of claim 1, wherein said administration is an extracranial administration.

19. The method of claim 1, wherein said oligomer crosses a blood-brain barrier of said animal.

20. The method of claim 3, wherein said RNA molecule encodes a polypeptide.

21. The method of claim 4 or 20, wherein said polypeptide is expressed intracranially in said animal.

22. The method of claim 4 or 20, wherein said polypeptide is expressed extracranially in said animal.

23. The method of claim 4 or 20, wherein said polypeptide is expressed in the gastrointestinal tract.

24. The method of claim 4 or 20, wherein said polypeptide participates in cell signaling.

25. The method of claim 1, wherein said biological response is a modification of polypeptide expression.

26. The method of claim 1, wherein the site of said administration is outside the central nervous system of said animal.

27. The method of claim 7, wherein said target sequence comprises at least a portion of a coding strand of DNA within said cell, wherein said portion regulates, or is a template for, synthesis of an RNA molecule.

28. The method of claim 27, wherein said RNA molecule encodes a polypeptide.

29. The method of claim 7, wherein said target sequence comprises at least a portion of an RNA that regulates expression of or encodes a polypeptide.

30. The method of claim 28 or 29, wherein said polypeptide is expressed intracranially in said animal.

31. The method of claim 28 or 29, wherein said polypeptide is expressed extracranially in said animal.

32. The method of claim 28 or 29, wherein said polypeptide is expressed in the gastrointestinal tract.

33. The method of claim 28 or 29, wherein said polypeptide participates in cell signaling.

34. The method of claim 7, wherein said biological response is a modification of polypeptide expression.

35. The method of claim 7, wherein the site of said administration to said animal is outside the central nervous system of said animal.

36. The method of claim 7, wherein said polyamide nucleic acid oligomers are carrier-free.

37. The method of claim 7, wherein said polyamide nucleic acid oligomers are acridine-free.

38. The method of claim 7, wherein said polyamide nucleic acid oligomers are protein-free.

39. The method of claim 7, wherein said polyamide nucleic acid oligomers are DNA-free.

40. The method of claim 7, wherein said polyamide nucleic acid oligomers are peptide-free.

41. The method of said claim 7, wherein said polyamide nucleic acid oligomers are bis-PNA-free.

42. The method of claim 7, wherein said polyamide nucleic acid oligomers are biotin-free.

43. The method of claim 7, wherein said polyamide nucleic acid oligomers are fluorescein-free.

* * * * *